(12) United States Patent
Dounay et al.

(10) Patent No.: US 8,598,200 B2
(45) Date of Patent: Dec. 3, 2013

(54) KAT II INHIBITORS

(75) Inventors: Amy B Dounay, Ledyard, CT (US);
Laura McAllister, Pawcatuck, CT (US);
Vinod D Parikh, Mystic, CT (US);
Suobao Rong, Groton, CT (US);
Patrick R Verhoest, Old Lyme, CT (US)

(73) Assignee: Pfizer Inc., New York, NY (US)

( * ) Notice: Subject to any disclaimer, the term of this patent is extended or adjusted under 35 U.S.C. 154(b) by 7 days.

(21) Appl. No.: 13/307,636

(22) Filed: Nov. 30, 2011

(65) Prior Publication Data
US 2012/0302599 A1  Nov. 29, 2012

Related U.S. Application Data

(60) Provisional application No. 61/418,802, filed on Dec. 1, 2010.

(51) Int. Cl.
*A01N 43/42* (2006.01)
*A61K 31/44* (2006.01)
*A01N 43/40* (2006.01)
*A61K 31/445* (2006.01)
*A01N 43/56* (2006.01)
*A61K 31/415* (2006.01)

(52) U.S. Cl.
USPC ............ 514/303; 514/330; 514/407; 514/322

(58) Field of Classification Search
None
See application file for complete search history.

(56) References Cited

U.S. PATENT DOCUMENTS

| 4,282,361 A | 8/1981 | Hecht et al. ........... A61K 31/505 |
| 2005/0009870 A1 | 1/2005 | Sher et al. |
| 2006/0009509 A1 | 1/2006 | Grubb et al. ......... A61K 31/404 |

OTHER PUBLICATIONS

Han et al. "Structure, expression, and function of kynurenine aminotransferases in human and rodent brains", Cell.Mol.LifeSci., 2010, vol. 67, pp. 353-368.*

* cited by examiner

*Primary Examiner* — James D Anderson
*Assistant Examiner* — Stephanie Springer
(74) *Attorney, Agent, or Firm* — Feng Shao

(57) ABSTRACT

Compounds of Formula I:

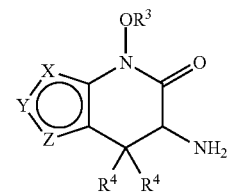

wherein X, Y, Z, $R^1$, $R^2$, $R^3$, $R^4$ are as defined herein, and pharmaceutically acceptable salts thereof, are described as useful for the treatment of cognitive deficits associated with schizophrenia and other psychiatric, neurodegenerative and/or neurological disorders in mammals, including humans.

15 Claims, No Drawings

KAT II INHIBITORS

This application claims the benefit of priority to U.S. provisional patent application Ser. No. 61/418,802 filed Dec. 1, 2010, the disclosure of which is hereby incorporated by reference in its entirety.

FIELD OF THE INVENTION

The present invention relates to the treatment of cognitive deficits associated with schizophrenia and other psychiatric, neurodegenerative and/or neurological disorders in mammals, including humans. More particularly, this invention relates to bicyclic inhibitors of the KAT II enzyme, useful for the treatment of such disorders.

BACKGROUND OF THE INVENTION

KAT (kynurenine aminotransferase) II is a primary enzyme in the brain for catalyzing the transamination of kynurenine to KYNA (kynurenic acid) (E. Okuno et al., *J. Neurochem.*, vol. 57, 533-540, 1991). KYNA is an effective excitatory amino acid (EAA) receptor antagonist with affinity for the glycine modulatory site of the N-methyl-D-aspartate (NMDA) receptor complex (M. Kessler et al., *J. Neurochem.*, vol. 52, pp. 1319-1328, 1989). As a naturally occurring brain metabolite, KYNA probably serves as a negative endogenous modulator of cerebral glutamatergic function (R. Schwarcz et al., *Ann. N.Y. Acad. Sci.*, vol. 648, pp. 140-153, 1992), and activator of arylhydrocarbon receptors (B. DiNatale et al., *Toxicol. Sci. vol* 115, pp. 89-97, 2010).

EAA receptors and in particular NMDA receptors are known to play a central role in the function of the mammalian brain (J. C. Watkins and G. L. Collingridge, Eds., *The NMDA Receptor*, Oxford University Press, Oxford, 1989, p. 242). For example, NMDA receptor activation is essential for cognitive processes, such as, for example, learning and memory (Watkins and Collingridge, supra, pp. 137-151). Therefore, reducing KYNA synthesis by inhibition of its synthetic enzyme may enhance EAA signaling and improve cognitive processes, especially in disease states where NMDA hypofunction is anticipated. Thus, there is a need for compounds which act as KAT II inhibitors to reduce KYNA synthesis within the brain to improve cognitive dysfunction in human disease states.

SUMMARY OF THE INVENTION

The present invention is directed to compounds of Formula I:

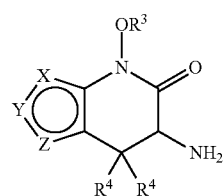

I or a pharmaceutically acceptable salt thereof, wherein
solid circle represents single or double bonds as valency requires;
X, Y, and Z are independently selected from a group consisting of =N—, —N=, $NR^1$, and $CR^2$, provided that at least two are other than $CR^2$;

$R^1$ is H, alkyl, cycloalkyl, heterocycloalkyl, aryl, aralkyl, heteroaryl, $SO_2NR^5R^6$, or $SO_2R^{5a}$, wherein each said alkyl, cycloalkyl, heterocycloalkyl, aryl, aralkyl, and heteroaryl may be substituted with one or more substituents independently selected from hydroxy, amino, halo, alkyl, haloalkyl, CN, alkoxy, haloalkoxy, alkylamino, aminoalkyl, $—(CH_2)_n$cycloalkyl, $—(CH_2)_n$heterocycloalkyl, $—(CH_2)_n$aryl, and $—(CH_2)_n$heteroaryl;

$R^2$ is H, halo, alkyl, cycloalkyl, heterocycloalkyl, aryl, aralkyl, heteroaryl, alkoxy, cycloalkyloxy, aryloxy, aralkyloxy, heterocycloalkyloxy, heteroaryloxy, CN, $—(CH_2)_n NR^5R^6$, $C(=O)NR^5R^6$, $SO_2NR^5R^6$, $SO_2R^{5a}$, $NR^5SO_2R^{5a}$, or $NR^5C(=O)R^{5a}$, wherein each said alkyl, cycloalkyl, heterocycloalkyl, aryl, aralkyl, heteroaryl, alkoxy, cycloalkyloxy, aryloxy, aralkyloxy, heterocycloalkyloxy, and heteroaryloxy may be substituted with one or more substituents independently selected from hydroxy, amino, halo, alkyl, haloalkyl, CN, alkoxy, haloalkoxy, alkylamino, aminoalkyl, $—(CH_2)_n$cycloalkyl, $—(CH_2)_n$heterocycloalkyl, $—(CH_2)_n$aryl, and $—(CH_2)_n$heteroaryl;

$R^3$ is H, $C(=O)R^7$, $C(=O)OR^7$, $C(=O)NR^{7a}R^{7b}$, or $(CH_2)R^8$;

each $R^4$ is independently H, methyl, or fluoromethyl;

$R^5$ and $R^6$ are independently H, alkyl, fluoroalkyl, aryl, or heteroaryl, or $R^5$ and $R^6$ of $C(=O)NR^5R^6$ or $SO_2NR^5R^6$, together with the nitrogen to which they are attached, may form a heterocycloalkyl;

$R^{5a}$ is alkyl, fluoroalkyl, aryl, or heteroaryl;

$R^7$ is alkyl, aryl, heteroaryl, or cycloalkyl, wherein each said alkyl, aryl, heteroaryl, and cycloalkyl may be substituted with one or more substituents independently selected from hydroxy, amino, halo, alkoxy, and aminoalkyl;

$R^{7a}$ and $R^{7b}$ are independently H, alkyl, aryl, heteroaryl, or cycloalkyl, wherein each said alkyl, aryl, heteroaryl, and cycloalkyl may be substituted with one or more substituents independently selected from hydroxy, amino, halo, alkoxy, and aminoalkyl, or, when $R^3$ is $C(=O)NR^{7a}R^{7b}$, $R^{7a}$ and $R^{7b}$, together with the nitrogen atom to which they are attached, may form a 5- or 6-membered N-containing heterocyclic ring;

$R^8$ is

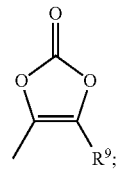

$R^9$ is H, alkyl, aryl, heteroaryl, or cycloalkyl, wherein each said alkyl, aryl, heteroaryl, and cycloalkyl may be substituted with one or more substituents independently selected from hydroxy, amino, halo, alkoxy, and aminoalkyl; and each n is independently 0, 1, 2, or 3.

This invention also includes pharmaceutically acceptable salts, hydrates, solvates, isomers, crystalline and non-crystalline forms, isomorphs, polymorphs, and metabolites of compounds of Formula I. This invention also includes all tautomers and stereochemical isomers of these compounds.

This invention also is directed, in part, to a method for treating a KAT II-mediated disorder in a mammal. Such disorders include cognitive deficits associated with schizophrenia and other psychiatric, neurodegenerative and/or neurological disorders. The method comprises administering a compound of Formula I or a pharmaceutically acceptable salt thereof, to the mammal in an amount that is therapeutically effective to treat the condition.

When introducing elements of the present invention or the exemplary embodiment(s) thereof, the articles "a," "an," "the" and "said" are intended to mean that there are one or more of the elements. The terms "comprising," "including" and "having" are intended to be inclusive and mean that there may be additional elements other than the listed elements. Although this invention has been described with respect to specific embodiments, the details of these embodiments are not to be construed as limitations to the invention, the scope of which is defined by the appended claims.

DETAILED DESCRIPTION OF THE INVENTION

One embodiment of the present invention is a compound of Formula I as described above.

Another embodiment of the present invention is a compound of Formula I, or a pharmaceutically acceptable salt thereof, wherein one of X or Y is $NR^1$ and the other is —N= or =N—; Z is $CR^2$; $R^1$ is $C_1$ to $C_6$ alkyl; $C_3$ to $C_6$ cycloalkyl, aryl, or arylalkyl; $R^2$ is H, $C_1$ to $C_6$ alkyl, $C_3$ to $C_6$ cycloalkyl, aryl or arylalkyl; and wherein each said alkyl, cycloalkyl, aryl, and arylalkyl may be substituted as allowed in Formula I and $R^3$ and $R^4$ are as defined in any embodiment of Formula I.

Another embodiment of the present invention is a compound of Formula I, or a pharmaceutically acceptable salt thereof, wherein X is $NR^1$; Y is —N= or =N—; Z is $CR^2$; and wherein $R^1$, $R^2$, $R^3$, and $R^4$ are as defined in any embodiment of Formula I. In one such embodiment, the compound of Formula I has the following structure:

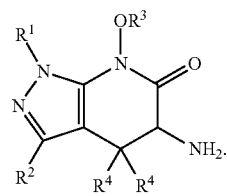

Another embodiment of the present invention is a compound of Formula I, or a pharmaceutically acceptable salt thereof, wherein the alkyl of $R^1$ is $C_1$ to $C_3$ alkyl; and $R^2$, $R^3$, and $R^4$ are as defined in any embodiment of Formula I.

Another embodiment of the present invention is a compound of Formula I, or a pharmaceutically acceptable salt thereof, wherein the aryl of $R^1$ and $R^2$ is phenyl or naphthyl, and the arylalkyl of $R^1$ and $R^2$ is —$CH_2$-phenyl or —$CH_2$-naphthyl, and wherein any phenyl or naphthyl may be substituted with one or more substituents independently selected from halo, alkyl (e.g., $C_1$ to $C_3$ alkyl), haloalkyl (e.g., $CF_3$), alkoxy (e.g., methoxy), haloalkoxy (e.g., $CF_3$—O), and CN.

Another embodiment of the present invention is a compound of Formula I, or a pharmaceutically acceptable salt thereof, wherein X is —N= or =N—; Y is $NR^1$; Z is $CR^2$; $R^1$ is $C_1$ to $C_6$ alkyl; $R^2$ is H, aryl or arylalkyl; and wherein each said alkyl, aryl, and arylalkyl may be substituted as defined in Formula I, and wherein $R^3$ and $R^4$ are as defined in any embodiment of Formula I. In one such embodiment, the compound of Formula I has the following structure:

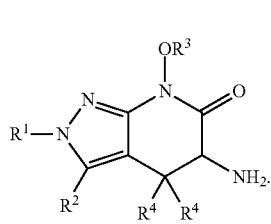

Another embodiment of the present invention is a compound of Formula I, or a pharmaceutically acceptable salt thereof, wherein the aryl of $R^2$ is phenyl or naphthyl, and the arylalkyl of $R^2$ is —$CH_2$-phenyl or —$CH_2$-naphthyl, and wherein any phenyl or naphthyl may be substituted with one or more substituents independently selected from halo, alkyl (e.g., $C_1$ to $C_3$ alkyl), haloalkyl (e.g., $CF_3$), alkoxy (e.g., methoxy), haloalkoxy (e.g., $CF_3$—O), and CN, and wherein $R^1$, $R^3$ and $R^4$ are as defined in any embodiment of Formula I.

Another embodiment of the present invention is a compound of Formula I, or a pharmaceutically acceptable salt thereof, wherein X is $CR^2$; Y is $NR^1$; and Z is —N= or =N—; $R^1$ is H, $C_1$ to $C_6$ alkyl, aryl or arylalkyl; $R^2$ is H or $C_1$ to $C_3$ alkyl; and wherein each said alkyl, aryl, and arylalkyl may be substituted as allowed in any embodiment of Formula I and $R^3$ and $R^4$ are as defined in any embodiment of Formula I. In one such embodiment, the compound of Formula I has the following structure:

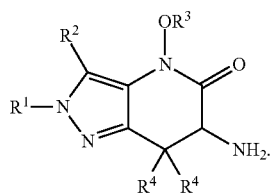

Another embodiment of the present invention is a compound of Formula I, or a pharmaceutically acceptable salt thereof, wherein X is $CR^2$; Y is —N= or =N—; and Z is $NR^1$; $R^1$ is H, $C_1$ to $C_6$ alkyl, aryl or arylalkyl; $R^2$ is H or $C_1$ to $C_3$ alkyl; and wherein each said alkyl, aryl, and arylalkyl may be substituted as allowed in any embodiment of Formula I and $R^3$ and $R^4$ are as defined in any embodiment of Formula I. In one such embodiment, the compound of Formula I has the following structure:

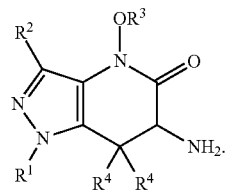

Another embodiment of the present invention is a compound of Formula I, or a pharmaceutically acceptable salt thereof, wherein aryl of $R^1$ is phenyl or naphthyl, and the arylalkyl of $R^1$ is —$CH_2$-phenyl or —$CH_2$-naphthyl, and wherein any phenyl or naphthyl may be substituted with one or more substituents selected from halo, alkyl (e.g., $C_1$ to $C_3$ alkyl), haloalkyl (e.g., $CF_3$), alkoxy (e.g., methoxy), haloalkoxy (e.g., $CF_3$—O), and CN and $R^2$, $R^3$ and $R^4$ are as defined in any embodiment of Formula I.

Furthermore, by way of example and not as a limitation, when aryl and arylalkyl are specified for $R^1$ and $R^2$, $R^1$ and $R^2$ may be any other variable as allowed in Formula I. When such definitions are used $R^1$ and $R^2$ may have the following definitions:

$R^1$ is H, alkyl, cycloalkyl, heterocycloalkyl, phenyl, naphthyl, —CH$_2$-phenyl, —CH$_2$-naphthyl, heteroaryl, SO$_2$NR$^5$R$^6$, or SO$_2$R$^{5a}$, wherein each said alkyl, cycloalkyl, heterocycloalkyl, phenyl, naphthyl, —CH$_2$-phenyl, —CH$_2$-naphthyl, and heteroaryl may be substituted with one or more substituents independently selected from hydroxy, amino, halo, alkyl, haloalkyl, CN, alkoxy, haloalkoxy, alkylamino, aminoalkyl, —(CH$_2$)$_n$cycloalkyl, —(CH$_2$)$_n$heterocycloalkyl, —(CH$_2$)$_n$aryl, and —(CH$_2$)$_n$heteroaryl;

$R^2$ is H, halo, alkyl, cycloalkyl, heterocycloalkyl, phenyl, naphthyl, —CH$_2$-phenyl, —CH$_2$-naphthyl, heteroaryl, alkoxy, cycloalkyloxy, aryloxy, aralkyloxy, heterocycloalkyloxy, heteroaryloxy, CN, —(CH$_2$)$_n$NR$^5$R$^6$, C(=O)NR$^5$R$^6$, SO$_2$NR$^5$R$^6$, SO$_2$R$^{5a}$, NR$^5$SO$_2$R$^{5a}$, or NR$^5$C(=O)R$^{5a}$, wherein each said alkyl, cycloalkyl, heterocycloalkyl, phenyl, naphthyl, —CH$_2$-phenyl, —CH$_2$-naphthyl, heteroaryl, alkoxy, cycloalkyloxy, aryloxy, aralkyloxy, heterocycloalkyloxy, and heteroaryloxy may be substituted with one or more substituents independently selected from hydroxy, amino, halo, alkyl, haloalkyl, CN, alkoxy, haloalkoxy, alkylamino, aminoalkyl, —(CH$_2$)$_n$cycloalkyl, —(CH$_2$)$_n$heterocycloalkyl, —(CH$_2$)$_n$aryl, and —(CH$_2$)$_n$heteroaryl.

Therefore, what is intended is that "phenyl, naphthyl," replace aryl and "—CH$_2$-phenyl, —CH$_2$-naphthyl," replace arylalkyl within any definition of $R^1$ and $R^2$ presented in the embodiments herein without having to repeat all definitions of $R^1$ or $R^2$. Hence, it includes where $R^1$ or $R^2$ may be defined in any embodiment. For example, $R^1$ may be defined as H, C$_1$ to C$_6$ alkyl, aryl or arylalkyl such that it would mean $R^1$ is H, C$_1$ to C$_6$ alkyl, phenyl, naphthyl, —CH$_2$-phenyl or —CH$_2$-naphthyl. It also includes where $R^2$ may be defined as H, aryl or arylalkyl such that it would mean $R^2$ would be H, phenyl, naphthyl, —CH$_2$-phenyl or —CH$_2$-naphthyl. Furthermore, $R^1$ may be defined as C$_1$ to C$_6$ alkyl; C$_3$ to C$_6$ cycloalkyl, aryl, or arylalkyl and $R^2$ may be defined as H, C$_1$ to C$_6$ alkyl, C$_3$ to C$_6$ cycloalkyl, aryl or arylalkyl such that each aryl and arylalkyl within said definition is replaced "phenyl, naphthyl," and "—CH$_2$-phenyl, —CH$_2$-naphthyl", respectively.

Moreover, the explanation of aryl/arylalkyl within the definitions applies to other variables within the R groups of Formula I. For example, when referencing alkyl, all other definitions possible are included but not repeated when alkyl may be limited to, e.g., C$_1$ to C$_3$ alkyl. For brevity, the complete list of variables for the definition of the specific R group is not repeated.

Another embodiment of the present invention is a compound of Formula I, or a pharmaceutically acceptable salt thereof, wherein $R^3$ is H and each $R^4$ is H.

Another embodiment of the present invention is a compound of Formula IA or Formula IB:

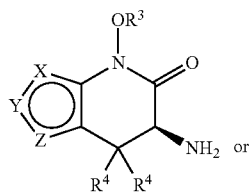

IA

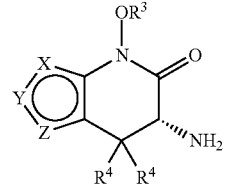

IB wherein X, Y, Z, $R^3$ and each $R^4$ are as defined herein for Formula I, including all embodiments discussed herein. When referring to a compound of Formula I, it is understood to also include a compound of Formula IA and IB without requiring specific reference.

In one embodiment, the invention also relates to each compound, individually, described in Examples 1 to 29 discussed herein (including the free bases or pharmaceutically acceptable salts thereof).

Another embodiment of the present invention is a method for or preparation of a medicament for the treatment or prevention in a mammal of a condition selected from the group consisting of acute neurological and psychiatric disorders; stroke; cerebral ischemia; spinal cord trauma; cognitive impairment, including mild cognitive impairment; head trauma; perinatal hypoxia; cardiac arrest; hypoglycemic neuronal damage; dementia; Alzheimer's disease; Huntington's Chorea; amyotrophic lateral sclerosis; ocular damage; retinopathy; cognitive disorders; idiopathic and drug-induced Parkinson's disease; muscular spasms and disorders associated with muscular spasticity including tremors; epilepsy; convulsions; migraine; urinary incontinence; substance tolerance; substance withdrawal; psychosis; schizophrenia; negative symptoms associated with schizophrenia; autism, including autism spectrum disorders; bipolar disorder; depression, including but not limited to Major Depressive Disorder and treatment-resistant depression; cognitive impairment associated with depression; cognitive impairment associated with cancer therapy; anxiety; mood disorders; inflammatory disorders; sepsis; cirrhosis; cancer and/or tumors associated with immune response escape; trigeminal neuralgia; hearing loss; tinnitus; macular degeneration of the eye; emesis; brain edema; pain; tardive dyskinesia; sleep disorders; attention deficit/hyperactivity disorder; attention deficit disorder; disorders that comprise as a symptom of deficiency in attention and/or cognition; and conduct disorder; comprising administering a compound selected from a compound of Formula I, IA, or IB.

Another embodiment of the present invention is a method for or preparation of a medicament for the treatment or prevention in a mammal of a condition selected from the group consisting of dementia; cognitive deficit symptoms of Alzheimer's disease; attention deficit symptoms of Alzheimer's disease; multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder (e.g., reading disorder, mathematics disorder, or a disorder of written expression); attention-deficit/hyperactivity disorder; age-related cognitive decline; cognitive deficits associated with psychoses; or cognitive deficits associated with schizophrenia, comprising administering a compound selected from a compound of Formula I, IA, or IB.

Another embodiment of the present invention is a method for or preparation of a medicament for the treatment or prevention in a mammal of a condition selected from the group consisting of acute neurological and psychiatric disorders; stroke; cerebral ischemia; spinal cord trauma; cognitive impairment, including mild cognitive impairment; head trauma; perinatal hypoxia; cardiac arrest; hypoglycemic neuronal damage; dementia; Alzheimer's disease; Huntington's Chorea; amyotrophic lateral sclerosis; ocular damage; retinopathy; cognitive disorders; idiopathic and drug-induced Parkinson's disease; muscular spasms and disorders associated with muscular spasticity including tremors; epilepsy; convulsions; migraine; urinary incontinence; substance tolerance; substance withdrawal; psychosis; schizophrenia; negative symptoms associated with schizophrenia; autism, including autism spectrum disorders; bipolar disorder; depression, including but not limited to Major Depressive Disorder and treatment-resistant depression; cognitive impairment associated with depression; cognitive impairment associated with cancer therapy; anxiety; mood disorders; inflammatory disorders; sepsis; cirrhosis; cancer and/or tumors associated with immune response escape; trigeminal neuralgia; hearing loss; tinnitus; macular degeneration of the eye; emesis; brain edema; pain; tardive dyskinesia; sleep disorders; attention deficit/hyperactivity disorder; attention deficit disorder; disorders that comprise as a symptom a deficiency in attention and/or cognition; and conduct disorder; comprising administering a compound of Formula I, IA, or IB.

Another embodiment of the present invention is a method for or preparation of a medicament for the treatment or prevention in a mammal of a condition selected from the group consisting of dementia; cognitive deficit symptoms of Alzheimer's disease; attention deficit symptoms of Alzheimer's disease; multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder (e.g., reading disorder, mathematics disorder, or a disorder of written expression); attention-deficit/hyperactivity disorder; age-related cognitive decline; cognitive deficits associated with psychoses; or cognitive deficits associated with schizophrenia, comprising administering a compound of Formula I, IA, or IB.

Another embodiment of the present invention is a compound of Formula I, IA, or IB wherein X—Y—Z and carbon atoms to which they are attached make a five-membered ring

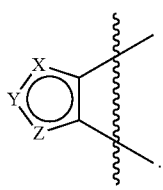

By using definitions of X, Y, and Z in Formula I, the following rings in Table A can be formed and fall within said definition:

TABLE A

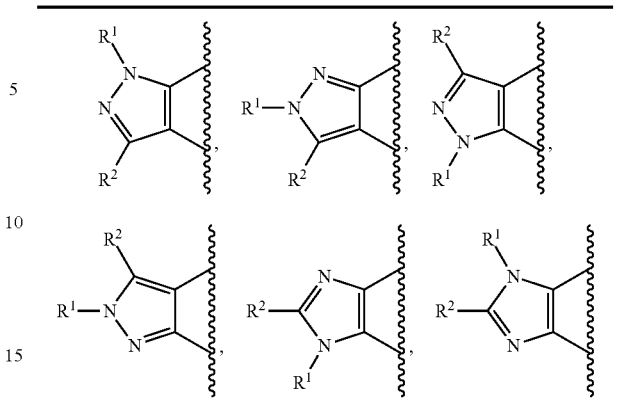

Another embodiment of the pending invention is where X—Y—Z and carbon atoms to which they are attached make any of the five-membered rings as provided in Table A; for example, the five-membered rings as provided in Table B:

TABLE B

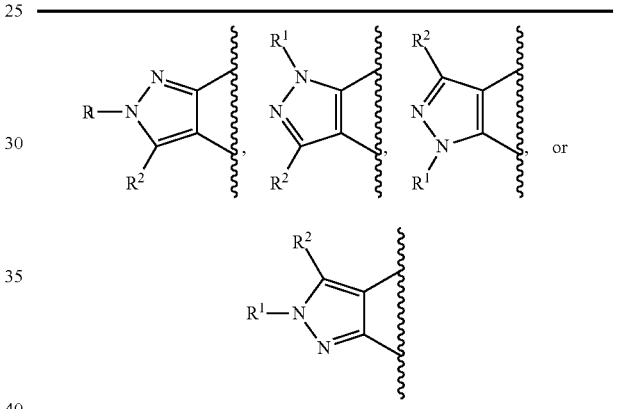

Compounds of Formula I or compounds related thereto when $R^3$ is H can form a Schiff base with pyridoxal-5-phosphate (also called PLP and/or vitamin B6) in the KAT II enzyme, to inhibit formation of kynurenic acid. Literature reports of other PLP-dependent enzymes (R. B. Silverman et al., J. Am. Chem. Soc. 1998, 120, 2256-2267) also demonstrate that an initially formed inhibitor-PLP Schiff base can undergo base-induced tautomerization to an isomeric ketimine, which can further isomerize to an aromatized inhibitor-PLP adduct. Another embodiment of the present invention is a Schiff base, or the product of base-promoted isomerization thereof, formed between a compound of Formula I, IA, or IB, as defined herein, and pyridoxal-5-phosphate.

Another embodiment of the present invention is a Schiff base, or the product of base-promoted isomerization thereof, formed between a compound of Formula I, IA, or IB, as defined herein, and pyridoxal-5-phosphate, wherein said Schiff base is formed in vivo.

Prodrugs that have little or no pharmacological activity themselves can, when administered into or onto the body, be converted into compounds of Formula I, IA, or IB having the desired activity. Such prodrugs are compounds of Formula I, IA, or IB when $R^3$ is other than H. For example, these compounds are where $R^3$ is

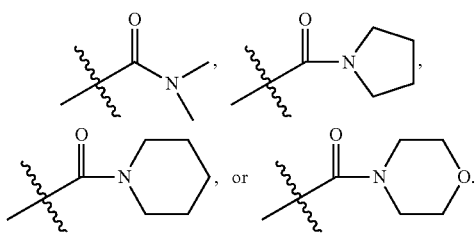

Abbreviations and Definitions

The term "alkyl" refers to a linear or branched-chain saturated hydrocarbyl substituent (i.e., a substituent obtained from a hydrocarbon by removal of a hydrogen) containing from one to twenty carbon atoms; in one embodiment from one to twelve carbon atoms; in another embodiment, from one to ten carbon atoms; in another embodiment, from one to six carbon atoms; and in another embodiment, from one to three carbon atoms. Examples of such substituents include methyl, ethyl, propyl (including n-propyl and isopropyl), butyl (including n-butyl, isobutyl, sec-butyl and tert-butyl), pentyl, isoamyl, hexyl and the like.

"Alkenyl" refers to an aliphatic hydrocarbon having at least one carbon-carbon double bond, including straight chain, branched chain or cyclic groups having at least one carbon-carbon double bond. In one embodiment, the alkenyl group has 2 to 20 carbon atoms (whenever a numerical range; e.g., "2-20", is stated herein, it means that the group, in this case the alkenyl group, may contain 2 carbon atoms, 3 carbon atoms, etc. up to and including 20 carbon atoms). In another embodiment, it is a medium size alkenyl having 2 to 10 carbon atoms. For example, as used herein, the term "$(C_2-C_6)$ alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 5 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. When the compounds of the invention contain a $(C_2-C_6)$alkenyl group, the compound may exist as the pure E (entgegen) form, the pure Z (zusammen) form, or any mixture thereof.

"Alkynyl" refers to an aliphatic hydrocarbon having at least one carbon-carbon triple bond, including straight chain, branched chain or cyclic groups having at least one carbon-carbon triple bond. In one embodiment, the alkynyl group has 2 to 20 carbon atoms (whenever a numerical range; e.g., "2-20", is stated herein, it means that the group, in this case the alkynyl group, may contain 2 carbon atoms, 3 carbon atoms, etc. up to and including 20 carbon atoms). In another embodiment, it is a medium size alkynyl having 2 to 10 carbon atoms. In another embodiment, it is a lower alkynyl having 2 to 6 carbon atoms. For example, as used herein, the term "$(C_2-C_6)$alkynyl" is used herein to mean straight or branched hydrocarbon chain alkynyl radical as defined above having 2 to 6 carbon atoms and one triple bond.

The term "cycloalkyl" refers to a carbocyclic substituent obtained by removing a hydrogen from a saturated carbocyclic molecule and having three to fourteen carbon atoms. In one embodiment, a cycloalkyl substituent has three to ten carbon atoms. Cycloalkyl may be a single ring, which typically contains from 3 to 6 ring atoms. Examples of cycloalkyl include cyclopropyl, cyclobutyl, cyclopentyl and cyclohexyl. Alternatively, cycloalkyl may be 2 or 3 rings fused together, such as bicyclo[4.2.0]octane and decalinyl.

The term "cycloalkyl" also includes substituents that are fused to a $C_6-C_{10}$ aromatic ring or to a 5-10-membered heteroaromatic ring, wherein a group having such a fused cycloalkyl group as a substituent is bound to a carbon atom of the cycloalkyl group. When such a fused cycloalkyl group is substituted with one or more substituents, the one or more substituents, unless otherwise specified, are each bound to a carbon atom of the cycloalkyl group. The fused $C_6-C_{10}$ aromatic ring or 5-10-membered heteroaromatic ring may be optionally substituted with halogen, $C_1-C_6$ alkyl, $C_3-C_{10}$ cycloalkyl, or =O.

The term "aryl" refers to an aromatic substituent containing one ring or two or three fused rings. The aryl substituent may have six to eighteen carbon atoms. As an example, the aryl substituent may have six to fourteen carbon atoms. The term "aryl" may refer to substituents such as phenyl, naphthyl and anthracenyl. The term "aryl" also includes substituents such as phenyl, naphthyl and anthracenyl that are fused to a $C_4-C_{10}$ carbocyclic ring, such as a $C_5$- or a $C_6$-carbocyclic ring, or to a 4-10-membered heterocyclic ring, wherein a group having such a fused aryl group as a substituent is bound to an aromatic carbon of the aryl group. When such a fused aryl group is substituted with one or more substituents, the one or more substituents, unless otherwise specified, are each bound to an aromatic carbon of the fused aryl group. The fused $C_4-C_{10}$ carbocyclic or 4-10-membered heterocyclic ring may be optionally substituted with halogen, $C_1-C_6$ alkyl, $C_3-C_{10}$ cycloalkyl, or =O. Examples of aryl groups include accordingly phenyl, naphthalenyl, tetrahydronaphthalenyl (also known as "tetralinyl"), indenyl, isoindenyl, indanyl, anthracenyl, phenanthrenyl, and benzonaphthenyl (also known as "phenalenyl").

The term "aralkyl" or "arylalkyl" refers to an alkyl substituent, as defined herein, substituted by an aryl substituent, as defined herein. Aralkyl substituents may have from seven to 24 carbon atoms. Examples of aralkyl groups include benzyl (i.e., phenylmethyl), phenylethyl, indenylmethyl, and naphthalenylethyl.

In some instances, the number of carbon atoms in a hydrocarbyl substituent (i.e., alkyl, alkenyl, cycloalkyl, cycloalkenyl, aryl, etc.) is indicated by the prefix "$C_x-C_y$," or "$C_{x-y}$," wherein x is the minimum and y is the maximum number of carbon atoms in the substituent. Thus, for example, "$C_1-C_6$ alkyl and "$C_{1-6}$ alkyl" both refer to an alkyl substituent containing from 1 to 6 carbon atoms. Illustrating further, $C_3-C_6$ cycloalkyl and $C_{3-6}$ cycloalkyl refer to saturated cycloalkyl containing from 3 to 6 carbon ring atoms.

In some instances, the number of atoms in a cyclic substituent containing one or more heteroatoms (i.e., heteroaryl or heterocycloalkyl) is indicated by the prefix "x-y-membered", wherein x is the minimum and y is the maximum number of atoms forming the cyclic moiety of the substituent. Thus, for example, 5-8-membered heterocycloalkyl refers to a heterocycloalkyl containing from 5 to 8 atoms, including one or more heteroatoms, in the cyclic moiety of the heterocycloalkyl.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents are attached include, for example, alcohols, enols and phenol.

The term "hydroxyalkyl" refers to an alkyl that is substituted with at least one hydroxy substituent. Examples of hydroxyalkyl include hydroxymethyl, hydroxyethyl, hydroxypropyl and hydroxybutyl.

The term "cyano" (also referred to as "nitrile") means CN.

The term "carbonyl" means C(O) or C=O.

The term "amino" refers to $NH_2$.

The term "alkylamino" refers to an amino group, wherein at least one alkyl chain is bonded to the amino nitrogen in place of a hydrogen atom. Examples of alkylamino substituents include monoalkylamino such as methylamino (exemplified by the formula $NH(CH_3)$), and dialkylamino such as dimethylamino (exemplified by the formula $—N(CH_3)_2$).

The term "halogen" refers to fluorine (which may be depicted as F), chlorine (which may be depicted as Cl), bromine (which may be depicted as Br), or iodine (which may be depicted as I). In one embodiment, the halogen is chlorine. In another embodiment, the halogen is fluorine. In another embodiment, the halogen is bromine.

The prefix "halo" indicates that the substituent to which the prefix is attached is substituted with one or more independently selected halogen substituents. For example, haloalkyl refers to an alkyl that is substituted with at least one halogen substituent. Where more than one hydrogen is replaced with halogens, the halogens may be identical or different. Examples of haloalkyls include chloromethyl, dichloromethyl, difluorochloromethyl, dichlorofluoromethyl, trichloromethyl, 1-bromoethyl, fluoromethyl, difluoromethyl, trifluoromethyl, 2,2,2-trifluoroethyl, difluoroethyl, pentafluoroethyl, difluoropropyl, dichloropropyl, and heptafluoropropyl. Illustrating further, "haloalkoxy" refers to an alkoxy that is substituted with at least one halogen substituent. Examples of haloalkoxy substituents include chloromethoxy, 1-bromoethoxy, fluoromethoxy, difluoromethoxy, trifluoromethoxy (also known as "perfluoromethyloxy"), and 2,2,2-trifluoroethoxy. It should be recognized that if a substituent is substituted by more than one halogen substituent, those halogen substituents may be identical or different (unless otherwise stated).

The term "oxo" refers to =O.

The term "alkoxy" refers to an alkyl linked to an oxygen, which may also be represented as —OR, wherein the R represents the alkyl group. Examples of alkoxy include methoxy, ethoxy, propoxy and butoxy.

The term "cycloalkyloxy" refers to a cycloalkyl linked to an oxygen, which may also be represented as —OR, wherein the R represents the cycloalkyl group. Examples of cycloalkyloxy include cyclopropyloxy, cyclobutyloxy, and cyclopentyloxy.

The term "heterocycloalkyl" refers to a substituent obtained by removing a hydrogen from a saturated or partially saturated ring structure containing a total of 4 to 14 ring atoms. At least one of the ring atoms is a heteroatom usually selected from oxygen, nitrogen, or sulfur. A heterocycloalkyl alternatively may comprise 2 or 3 rings fused together, wherein at least one such ring contains a heteroatom as a ring atom (i.e., nitrogen, oxygen, or sulfur). In a group that has a heterocycloalkyl substituent, the ring atom of the heterocycloalkyl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heterocycloalkyl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom.

The term "heterocycloalkyl" also includes substituents that are fused to a $C_6$-$C_{10}$ aromatic ring or to a 5-10-membered heteroaromatic ring, wherein a group having such a fused heterocycloalkyl group as a substituent is bound to a heteroatom of the heterocycloalkyl group or to a carbon atom of the heterocycloalkyl group. When such a fused heterocycloalkyl group is substituted with one or more substituents, the one or more substituents, unless otherwise specified, are each bound to a heteroatom of the heterocycloalkyl group or to a carbon atom of the heterocycloalkyl group. The fused $C_6$-$C_{10}$ aromatic ring or 5-10-membered heteroaromatic ring may be optionally substituted with halogen, $C_1$-$C_6$ alkyl, $C_3$-$C_{10}$ cycloalkyl, $C_1$-$C_6$ alkoxy, or =O.

The term "heterocycloalkyloxy" refers to a heterocycloalkyl linked to an oxygen, which may also be represented as —OR, wherein the R represents the heterocycloalkyl group. Examples of heterocycloalkyloxy include oxetanyloxy (such as oxetan-3-yloxy), tetrahydrofuranyloxy (such as tetrahydrofuran-3-yloxy), and tetrahydropyranyloxy (such as tetrahydro-2H-pyran-4-yloxy or tetrahydro-2H-pyran-3-yloxy).

The term "heteroaryl" refers to an aromatic ring structure containing from 5 to 14 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A heteroaryl may be a single ring or 2 or 3 fused rings.

Examples of heteroaryl substituents include 6-membered ring substituents such as pyridyl, pyrazyl, pyrimidinyl, and pyridazinyl; 5-membered ring substituents such as triazolyl, imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6-/5-membered fused ring substituents such as benzothiofuranyl, isobenzothiofuranyl, benzisoxazolyl, benzoxazolyl and purinyl; and 6-/6-membered fused rings such as quinolinyl, isoquinolinyl, cinnolinyl, quinazolinyl, and 1,4-benzoxazinyl.

In a group that has a heteroaryl substituent, the ring atom of the heteroaryl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom. The term "heteroaryl" also includes pyridyl N-oxides and groups containing a pyridine N-oxide ring.

Examples of single ring heteroaryls include furanyl, thiophenyl (also known as "thiofuranyl"), pyrrolyl, imidazolyl, pyrazolyl, triazolyl, tetrazolyl, oxazolyl, isoxazolyl, thiazolyl, isothiazolyl, thiadiazolyl, oxadiazolyl [including 1,2,4-oxadiazolyl (also known as "azoximyl"), 1,2,5-oxadiazolyl (also known as "furazanyl"), or 1,3,4-oxadiazolyl], oxatriazolyl (including 1,2,3,4-oxatriazolyl or 1,2,3,5-oxatriazolyl), pyridinyl (also known as "azinyl"), diazinyl [including pyridazinyl (also known as "1,2-diazinyl"), pyrimidinyl (also known as "1,3-diazinyl" or "pyrimidyl"), or pyrazinyl (also known as "1,4-diazinyl")], and triazinyl [including s-triazinyl (also known as "1,3,5-triazinyl"), as-triazinyl (also known 1,2,4-triazinyl), and v-triazinyl (also known as "1,2,3-triazinyl")].

Examples of 2-fused-ring heteroaryls include indolizinyl, pyrindinyl, purinyl, naphthyridinyl, pyridopyridinyl (including pyrido[3,4-b]-pyridinyl, pyrido[3,2-b]pyridinyl, or pyrido[4,3-b]pyridinyl), and pteridinyl, indolyl, isoindolyl, isoindazolyl, phthalazinyl, quinoxalinyl, quinazolinyl, benzoxazolyl, indoxazinyl, anthranilyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, and benzisoxazinyl.

Examples of 3-fused-ring heteroaryls or heterocycloalkyls include 5,6-dihydro-4H-imidazo[4,5,1-ij]quinoline, 4,5-dihydroimidazo[4,5,1-hi]indole, 4,5,6,7-tetrahydroimidazo[4,5,1-jk][1]benzazepine, and dibenzofuranyl.

Other examples of fused ring heteroaryls include benzo-fused heteroaryls such as indolyl, isoindolyl (also known as "isobenzazolyl" or "pseudoisoindolyl"), benzazinyl [including quinolinyl (also known as "1-benzazinyl") or isoquinolinyl (also known as "2-benzazinyl")], phthalazinyl, quinoxalinyl, quinazolinyl, benzodiazinyl [including cinnolinyl (also known as "1,2-benzodiazinyl") or quinazolinyl (also known as "1,3-benzodiazinyl")], benzoxazolyl, indoxazinyl (also known as "benzisoxazolyl"), benzoxadiazolyl, benzofuranyl (also known as "coumaronyl"), isobenzofuranyl, benzothienyl (also known as "benzothiophenyl," "thionaphthenyl," or "benzothiofuranyl"), isobenzothienyl (also known as "isobenzothiophenyl," "isothianaphthenyl," or "isobenzothiofuranyl"), benzothiazolyl, benzothiadiazolyl, benzimidazolyl, benzotriazolyl, benzoxazinyl, benzisoxazinyl (including 1,2-benzisoxazinyl or 1,4-benzisoxazinyl), carbazolyl, and acridinyl.

The term "heteroaryl" also includes substituents such as pyridyl and quinolinyl that are fused to a $C_4$-$C_{10}$ carbocyclic ring, such as a $C_5$ or a $C_6$ carbocyclic ring, or to a 4-10-membered heterocyclic ring, wherein a group having such a fused aryl group as a substituent is bound to an aromatic carbon of the heteroaryl group or to a heteroatom of the heteroaryl group. When such a fused heteroaryl group is substituted with one or more substituents, the one or more substituents, unless otherwise specified, are each bound to an aromatic carbon of the heteroaryl group or to a heteroatom of the heteroaryl group. The fused $C_4$-$C_{10}$ carbocyclic or 4-10-membered heterocyclic ring may be optionally substituted with halogen, $C_1$-$C_6$ alkyl, $C_3$-$C_{10}$ cycloalkyl, or =O.

Additional examples of heteroaryls and heterocycloalkyls include: 3-1H-benzimidazol-2-one, (1-substituted)-2-oxobenzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, 2H-imidazol-2-one, 1-phthalimidinyl, benzoxanyl, benzo[1,3]dioxine, benzo[1,4]dioxine, benzopyrrolidinyl, benzopiperidinyl, benzoxolanyl, benzothiolanyl, 4,5,6,7-tetrahydropyrazol[1,5-a]pyridine, benzothianyl, pyrrolidinyl, dihydrofuranyl, tetrahydrothienyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-2-yl (C-attached).

If a substituent is described as being "substituted," a non-hydrogen substituent is in the place of a hydrogen attached to a carbon, oxygen, sulfur or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a substituent is described such that it "may be substituted" or "optionally substituted," the substituent may be either substituted or not substituted. If a carbon of a substituent is described such that it may be substituted or is optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent. One exemplary substituent may be depicted as —NR'R", wherein R' and R" together with the nitrogen atom to which they are attached, may form a heterocyclic ring. The heterocyclic ring formed from R' and R" together with the nitrogen atom to which they are attached may be partially or fully saturated. In one embodiment, the heterocyclic ring consists of 4 to 7 atoms. In another embodiment, the heterocyclic ring is selected from the group consisting of azepinyl, piperidinyl, pyrrolidinyl, morpholino, thiomorpholino, piperazinyl, and azetidinyl.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. To illustrate, tetrazolyl (which has only one substitutable position) would be optionally substituted with up to one non-hydrogen substituent. To illustrate further, if an amino nitrogen is described as being optionally substituted with up to 2 non-hydrogen substituents, then the nitrogen will be optionally substituted with up to 2 non-hydrogen substituents if the amino nitrogen is a primary nitrogen, whereas the amino nitrogen will be optionally substituted with up to only 1 non-hydrogen substituent if the amino nitrogen is a secondary nitrogen.

A prefix attached to a multi-moiety substituent only applies to the first moiety. To illustrate, the term "alkylcycloalkyl" contains two moieties: alkyl and cycloalkyl. Thus, a $C_1$-$C_6$ prefix on $C_1$-$C_6$ alkylcycloalkyl means that the alkyl moiety of the alkylcycloalkyl contains from 1 to 6 carbon atoms; the $C_1$-$C_6$ prefix does not describe the cycloalkyl moiety. To illustrate further, the prefix "halo" on haloalkoxyalkyl indicates that only the alkoxy moiety of the alkoxyalkyl substituent is substituted with one or more halogen substituents. If the halogen substitution only occurs on the alkyl moiety, the substituent would be described as "alkoxyhaloalkyl." If the halogen substitution occurs on both the alkyl moiety and the alkoxy moiety, the substituent would be described as "haloalkoxyhaloalkyl."

If substituents are described as being "independently selected" from a group, each substituent is selected independent of the other. Each substituent therefore may be identical to or different from the other substituent(s).

As used herein the term "Formula I" may be referred to as "a compound of the invention" or as "compounds of the invention." Such terms are also defined to include all forms of the compound of Formula I, including hydrates, solvates, isomers, crystalline and non-crystalline forms, isomorphs, polymorphs, and metabolites thereof.

The following abbreviations are used herein:
brine: saturated aqueous sodium chloride solution
DCC: 1,3-dicyclohexylcarbodiimide
EDCI: 1-[3-(dimethylamino)propyl]-3-ethylcarbodiimide hydrochloride
EtOAc: ethyl acetate
HBTU: O-benzotriazol-1-yl-N,N,N',N'-tetramethyluronium hexafluorophosphate
HMBC: heteronuclear multiple bond correlation
min: minutes
NOE: nuclear Overhauser effect
psi: pounds per square inch
RT: room temperature
SEM: [2-(trimethylsilyl)ethoxy]methyl Isomers When an asymmetric center is present in a compound of Formula I, hereinafter referred to as the compound of the invention, the compound may exist in the form of optical isomers (enantiomers). In one embodiment, the present invention comprises enantiomers and mixtures, including racemic mixtures of the compounds of Formula I. In another embodiment, for compounds of Formula I that contain more than one asymmetric center, the present invention comprises diastereomeric forms (individual diastereomers and mixtures thereof) of compounds. When a compound of Formula I contains an alkenyl group or moiety, geometric isomers may arise.

Tautomeric Forms

The present invention comprises the tautomeric forms of compounds of Formula I. Where structural isomers are interconvertible via a low energy barrier, tautomeric isomerism ('tautomerism') can occur. This can take the form of proton tautomerism in compounds of Formula I containing, for example, an imino, keto, or oxime group, or so-called valence tautomerism in compounds which contain an aromatic moiety. It follows that a single compound may exhibit more than one type of isomerism. The various ratios of the tautomers in solid and liquid form is dependent on the various substituents on the molecule as well as the particular crystallization technique used to isolate a compound.

Salts

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sulfanilate, cyclohexylaminosulfonate, β-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diethanolamine, glycine, lysine, meglumine, ethanolamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (i.e., dimethyl, diethyl, dibutyl, and diamyl sulfates), long chain halides (i.e., decyl, lauryl, myristyl, and stearyl chlorides, bromides, and iodides), arylalkyl halides (i.e., benzyl and phenethyl bromides), and others.

In one embodiment, hemisalts of acids and bases may also be formed, for example, hemisulphate and hemicalcium salts.

Isotopes

The present invention also includes isotopically labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2$H, $^3$H, $^{13}$C, $^{11}$C, $^{14}$C, $^{15}$N, $^{18}$O, $^{17}$O, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of Formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

The invention also relates to prodrugs of the compounds of Formula I. Thus certain derivatives of compounds of Formula I which may have little or no pharmacological activity themselves can, when administered into or onto the body, be converted into compounds of Formula I having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985).

Some non-limiting examples of prodrugs in accordance with the invention include:

(i) where the compound of Formula I contains a carboxylic acid functionality which is functionalized into a suitably metabolically labile group (esters, carbamates, etc.) on the compound of Formula I;

(ii) where the compound of Formula I contains an alcohol functionality which is functionalized into a suitably metabolically labile group (esters, carbonates, carbamates, acetals, ketals, etc.) on the compound of Formula I; and (iii) where the compound of Formula I contains a primary or secondary amino functionality, or an amide which is functionalized into a suitably metabolically labile group, e.g., a hydrolyzable group (amides, carbamates, ureas, etc.) on the compound of Formula I.

Further examples of replacement groups in accordance with the foregoing examples and examples of other prodrug types may be found in the aforementioned references.

Moreover, certain compounds of Formula I may themselves act as prodrugs of other compounds of Formula I.

Administration and Dosing

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The compounds of the invention may be administered orally. Oral administration may involve swallowing, so that the compound enters the gastrointestinal tract, or buccal or sublingual administration may be employed by which the compound enters the bloodstream directly from the mouth.

In another embodiment, the compounds of the invention may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

Use in the Preparation of a Medicament

In another embodiment, the invention comprises the use of one or more compounds of the invention for the preparation of a medicament for the treatment of the conditions recited herein.

Pharmaceutical Compositions

For the treatment of the conditions referred to herein, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (i.e., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, B. C. Finnin and T. M. Morgan, *J. Pharm. Sci.*, vol. 88, pp. 955-958, 1999.

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed-linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients (3rd Ed.), American Pharmaceutical Association, Washington, 1999.

Co-administration

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially. An exemplary therapeutic agent may be, for example, a metabotropic glutamate receptor agonist.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

In one embodiment, the compounds of this invention are administered as adjunctive therapy with known anti-psychotics such as Ziprasidone (Geodon), Clozapine, Molindone, Loxapine, Pimozide, Risperidone, Olanzapine, Remoxipride, Sertindole, Amisulpride, Quetiapine, Prochlorperazine, Fluphenazine, Trifluoperazine, Thioridazine, Haloperidol, Chlorpromazine, Flupentixol and Pipotiazine.

In another embodiment, the compounds of the present invention may also be used in combination with CNS agents such as antidepressants (such as sertraline), anti-Parkinsonian drugs (such as deprenyl, L-dopa, Requip, Mirapex, MAOB inhibitors such as selegiline and rasagiline, COMT inhibitors such as Tasmar, A-2 inhibitors, dopamine reuptake inhibitors, NMDA antagonists, nicotine agonists, dopamine agonists and inhibitors of neuronal nitric oxide synthase), anti-Alzheimer's drugs such as donepezil, tacrine, alpha2delta inhibitors, COX-2 inhibitors, gaba pentenoids, propentofylline or metrifonate, and antipyschotics such as PDE10 inhibitors, 5HT2C agonists, alpha 7 nicotinic receptor agonists, CB1 antagonists and compounds having activity antagonizing dopamine D2 receptors.

Kits

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

In another embodiment, the invention relates to the novel intermediates useful for preparing the compounds of the invention.

The compounds of Formula I may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

Scheme 1

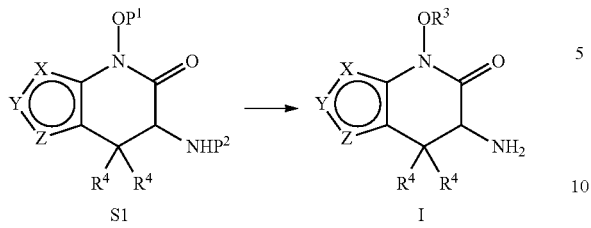

Scheme 1 refers to the preparation of compounds of Formula I, wherein $R^3$ is H. Referring to Scheme 1, the compound of Formula I can be prepared from the compound of Formula S1 through removal of the two optionally present protecting groups $P^1$ and $P^2$. $P^1$ and $P^2$ in this case refer to groups well known to those skilled in the art for hydroxyl and amine protection. For example, $P^1$ may be a benzyl group (Bn), which can be cleaved via hydrogenation over a catalyst such as palladium, or through treatment with boron tribromide. $P^2$ may advantageously be a tert-butoxycarbonyl group (Boc), which is normally removed through treatment with either HCl or trifluoroacetic acid, or a benzyloxycarbonyl group (CBZ), which may be cleaved using hydrogenation over a catalyst such as palladium.

Scheme 2 refers to the preparation of compounds S1 wherein $P^1$ is H and $P^2$ is Boc. Carboxylic acid S2 is converted to 2,2,2-trifluoroethyl ester S3 using 2,2,2-trifluoroethanol and a coupling reagent such as DCC, EDCI, or HBTU. 2,2,2-Trifluoroethyl ester S3 can also be synthesized from S2 using 2,2,2-trifluoroethyl trifluoromethanesulfonate in the presence of a base such as triethylamine, in a modification of the procedures described by T. Kubota et al., *J. Org. Chem.* 1980, 45, 5052-5057; and F. J. Lopez et al., *Bioorg. Med. Chem. Lett.* 2003, 13, 1873-1878. Cyclic hydroxamic acid S1 is generated by reductive cyclization of S3 performed under hydrogenation conditions using catalysts such as Pt/C or Pt(S), through an adaptation of the work of T. J. McCord et al., *J. Heterocycl. Chem.* 1972, 9, 119. A commonly observed side reaction is over-reduction to the aniline, which generates a lactam side product; this can be removed by column chromatography. S1 can be converted into a compound of Formula I according to the methods of Scheme 1.

Scheme 2

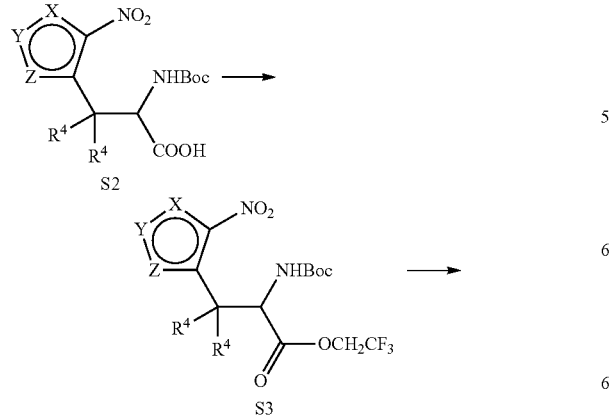

Scheme 3 refers to the preparation of compound S7 (one enantiomer of S2 wherein each $R^4$ is H). Bromomethyl heteroaryl compound S4 can be reacted stereoselectively with tert-butyl N-(diphenylmethylene)glycinate, using a chiral catalyst under basic conditions, such as cesium hydroxide, to provide the protected amino acid derivative S5. This enantioselective route is based on the work of S. Kumar and U. Ramachandran, *Tetrahedron: Asymmetry* 2003, 14, 2539-2545; and E. J. Corey et al., *J. Am. Chem. Soc.* 1997, 119, 12414-12415. Amino acid deprotection is carried out under acidic conditions, for instance using aqueous HCl, to give the free amino acid S6. Introduction of a Boc group onto the amine yields acid S7, which can be converted into a compound of Formula I according to the methods of Schemes 2 and 1. One skilled in the art will understand that for all of the stereoselective chemistry herein described, similar methods may be used to prepare the opposite enantiomer of the compounds shown, or the racemate thereof.

Scheme 3

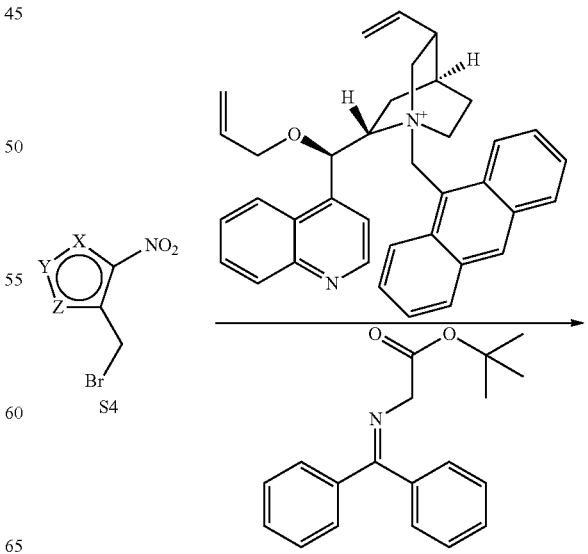

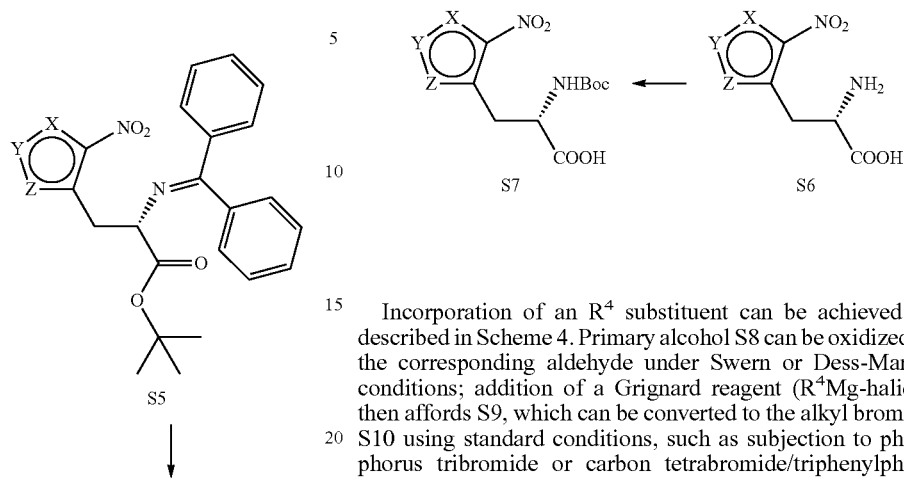

Incorporation of an $R^4$ substituent can be achieved as described in Scheme 4. Primary alcohol S8 can be oxidized to the corresponding aldehyde under Swern or Dess-Martin conditions; addition of a Grignard reagent ($R^4$Mg-halide) then affords S9, which can be converted to the alkyl bromide S10 using standard conditions, such as subjection to phosphorus tribromide or carbon tetrabromide/triphenylphosphine. Diasteroselective phase-transfer-catalyzed alkylation of S10 with a glycinate Schiff base (see T. Ooi et al., *Org. Lett.* 2007, 9, 3945-3948) then affords S11. S11 may be converted into a compound of Formula I according to the methods of Schemes 3, 2 and 1.

Scheme 4

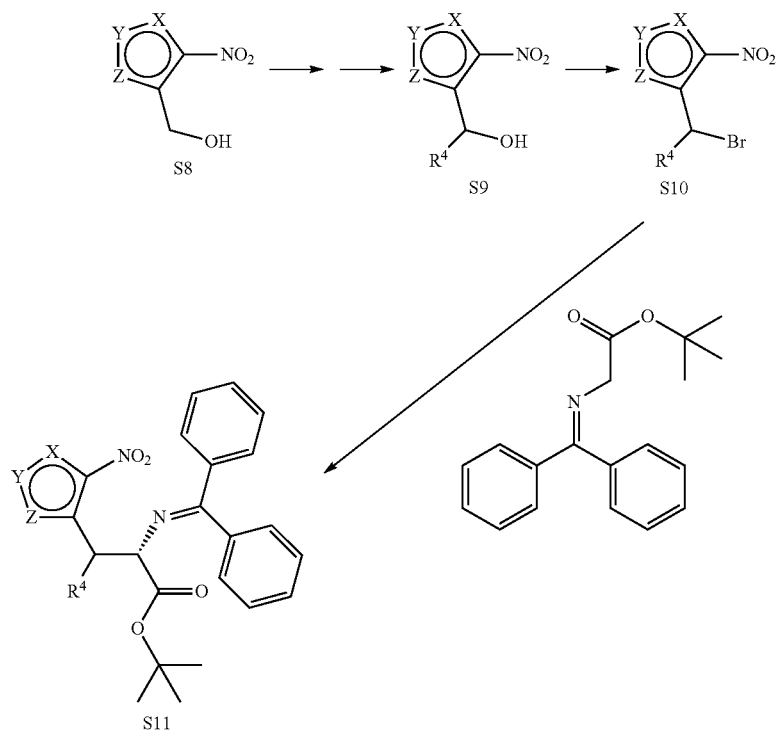

Alternatively, a Strecker synthesis can be employed, as depicted in Scheme 5. Bromomethyl heteroaryl S4 is converted to the corresponding nitrile through reaction with cyanide ion, then alkylated under basic conditions with $R^4$—Br to provide S13. Conversion of the nitrile of S13 to aldehyde S14 is effected under standard conditions, for example through reaction with diisobutylaluminum hydride. Asymmetric Strecker synthesis of S14 (see M. Shibasaki et al., *Org. Reactions* 2008, 70, 1-119) then affords the amino nitrile S15, which is transformed to a compound of formula S2 by introduction of a Boc group and hydrolysis of the nitrile to the carboxylic acid. One skilled in the art will recognize that this approach can also be used to introduce a fluoromethyl group for $R^4$ by reaction of the anion of S12 with formaldehyde, followed by conversion of the resulting alcohol to a fluoro group via conversion to a leaving group such as tosylate, followed by displacement with fluoride ion. Compound S2 may be converted into a compound of Formula I according to the methods of Schemes 2 and 1.

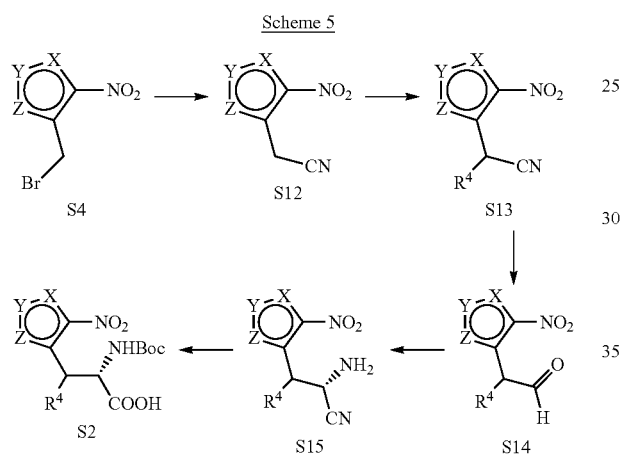

Scheme 5

Scheme 6 refers to the preparation of bromomethyl nitro heteroaryl S4. o-Nitro-ester heteroaromatic compound S16 in which at least one $R^1$ is H undergoes N-alkylation or N-arylation to give derivatives S17 wherein $R^1$ is alkyl or aryl (see Scheme 7 for the more specific case wherein the heteroaryl group is a pyrazole; R" in Scheme 7 is methyl or ethyl). Introduction of an alkyl group may be carried out with various alkyl or substituted alkyl bromide derivatives under standard basic conditions. Arylation can be carried out using Chan-Lam copper-mediated coupling with arylboronic or heteroarylboronic acids, as described in *Tetrahedron* 2009, 65, 3529-3535 and WO 2007/055941. In both cases the assignment of the regioisomers obtained (for instance, S19, S20, S22, and S23 in Scheme 7) may be carried out using advanced NMR experiments such as NOE and HMBC. It will be noted by one skilled in the art that such N-alkylation and N-arylation reactions may also be carried out on other intermediates, such as but not limited to S29, S30 or S32; in such cases it may be advantageous to temporarily protect the heteroaryl nitrogen in question as, for example, its tert-butoxycarbonyl derivative, while carrying out earlier steps in the synthesis. If selective removal of this Boc group is required, in the case where more than one Boc is present, the basic method of S. E. Kazzouli et al., *Tetrahedron Lett.* 2006, 47, 8575-8577 may be employed.

The resulting intermediate S17 can then be reduced using standard conditions such as lithium aluminum hydride, lithium borohydride or sodium borohydride in methanol, giving the corresponding alcohol S8, as shown in Scheme 6. Alternatively, the ester S17 can be hydrolyzed to the corresponding carboxylic acid and reduced to the alcohol S8 using borane in tetrahydrofuran. Alcohol S8 is converted to bromide S4 according to standard procedures, for example with phosphorus tribromide, as described by R. M. Rzasa et al., *Bioorg. Med. Chem.* 2007, 15, 6574-6595, or by using carbon tetrabromide and triphenylphosphine. Bromide S4 can be converted into a compound of Formula I using the methods of Schemes 5, 3, 2 and 1, while alcohol S8 may be converted to Formula I according to Schemes 4, 2 and 1.

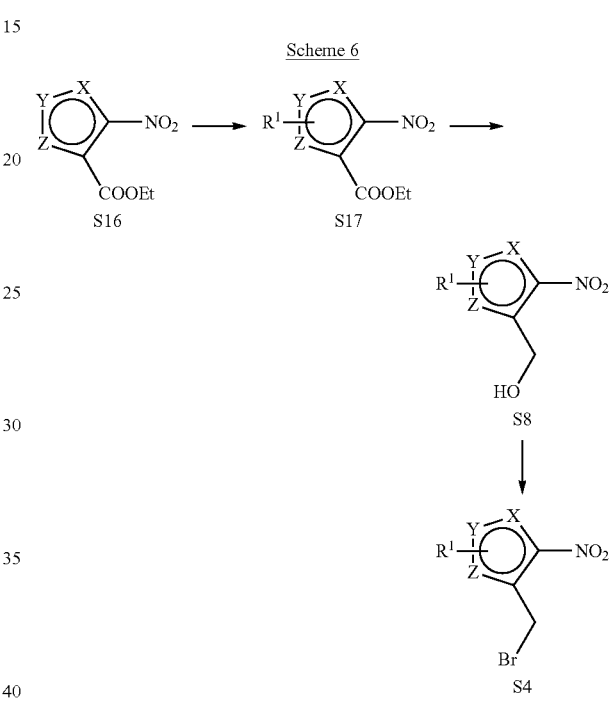

Scheme 6

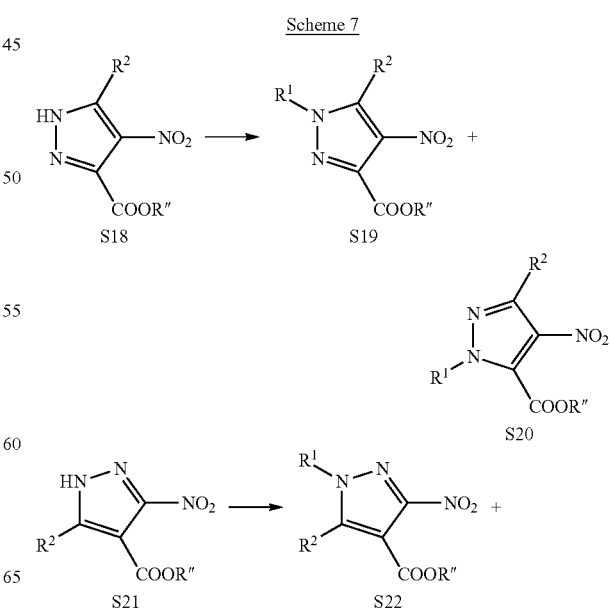

Scheme 7

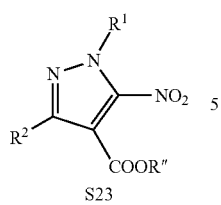

S23

Scheme 8 depicts several methods of preparation for key ester intermediate S16. Nitration of 5-membered heteroaryl compound S24 affords nitro compound S25. Oxidation of the methyl group, as described in WO 2006/046135 and U.S. Pat. No. 4,282,361, gives the corresponding carboxylic acid S26, which may be converted to ester S16 via Fischer esterification. When carboxylic acid S27 is available, compound S26 may be directly obtained by nitration. In cases where the required aminoheteroaryl ester S28 is commercially available or known in the literature, it can be oxidized to afford nitro heteroaryl S16 with sodium perborate in glacial acetic acid or in trifluoroacetic acid, using a modified version of the procedure described in US 2006/0009509. The oxidation reaction can also be performed with $Zr(Ot-Bu)_4$/tert-butylhydroperoxide, in a modification of the procedures described in *Eur. J. Org. Chem.* 1998, 679-682; *J. Prakt. Chem.* 1997, 339, 335-339; and *Advanced Synthesis and Catalysis* 2009, 351, 93-96. Ester S16 can be converted into a compound of Formula I using the methods of Schemes 6, 3, 2 and 1.

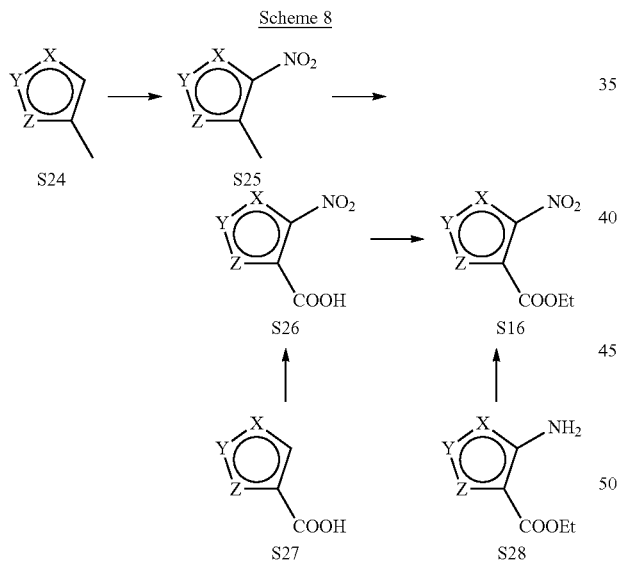

An alternate approach to heteroaryl acid S7 is shown in Scheme 9. Bromo nitro heteroaryl compound S29 (generally available either via bromination of the corresponding nitro heteroaryl using bromine or N-bromosuccinimide, or via bromination of a heteroaryl followed by nitration; alternatively, a Hunsdiecker reaction can be carried out on the corresponding carboxylic acid derived from hydrolysis of S16 or S17) can be subjected to a Negishi coupling with an appropriately protected iodoalanine derivative to provide S30 (see R. F. W. Jackson et al., *J. Org. Chem.* 2010, 75, 245-248). Subsequent ester hydrolysis, for example under standard saponification conditions, affords acid S7. In the specific case of a pyrazole, nitropyrazoles are available via the nitro rearrangement chemistry described by J. W. A. M. Janssen et al., *J. Org. Chem.* 1973, 38, 1777-1782. S7 can be converted into a compound of Formula I according to the methods of Schemes 2 and 1.

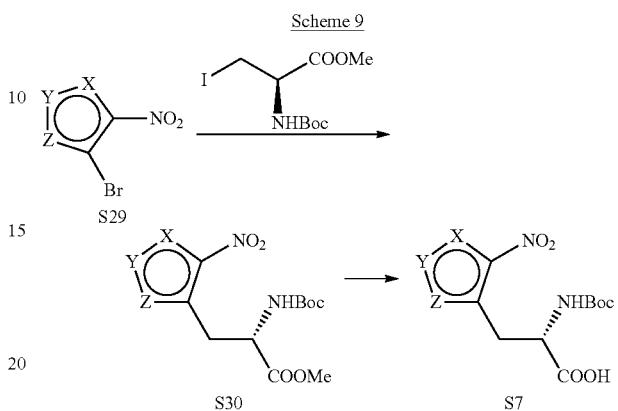

In certain cases, as shown in Scheme 10, a palladium-catalyzed Suzuki reaction is a suitable alternative to the Negishi reaction for installing the amino acid, through reaction of bromo compound S29 with a boronate such as [(2S)-2-[(tert-butoxycarbonyl)amino]-3-{[2-(trimethylsilyl)ethoxy]methoxy}propyl]boronic acid (S31) (C. W. Barfoot et al., *Tetrahedron* 2005, 61, 3403-3417). The resulting derivative S32 can be deprotected via removal of the SEM protecting group, then oxidized to carboxylic acid S7 using the general chemistry described by Barfoot et al. S7 may be converted into a compound of Formula I according to the methods of Schemes 2 and 1.

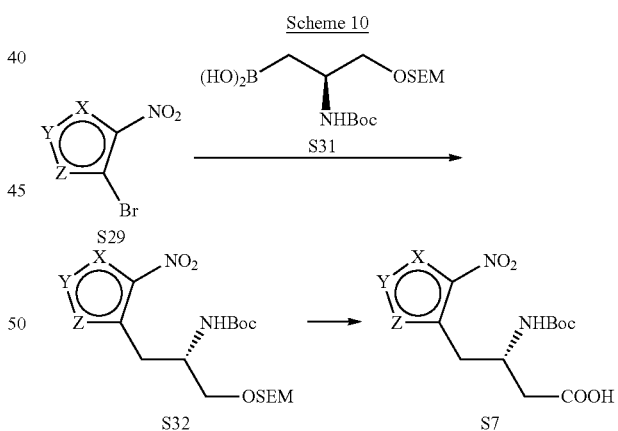

Scheme 11 refers to the preparation of substituted pyrazoles of the general formula S29 (e.g., S34). A 4-bromopyrazole S33 can undergo step-wise nitration and N-alkylation (see *J. Chem. Soc., Perkin Trans I* 1984, 63-67) to provide 4-bromo-5-nitropyrazole S34. Alternatively, a 5-amino-4-bromopyrazole S36 can be subjected to oxidation as outlined in Scheme 8, to provide S34. Alternatively, Hunsdiecker reaction of 4-carboxy-pyrazole S35 affords 4-bromo-5-nitropyrazole S34. Pyrazole S34 can be converted into S37, which represents a subset of the compounds of Formula I, using the methods of Schemes 9 or 10, followed by Schemes 2 and 1.

Scheme 11

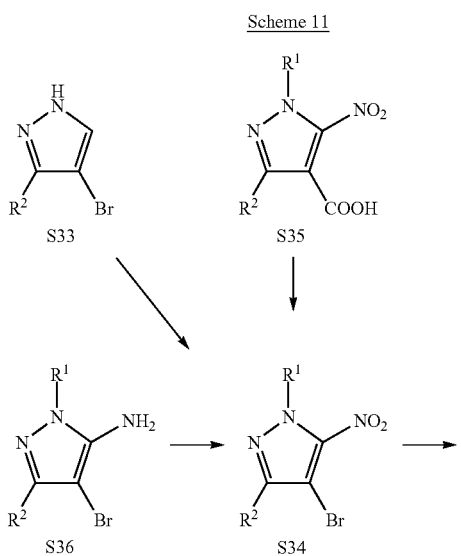

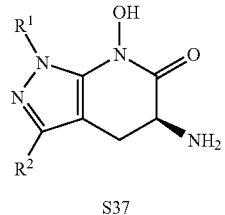

S37

Nitro compounds of the general formula S29 can also be prepared through oxidation of the corresponding amine S38 as shown in Scheme 12, using chemistry described for conversion of S28 to S16 in Scheme 8. An alternative approach to amine oxidation involves initial derivatization of the amino group of S38 as its benzaldehyde imine S39, followed by meta-chloroperoxybenzoic acid oxidation to provide the oxaziridine S40. Acid-catalyzed isomerization to nitrone S41, as described by Y-M. Lin and M. J. Miller, *J. Org. Chem.* 1999, 64, 7451-7458, is followed by Negishi cross-coupling to provide protected amino acid S42. Acid-mediated hydrolysis of the benzylidene group, as described by Lin and Miller, and ester hydrolysis, followed by amide coupling of the liberated hydroxylamine to the carboxylic acid group, affords S43, which represents a subset of the compounds of Formula I.

Scheme 12

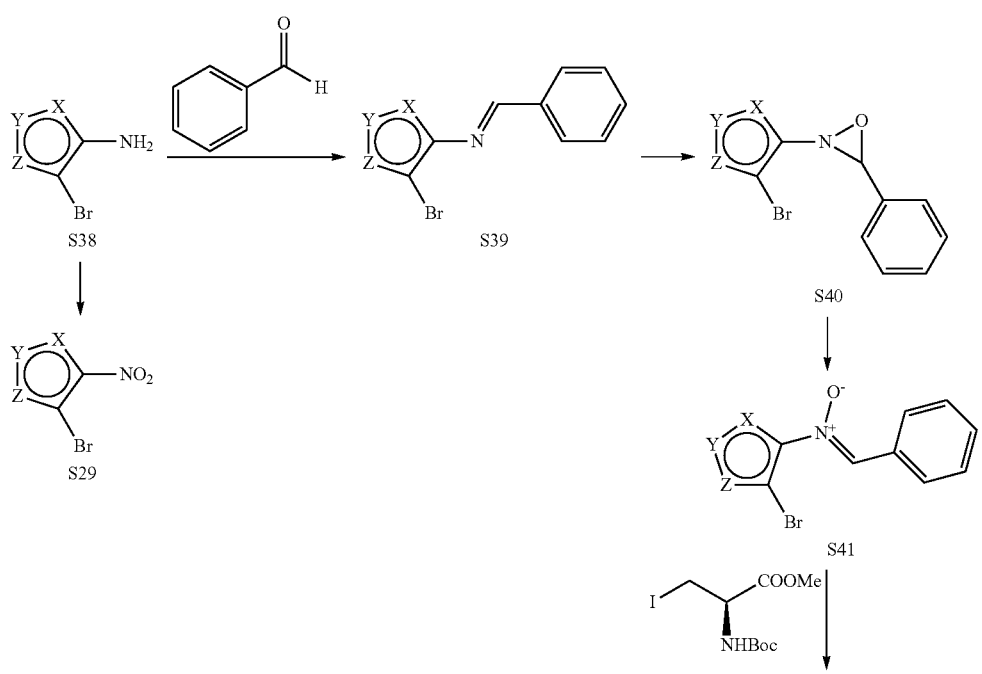

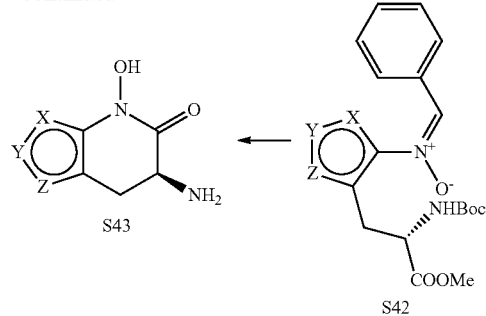

In cases where the nitro-substituted heteroaryl compound S29 is difficult to obtain, an alternate bond formation can be used to generate the compounds of Formula I, as depicted in Scheme 13. Negishi reaction of bromo heteroaryl compound S44 to provide protected amino acid S45 wherein R″ is methyl or ethyl, as described in Scheme 9, is followed by hydrolysis to the carboxylic acid and conversion to amide S46 through coupling with an O-protected hydroxylamine derivative. The resulting amide, upon treatment with phenyliodine (III) bis(trifluoroacetate) (PIFA) then undergoes a nitrenium ion cyclization reaction to afford S47, using the method of A. Correa et al., Tetrahedron 2003, 59, 7103-7110. One skilled in the art will recognize that where one of X, Y or Z in the heteroaryl ring of S47 is CH, installation of $R^2$ can be effected at this stage through either palladium-mediated C—H activation chemistry (see I. V. Seregin and V. Gevorgyan, Chem. Soc. Rev. 2007, 36, 1173-1193), or through bromination followed by a palladium-catalyzed cross-coupling reaction. Compound S47 may be converted into a compound of Formula I according to Scheme 1.

nitrile with an alkyl or aryl acid chloride gives enol intermediate S48. S48 can be converted to the corresponding vinyl chloride or alkyl vinyl ether S49 under standard conditions (e.g., treatment with phosphorus oxychloride or reaction with methyl or ethyl iodide in the presence of silver carbonate); in cases in which the vinyl chloride is particularly unstable, the alkyl vinyl ether may provide a more stable alternative. Intermediate S49 can be selectively converted to pyrazole S50 via condensation with the appropriate hydrazine. The regioisomer S51 can be obtained via condensation of S49 with the preformed hydrazone derived from benzaldehyde, as described by Y. Xia et al., J. Med. Chem. 1997, 40, 4372-4377. Oxidation of either S50 or S51 to the corresponding nitro compound can be effected as described in Scheme 8; the nitro compound can then be converted into a compound of Formula I using the methods of Schemes 6, 3, 2 and 1.

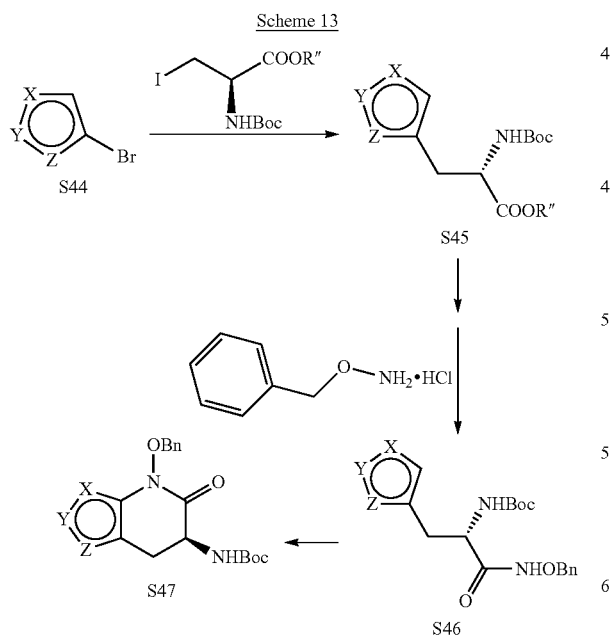

Preparation of specific heteroaryl intermediates is described in the following schemes.

The pyrazole ring may be synthesized as depicted in Scheme 14. Condensation of ethyl cyanoacetate or malono-

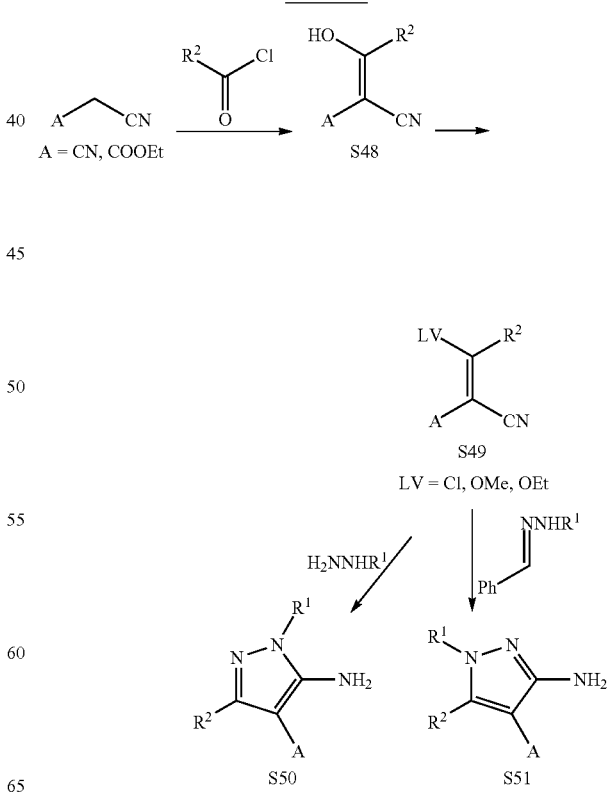

The synthesis of intermediates S55 and S57 is shown in Scheme 15. Compound S52, which may be prepared as reported by M. Kim et al., *Arch. Pharmacal. Res.* 2004, 27, 151-155, is converted to thioamide S53 via treatment with Lawesson's reagent, as described by W. Luo et al., *Synthesis* 2008, 3415-3422. Conversion of S53 to enamine S54 is then carried out with N,N-dimethylformamide and phosphorus oxychloride, using the method of J. Liebscher and B. Abegaz, *Synthesis* 1982, 769-771. Cyclization to the pyrazole S55 is carried out by reaction with a substituted hydrazine. Alternatively, compound S52 can be brominated at the alpha position to afford S56 and then transformed into the corresponding imidazole S57 through reaction with an optionally substituted amidine, using the general method described by F. Denorme et al., PCT Int Appl. WO 2008012010 A1. Compounds S55 and S57 can be converted to compounds of Formula I according to the methods of Scheme 1.

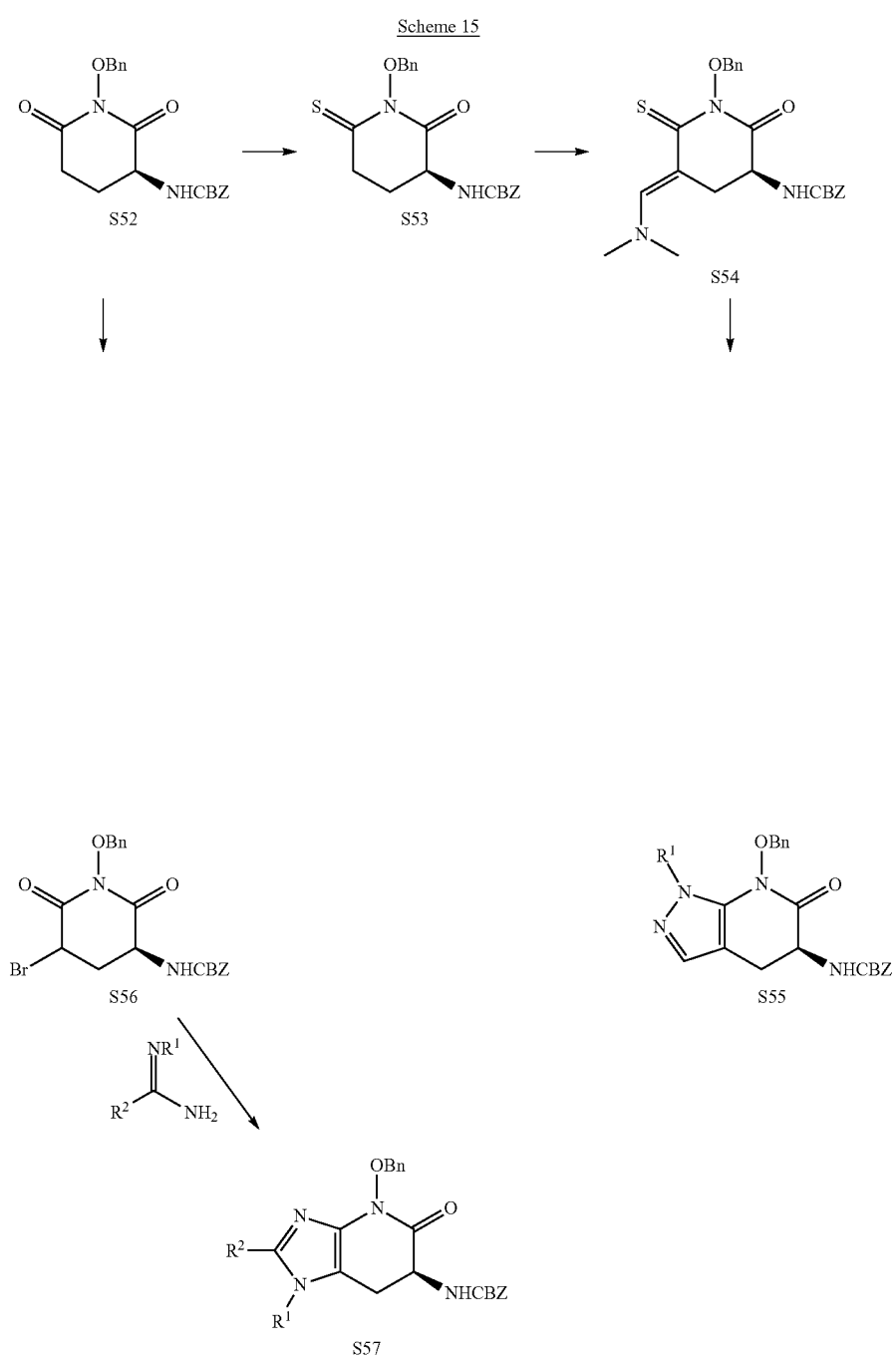

As shown in Scheme 16, compounds of Formula I wherein $R^3$ is H can be converted to carbamate prodrugs of Formula I wherein $R^3$ is $C(=O)NR^{7a}R^{7b}$ by reaction with the appropriate carbamoyl chloride in the presence of a base such as pyridine. It may be advantageous to temporarily protect the free primary amino group prior to this transformation. Similarly, use of an acyl chloride [ClC(=O)R$^7$] or acyl anhydride {[R$^7$C(=O)]$_2$O} provides the corresponding ester prodrug [Formula I wherein $R^3$ is $C(=O)R^7$], while a chloroformate reactant [ClC(=O)OR$^7$] can be used to prepare the carbonate prodrug [Formula I wherein $R^3$ is $C(=O)OR^7$]. Prodrugs of formula S59 (which are also compounds of Formula I), wherein $R^9$ is as defined above, can be prepared via alkylation of the compound of Formula I wherein $R^3$ is H with compound S58 (LV=CH$_3$SO$_3$, Cl, Br) in the presence of a base such as potassium carbonate.

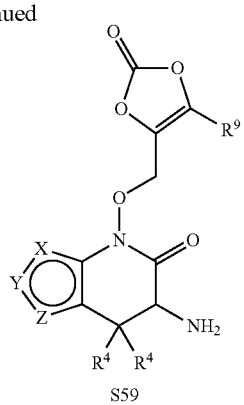

S59

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluants/gradients were chosen to provide appropriate R$_f$s or retention times.

Scheme 16

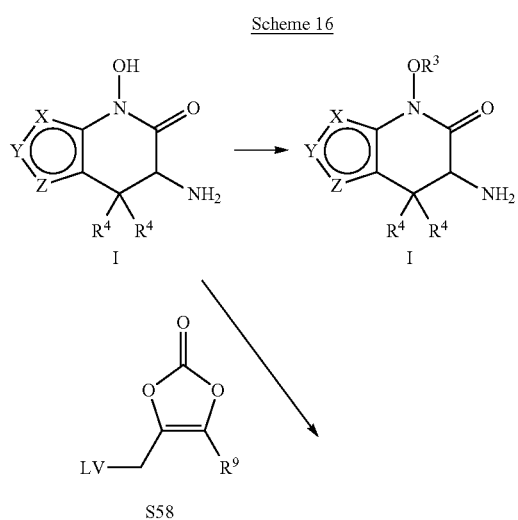

EXAMPLES

Example 1

(5S)-5-Amino-2-benzyl-7-hydroxy-2,4,5,7-tetrahydro-6H-pyrazolo[3,4-b]pyridin-6-one, HCl salt (1)

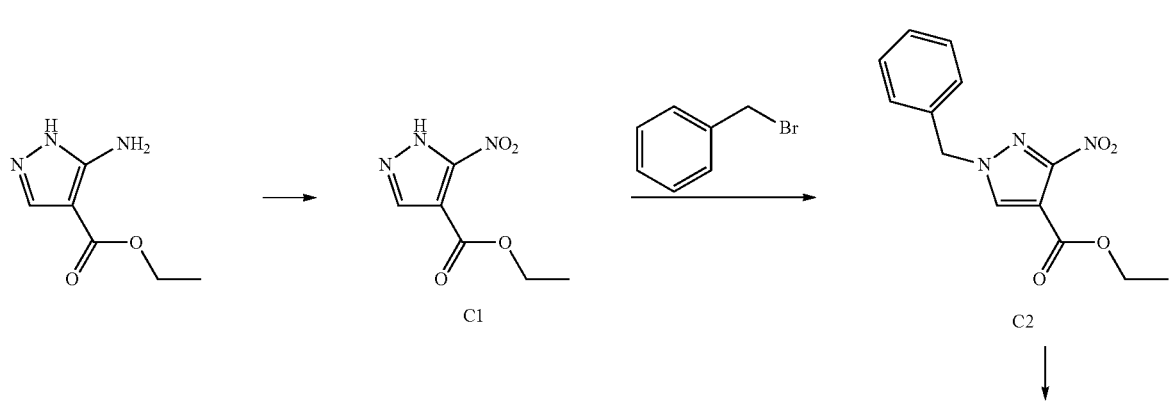

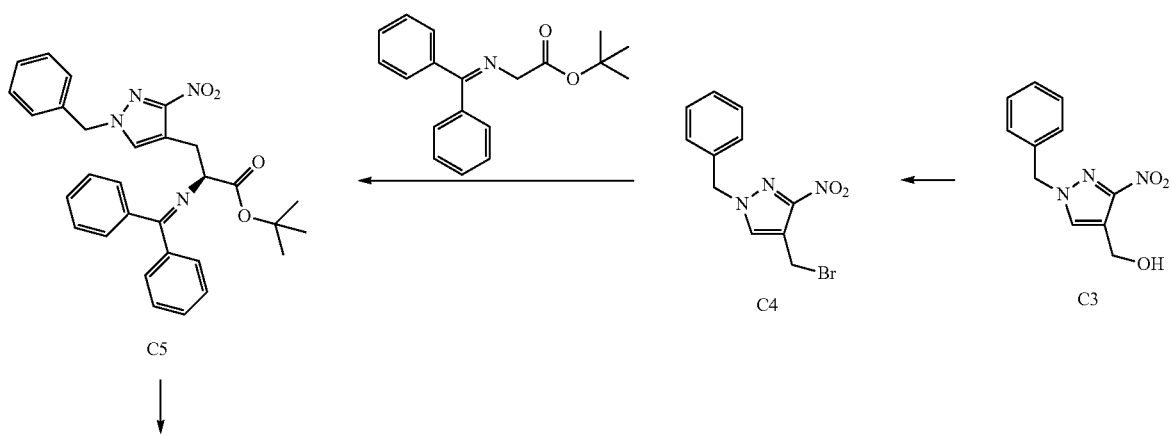
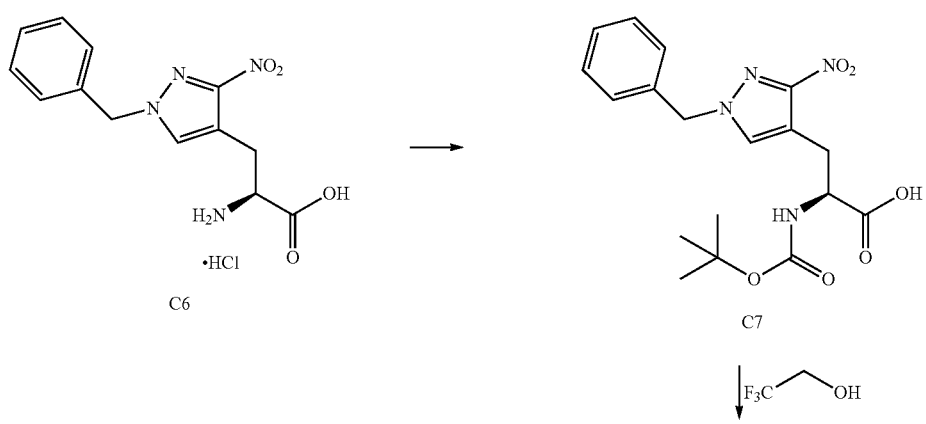
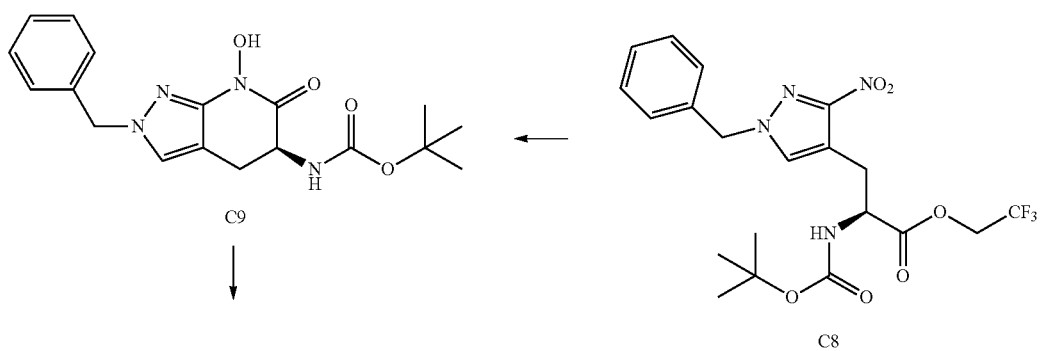
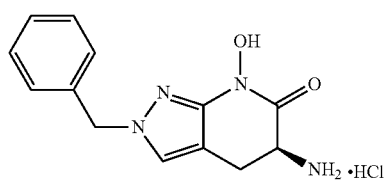

Step 1. Synthesis of ethyl 5-nitro-1H-pyrazole-4-carboxylate (C1). A mixture of sodium perborate tetrahydrate (95%, 15.7 g, 96.9 mmol) and acetic acid (60 mL) was heated to 85° C. Ethyl 5-amino-1H-pyrazole-4-carboxylate (3.0 g, 19 mmol) was added, and the mixture was allowed to react at 85° C. for 18 hours. The reaction was then poured into water and extracted with EtOAc. The combined organic layers were dried over magnesium sulfate, filtered and concentrated in vacuo; purification via silica gel chromatography (Gradient: 0% to 100% EtOAc in heptane) provided C1. Yield: 1.41 g, 7.62 mmol, 40%. LCMS m/z 184.0 (M−1). $^1$H NMR (400 MHz, CDCl$_3$) δ 1.39 (t, J=7.2 Hz, 3H), 4.40 (q, J=7.1 Hz, 2H), 8.32 (s, 1H).

Step 2. Synthesis of ethyl 1-benzyl-3-nitro-1H-pyrazole-4-carboxylate (C2). To a solution of C1 (2.86 g, 15.4 mmol) in N,N-dimethylformamide (60 mL) was added anhydrous potassium carbonate (12.8 g, 92.6 mmol), benzyl bromide (2.20 mL, 18.5 mmol) and a catalytic amount of potassium iodide. The reaction was heated at 60° C. for 18 hours, then diluted with EtOAc and washed with water. The organic layer was dried over magnesium sulfate, filtered and concentrated under reduced pressure. Purification using silica gel chromatography (Gradient: 0% to 100% EtOAc in heptane) provided C2 as an oil. Yield: 1.35 g, 4.90 mmol, 32%. An NOE experiment revealed a strong interaction between the pyrazole CH and aromatic protons on the phenyl group, supporting the indicated regiochemistry for C2. LCMS m/z 276.0 (M+1). $^1$H NMR (400 MHz, CDCl$_3$) δ 1.32 (t, J=7.1 Hz, 3H), 4.31 (q, J=7.1 Hz, 2H), 5.33 (s, 2H), 7.30-7.35 (m, 2H), 7.40-7.45 (m, 3H), 7.78 (s, 1H).

Step 3. Synthesis of (1-benzyl-3-nitro-1H-pyrazol-4-yl)methanol (C3). A solution of C2 (1.35 g, 4.90 mmol) in tetrahydrofuran (40 mL) was cooled to −40° C. and treated with lithium aluminum hydride (99%, 1 M, 10.3 mL, 10.3 mmol). The reaction was allowed to stir for 20 minutes at −40° C., then was quenched with saturated aqueous ammonium chloride solution. After addition of EtOAc and water, the layers were separated and the aqueous layer was extracted with EtOAc. The combined organic layers were dried over magnesium sulfate, filtered, and concentrated in vacuo to provide C3 as a solid. Yield: 1.29 g, 5.53 mmol, quantitative. $^1$H NMR (500 MHz, CDCl$_3$) δ 2.63 (br t, J=6 Hz, 1H), 4.79 (br d, J=5.4 Hz, 2H), 5.33 (s, 2H), 7.29-7.32 (m, 2H), 7.36-7.41 (m, 3H), 7.42 (s, 1H).

Step 4. Synthesis of 1-benzyl-4-(bromomethyl)-3-nitro-1H-pyrazole (C4). Carbon tetrabromide (3.67 g, 11.1 mmol) and triphenylphosphine (2.43 mL, 11.1 mmol) were added to a solution of C3 (1.29 g, 5.53 mmol) in dichloromethane (150 mL), and the reaction was allowed to stir at RT for 18 hours. After being washed with water, the reaction mixture was dried over magnesium sulfate, filtered, and concentrated under reduced pressure. Silica gel chromatography (Gradient: 0% to 100% EtOAc in heptane) afforded C4 as a solid. Yield: 951 mg, 3.21 mmol, 58%. LCMS m/z 297.9 (M+1). $^1$H NMR (400 MHz, CDCl$_3$) δ 4.60 (d, J=0.6 Hz, 2H), 5.32 (s, 2H), 7.28-7.32 (m, 2H), 7.36-7.41 (m, 3H), 7.52 (br s, 1H).

Step 5. Synthesis of tert-butyl 3-(1-benzyl-3-nitro-1H-pyrazol-4-yl)-N-(diphenylmethylene)-L-alaninate (C5). To a −30° C. solution of tert-butyl N-(diphenylmethylene)glycinate (98% 1.16 g, 3.85 mmol), C4 (951 mg, 3.21 mmol) and O-allyl-N-(9-anthracenylmethyl)cinchonidinium bromide (95%, 0.205 g, 0.322 mmol) in dichloromethane (25 mL) was added cesium hydroxide monohydrate (0.647 g, 3.85 mmol). (See E. J. Corey et al., *J. Am. Chem. Soc.* 1997, 119, 12414-12415.) The reaction was stirred at −30° C. for 18 hours, then washed with water, dried over magnesium sulfate, filtered and concentrated under reduced pressure. The residue was purified by chromatography on silica gel (Eluants: dichloromethane, then EtOAc) to give C5 as a gum. Yield: 1.63 g, 3.19 mmol, 99%. LCMS m/z 511.3 (M+1). $^1$H NMR (400 MHz, CDCl$_3$) δ 1.39 (s, 9H), 3.24 (dd, half of ABX pattern, J=14.3, 8.2 Hz, 1H), 3.38 (br dd, half of ABX pattern, J=14.3, 4.6 Hz, 1H), 4.22 (dd, J=8.3, 4.6 Hz, 1H), 5.25 (AB quartet, $J_{AB}$=14.6 Hz, $\Delta v_{AB}$=18.3 Hz, 2H), 6.72 (br d, J=7 Hz, 2H), 7.16-7.22 (m, 4H), 7.25-7.44 (m, 8H), 7.50-7.54 (m, 2H).

Step 6. Synthesis of 3-(1-benzyl-3-nitro-1H-pyrazol-4-yl)-L-alanine, HCl salt (C6). A solution of C5 (1.63 g, 3.19 mmol) in dichloromethane (100 mL) was treated with trifluoroacetic acid (15 mL) and allowed to stir for 66 hours. The reaction mixture was concentrated, and the residue was partitioned between diethyl ether and aqueous 4 N HCl. The organic layer was extracted with aqueous 4 N HCl, and the combined aqueous layers were concentrated in vacuo (azeotroping with methanol) to provide C6 as a yellow gum (1.05 g), which was used directly in the next step. LCMS m/z 291.0 (M+1).

Step 7. Synthesis of 3-(1-benzyl-3-nitro-1H-pyrazol-4-yl)-N-(tert-butoxycarbonyl)-L-alanine (C7). A solution of C6 (≤3.19 mmol) in tetrahydrofuran (12.9 mL) was treated with aqueous sodium hydroxide solution (1 M, 12.9 mL, 12.9 mmol) followed by di-tert-butyl dicarbonate (0.842 g, 3.86 mmol). The reaction was allowed to stir at RT for 18 hours, and then was neutralized by the addition of aqueous ammonium chloride solution and aqueous HCl. The mixture was extracted with EtOAc, and the combined organic extracts were dried over magnesium sulfate, filtered and concentrated under reduced pressure to provide C7 as a solid, contaminated with benzophenone. Corrected yield: 830 mg, 2.13 mmol, 67% from step 6. LCMS m/z 389.1 (M−1). $^1$H NMR (400 MHz, CD$_3$OD) δ 1.33 (s, 9H), 3.01 (dd, J=14.7, 9.5 Hz, 1H), 3.41 (dd, J=14.6, 4.6 Hz, 1H), 4.35 (dd, J=9.6, 4.7 Hz, 1H), 5.35 (s, 2H), 7.30-7.39 (m, 5H), 7.69 (s, 1H).

Step 8. Synthesis of 2,2,2-trifluoroethyl 3-(1-benzyl-3-nitro-1H-pyrazol-4-yl)-N-(tert-butoxycarbonyl)-L-alaninate (C8). 1-[3-(Dimethylamino)propyl]-3-ethylcarbodiimide hydrochloride (98%, 361 mg, 1.85 mmol), 4-(dimethylamino)pyridine (97%, 116 mg, 0.921 mmol) and 2,2,2-trifluoroethanol (99%, 1.36 mL, 18.5 mmol) were added to a solution of C7 (0.36 g, 0.92 mmol) in dichloromethane (30 mL), and the reaction mixture was allowed to stir for 18 hours. The reaction was washed with water, dried over magnesium sulfate, filtered and concentrated in vacuo. Purification via silica gel chromatography (Gradient: 0% to 100% EtOAc in heptane) afforded C8 as a solid. Yield: 223 mg, 0.472 mmol, 51%. LCMS m/z 471.1 (M−1). $^1$H NMR (400 MHz, CDCl$_3$) δ 1.37 (s, 9H), 3.24 (br dd, half of ABX pattern, J=14.7, 7.9 Hz, 1H), 3.35 (dd, half of ABX system, J=15.0, 5.7 Hz, 1H), 4.42-4.52 (m, 2H), 4.59 (br ddd, J=8, 8, 6 Hz, 1H), 5.13 (br d, J=8 Hz, 1H), 5.31 (s, 2H), 7.26-7.32 (m, 3H), 7.36-7.42 (m, 3H).

Step 9. Synthesis of tert-butyl [(5S)-2-benzyl-7-hydroxy-6-oxo-4,5,6,7-tetrahydro-2H-pyrazolo[3,4-b]pyridin-5-yl]carbamate (C9). To a solution of C8 (110 mg, 0.233 mmol) in pyridine (10 mL) was added 5% platinum on carbon (35 mg, 0.0090 mmol), and the reaction was subjected to hydrogenation at 30 psi for 3 hours on a Parr shaker. After filtration through Celite, the filter pad was rinsed with EtOAc (10 mL) and the combined filtrates were concentrated in vacuo. Purification using silica gel chromatography (Gradient: 0% to 100% EtOAc in heptane) provided C9 as a solid. Yield: 55 mg, 0.15 mmol, 64%. LCMS m/z 359.2 (M+1). $^1$H NMR (400 MHz, CDCl$_3$) δ 1.48 (s, 9H), 2.49 (br dd, J=14, 14 Hz, 1H), 3.30 (br dd, J=14, 7 Hz, 1H), 4.20-4.29 (m, 1H), 5.21 (AB quartet, $J_{AB}$=15.2 Hz, $\Delta v_{AB}$=11.1 Hz, 2H), 5.61 (br s, 1H), 7.07-7.08 (m, 1H), 7.14-7.20 (m, 2H), 7.29-7.36 (m, 3H), 10.74 (br s, 1H).

Step 10. Synthesis of Example 1. C9 (29 mg, 0.081 mmol) was dissolved in a minimum quantity of dichloromethane (approximately 0.3 mL) and treated with a solution of HCl (4 N in 1,4-dioxane, 1 mL, 4 mmol). After 1 hour at RT, the reaction was concentrated in vacuo to provide a solid, which was slurried in diethyl ether and filtered to afford a white solid for Example 1. Yield: 13 mg, 0.044 mmol, 54%. LCMS m/z 259.2 (M+1). $^1$H NMR (400 MHz, CD$_3$OD) δ 2.85 (ddd, J=14.6, 13.7, 1.0 Hz, 1H), 3.24 (dd, J=14.6, 7.4 Hz, 1H), 4.39 (dd, J=13.7, 7.4 Hz, 1H), 5.24 (s, 2H), 7.26-7.36 (m, 5H), 7.57 (d, J=0.8 Hz, 1H).

Example 2

(5S)-5-Amino-3-benzyl-7-hydroxy-1-methyl-1,4,5, 7-tetrahydro-6H-pyrazolo[3,4-b]pyridin-6-one, trifluoroacetate salt (2)

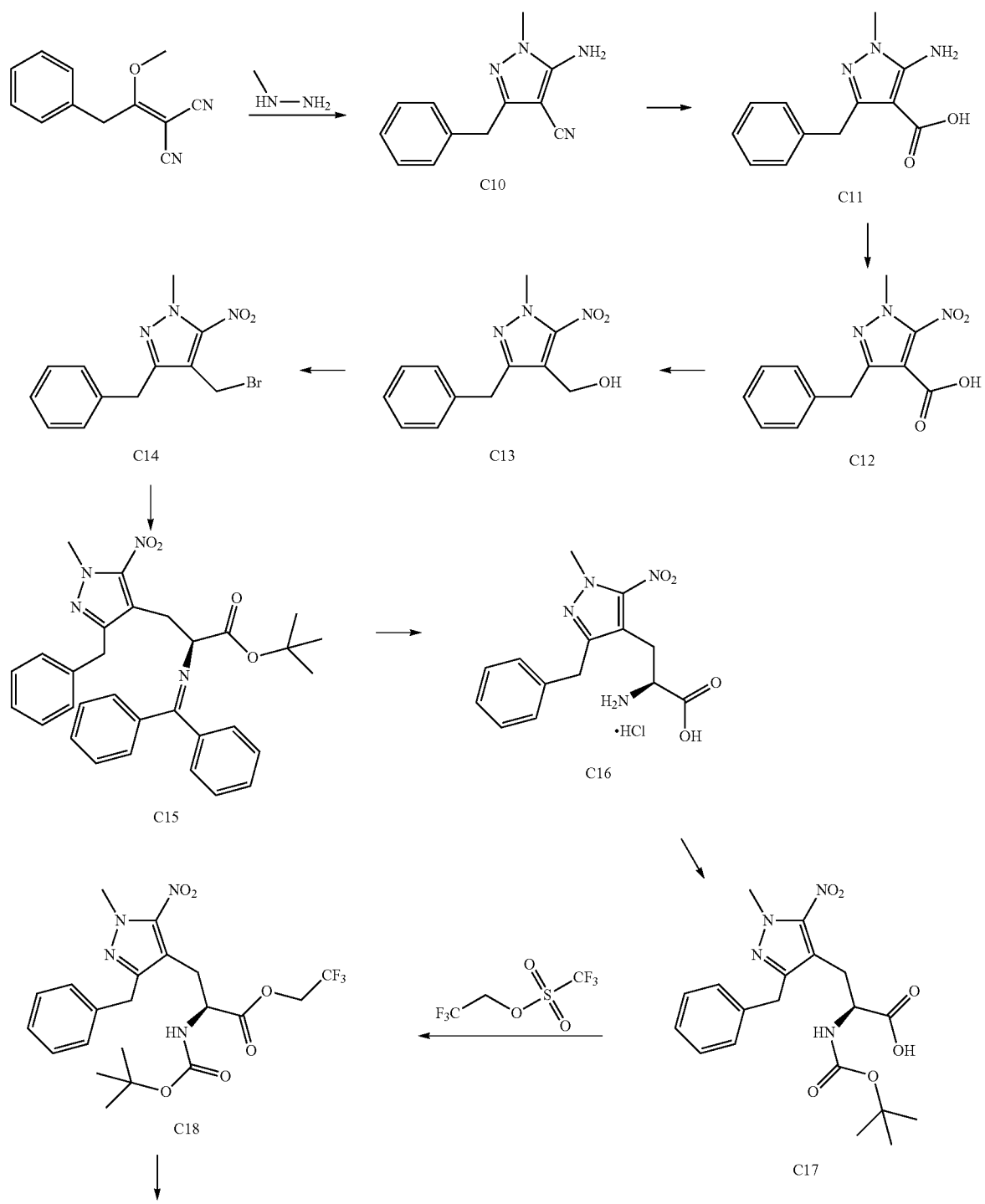

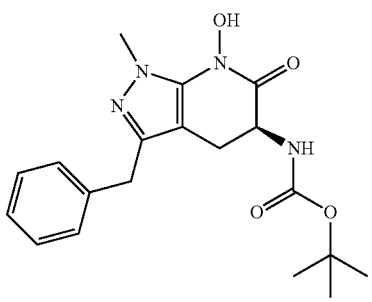 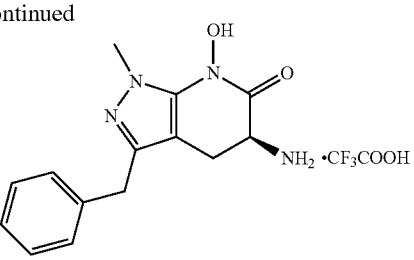

C19

2

Step 1. Synthesis of 5-amino-3-benzyl-1-methyl-1H-pyrazole-4-carbonitrile (C10). A mixture of (1-methoxy-2-phenylethylidene)malononitrile (prepared by the method of B. C. Kraybill et al., *J. Am. Chem. Soc.* 2002, 124, 12118-12128; 10 g, 50 mmol) and methylhydrazine (2.3 g, 50 mmol) in ethanol (120 mL) was heated to reflux for 10 minutes. The reaction was concentrated in vacuo, and the residue was diluted with water (200 mL) and extracted with EtOAc (3×100 mL). The combined organic layers were washed with brine, dried over sodium sulfate, filtered and concentrated under reduced pressure to afford C10 as a yellow solid. Yield: 10 g, 47 mmol, 94%.

Step 2. Synthesis of 5-amino-3-benzyl-1-methyl-1H-pyrazole-4-carboxylic acid (C11). To a solution of sodium hydroxide (10 g, 0.25 mol) in water (100 mL) was added C10 (5.00 g, 23.6 mmol) in one portion. The mixture was heated at reflux for 18 hours, then cooled to RT and extracted with EtOAc (3×100 mL). The aqueous layer was neutralized to a pH of 6 to 7 using aqueous 1 N HCl, and then extracted with EtOAc (3×150 mL). The combined organic layers from the neutral extraction were washed with brine, dried over sodium sulfate, filtered and concentrated in vacuo. Purification via silica gel chromatography (Eluant: 1:1 EtOAc/petroleum ether) afforded C11 as a white solid. Yield: 4.7 g, 20 mmol, 85%. $^1$H NMR (400 MHz, DMSO-$d_6$) δ 3.47 (s, 3H), 3.94 (s, 2H), 6.15 (br s, 2H), 7.10-7.26 (m, 5H), 11.80 (br s, 1H).

Step 3. Synthesis of 3-benzyl-1-methyl-5-nitro-1H-pyrazole-4-carboxylic acid (C12). A solution of sodium nitrite (3.00 g, 43.5 mmol) in water (2 mL) was added slowly, in a drop-wise fashion, to a 0° C. suspension of C11 (5.00 g, 21.6 mmol) in aqueous tetrafluoroboric acid (48%, 500 mL). The reaction was maintained at −5 to 0° C. for five minutes, then added over 30 minutes to a suspension of copper (5.0 g, 79 mmol) in saturated aqueous sodium nitrite solution, while keeping the internal temperature below 0° C. The reaction was stirred at −5 to 0° C. for one hour, and the resulting mixture was extracted with EtOAc (3×200 mL). The combined organic layers were washed with brine, dried over sodium sulfate, filtered and concentrated in vacuo. Silica gel chromatography (Eluant: 1:1 EtOAc/petroleum ether) provided C12 as a pale yellow solid. Yield: 3.5 g, 13 mmol, 60%. $^1$H NMR (400 MHz, CD$_3$OD) δ 3.98 (s, 3H), 4.14 (s, 2H), 7.12-7.26 (m, 5H).

Step 4. Synthesis of (3-benzyl-1-methyl-5-nitro-1H-pyrazol-4-yl)methanol (C13). Borane-methyl sulfide complex (2 M in tetrahydrofuran, 18 mL, 36 mmol) was added drop-wise to a −20° C. solution of C12 (4.7 g, 18 mmol) in tetrahydrofuran (120 mL), and the reaction mixture was then heated to reflux for 2 hours. The resulting mixture was cooled, poured into water (100 mL), and concentrated under reduced pressure. The remaining aqueous material was extracted with EtOAc (3×100 mL), and the combined organic layers were washed with brine, dried over sodium sulfate, filtered and concentrated in vacuo to afford C13 as a white solid. Yield: 3.5 g, 14 mmol, 78%. LCMS m/z 248.1 (M+1). $^1$H NMR (400 MHz, CDCl$_3$) δ 2.34 (t, J=7.0 Hz, 1H), 4.09 (s, 2H), 4.23 (s, 3H), 4.68 (d, J=7.0 Hz, 2H), 7.23-7.36 (m, 5H).

Step 5. Synthesis of 3-benzyl-4-(bromomethyl)-1-methyl-5-nitro-1H-pyrazole (C14). C13 was converted to C14 according to the general procedure for the synthesis of C4 in Example 1. C14 was obtained as an oil. Yield: 969 mg, 3.12 mmol, 71%. LCMS m/z 311.9 (M+1). $^1$H NMR (400 MHz, CDCl$_3$) δ 4.06 (br s, 2H), 4.22 (s, 3H), 4.50 (s, 2H), 7.23-7.35 (m, 5H).

Step 6. Synthesis of tert-butyl 3-(3-benzyl-1-methyl-5-nitro-1H-pyrazol-4-yl)-N-(diphenylmethylene)-L-alaninate (C15). C14 was converted to C15 according to the general procedure for the synthesis of C5 in Example 1. C15 was obtained as an oil. Yield: 771 mg, 1.47 mmol, 47%. LCMS m/z 525.1 (M+1). $^1$H NMR (500 MHz, CDCl$_3$) δ 1.47 (s, 9H), 3.20 (dd, half of ABX pattern, J=13.8, 9.9 Hz, 1H), 3.32 (dd, half of ABX pattern, J=13.9, 3.7 Hz, 1H), 3.84 (d, J=15.6 Hz, 1H), 4.04 (d, J=15.6 Hz, 1H), 4.13 (s, 3H), 4.28 (dd, J=9.9, 3.7 Hz, 1H), 6.71 (br d, J=7 Hz, 2H), 7.15-7.21 (m, 3H), 7.22-7.27 (m, 2H), 7.31-7.42 (m, 6H), 7.62-7.65 (m, 2H).

Step 7. Synthesis of 3-(3-benzyl-1-methyl-5-nitro-1H-pyrazol-4-yl)-L-alanine, HCl salt (C16). C15 (505 mg, 0.963 mmol) was dissolved in acetonitrile (10 mL) and treated with concentrated aqueous HCl (3 mL). The reaction was heated at reflux for 20 hours, then cooled to RT and filtered. The filtrate was concentrated in vacuo, and the residue was partitioned between diethyl ether and 1 N aqueous HCl. The aqueous layer was washed once with diethyl ether and then concentrated under reduced pressure, azeotroping with toluene, to provide crude C16, which was taken directly to the next step without further purification. LCMS m/z 305.1 (M+1). $^1$H NMR (400 MHz, CD$_3$OD) δ 3.20 (dd, half of ABX pattern, J=14.4, 7.5 Hz, 1H), 3.34 (dd, half of ABX pattern, J=14.5, 7.5 Hz, 1H, assumed; partially obscured by solvent peak), 3.80 (dd, J=7.6, 7.5 Hz, 1H), 4.03 (AB quartet, $J_{AB}$=15.8 Hz, $\Delta v_{AB}$=15.9 Hz, 2H), 4.20 (s, 3H), 7.19-7.31 (m, 5H).

Step 8. Synthesis of 3-(3-benzyl-1-methyl-5-nitro-1H-pyrazol-4-yl)-N-(tert-butoxycarbonyl)-L-alanine (C17). C16 (≤0.963 mmol) was suspended in a mixture of water (10 mL) and 1,4-dioxane (10 mL). Triethylamine (97%, 0.464 mL, 3.23 mmol) was added, followed by di-tert-butyl dicarbonate (98%, 360 mg, 1.62 mmol), and the reaction was allowed to stir for 18 hours. Additional triethylamine (2 equivalents) and di-tert-butyl dicarbonate (0.5 equivalents) were added to the reaction, and stirring was continued for an additional 2 hours. The reaction was partitioned between EtOAc and aqueous citric acid solution. The aqueous layer (pH ~5) was extracted twice with EtOAc, and the combined organic layers were dried over magnesium sulfate, filtered and concentrated in vacuo to provide C17 as an oil. Yield: 266 mg, 0.658 mmol, 68% from step 7. LCMS m/z 405.2 (M+1). $^1$H NMR (400 MHz, CDCl$_3$) δ 1.37 (br s, 9H), 3.02 (dd, J=14, 9 Hz, 1H), 3.26 (br dd, J=14, 5 Hz, 1H), 4.02 (AB quartet, 2 downfield peaks are broad, $J_{AB}$=15.6 Hz, $\Delta v_{AB}$=26.4 Hz, 2H), 4.17 (s, 3H), 4.42-4.51 (br m, 1H), 5.00 (br d, J=8 Hz, 1H), 7.19-7.32 (m, 5H).

Step 9. Synthesis of 2,2,2-trifluoroethyl 3-(3-benzyl-1-methyl-5-nitro-1H-pyrazol-4-yl)-N-(tert-butoxycarbonyl)-L-alaninate (C18). 2,2,2-Trifluoroethyl trifluoromethanesulfonate (198 mg, 0.853 mmol) was added to a solution of C17 (266 mg, 0.658 mmol) and triethylamine (0.229 mL, 1.64 mmol) in tetrahydrofuran (5 mL), and the mixture was heated at 60° C. for 19 hours, then allowed to stir at RT for 4 days. After removal of volatiles in vacuo, the residue was partitioned between diethyl ether and water. The organic layer was washed with brine, then concentrated in vacuo. Purification using silica gel chromatography (Gradient: 0% to 40% EtOAc in heptane) provided C18 as a yellow oil. Yield: 218 mg, 0.448 mmol, 68%. LCMS m/z 387.2 [(M—CO$_2$ and 2-methylprop-1-ene)+1]. $^1$H NMR (400 MHz, CDCl$_3$) δ 1.39 (br s, 9H), 3.06 (dd, half of ABX pattern, J=14.0, 8.8 Hz, 1H), 3.17 (br dd, half of ABX pattern, J=14, 6 Hz, 1H), 4.01 (AB quartet, 2 downfield peaks are broad, $J_{AB}$=15.6 Hz, $\Delta v_{AB}$=33 Hz, 2H), 4.19 (s, 3H), 4.41-4.58 (m, 3H), 4.88 (br d, J=8 Hz, 1H), 7.21-7.33 (m, 5H).

Step 10. Synthesis of tert-butyl [(5S)-3-benzyl-7-hydroxy-1-methyl-6-oxo-4,5,6,7-tetrahydro-1H-pyrazolo[3,4-b]pyridin-5-yl]-carbamate (C19). A mixture of C18 (215 mg, 0.442 mmol) and 5% platinum on carbon (172 mg) in pyridine (10 mL) was hydrogenated for 3 hours on a Parr shaker at 30 psi hydrogen. The reaction was filtered through Celite, and the filter pad was washed with EtOAc (30 mL) and methanol (10 mL). The filtrate was concentrated in vacuo, and the residue was triturated with diethyl ether to provide 55 mg of a white solid. Purification using silica gel chromatography (Gradients: 0% to 100% EtOAc in heptane, then 0% to 15% methanol in EtOAc, then eluted with 15% methanol in dichloromethane) provided C19 as a white solid. Yield: 50 mg, 0.13 mmol, 29%. Additional product could be obtained by purification of the filtrate from the trituration described above. LCMS m/z 373.2 (M+1). $^1$H NMR (400 MHz, CD$_3$OD) δ 1.45 (br s, 9H), 2.42 (dd, J=14.8. 13.7 Hz, 1H), 2.70 (dd, J=14.9, 7.1 Hz, 1H), 3.87 (s, 2H), 3.90 (s, 3H), 4.36-4.43 (m, 1H), 7.15-7.29 (m, 5H).

Step 11. Synthesis of Example 2. Trifluoroacetic acid (1 mL) was added to a solution of C19 (21 mg, 0.056 mmol) in dichloromethane (2 mL), and the reaction was allowed to stir for 1 hour at RT. Removal of solvents in vacuo provided a beige solid for Example 2. Yield: 20 mg, 0.052 mmol, 93%. $^1$H NMR (400 MHz, CD$_3$OD) δ 2.55 (dd, J=14, 14 Hz, 1H), 2.86 (dd, J=14.4, 7.4 Hz, 1H), 3.89-3.91 (m, 2H), 3.93 (s, 3H), 4.34 (dd, J=13.7, 7.4 Hz, 1H), 7.17-7.31 (m, 5H).

Example 3

(5S)-5-Amino-3-benzyl-7-hydroxy-2-methyl-2,4,5,7-tetrahydro-6H-pyrazolo[3,4-b]pyridin-6-one, HCl salt (3)

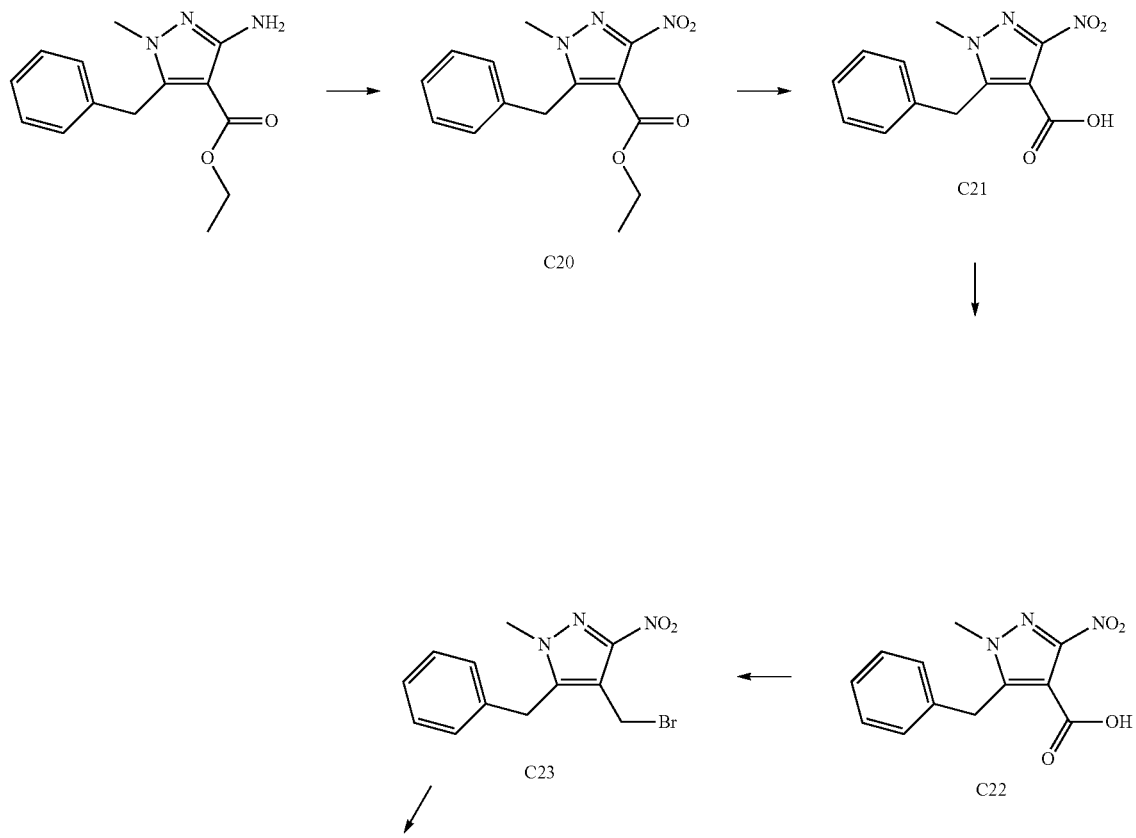

49                                                    50
-continued
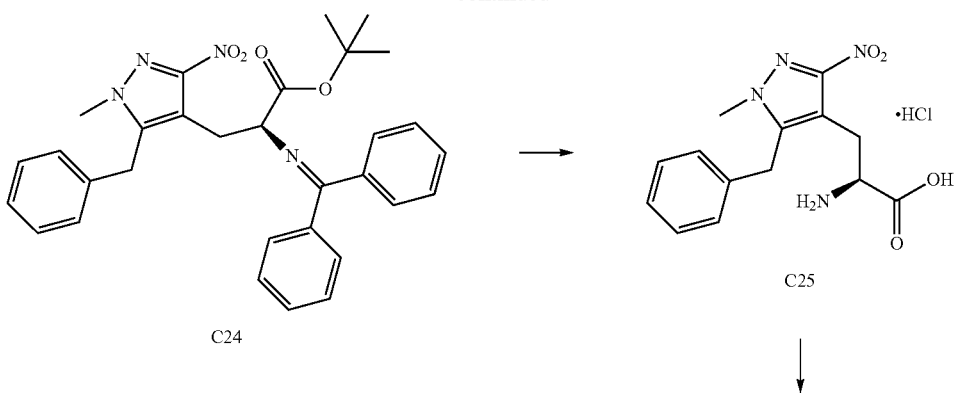
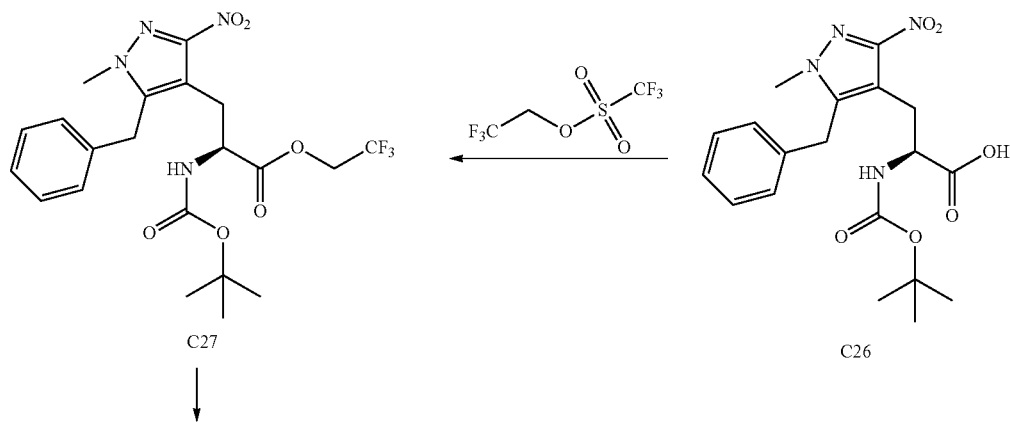
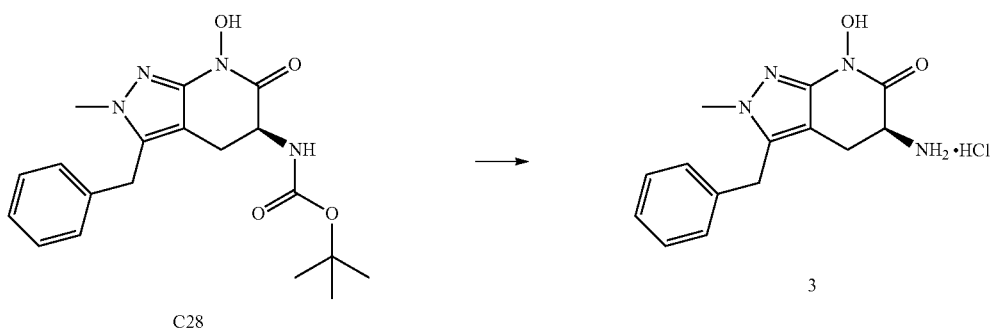

Step 1. Synthesis of ethyl 5-benzyl-1-methyl-3-nitro-1H-pyrazole-4-carboxylate (C20). A mixture of sodium perborate tetrahydrate (95%, 3.12 g, 19.3 mmol) and trifluoroacetic acid (10 mL) was heated to 75° C. To this was added a solution of ethyl 3-amino-5-benzyl-1-methyl-1H-pyrazole-4-carboxylate (prepared according to the method of Y. Xia et al., *J. Med. Chem.* 1997, 40, 4372-4377; 1.00 g, 3.86 mmol) in trifluoroacetic acid, and the mixture was allowed to react at 75° C. for 2.5 hours. The reaction was then cooled, poured into water and extracted with EtOAc. The combined organic layers were washed with water, dried over magnesium sulfate, filtered and concentrated in vacuo; purification via silica gel chromatography (Eluant: 30% EtOAc in heptane) provided C20 as a dark yellow oil. Yield: 333 mg, 1.15 mmol, 30%. LCMS m/z 290.2 (M+1). $^1$H NMR (400 MHz, CDCl$_3$) δ 1.32 (t, J=7.1 Hz, 3H), 3.74 (s, 3H), 4.33 (br s, 2H), 4.34 (q, J=7.1 Hz, 2H), 7.14-7.18 (m, 2H), 7.25-7.30 (m, 1H), 7.31-7.36 (m, 2H).

Step 2. Synthesis of 5-benzyl-1-methyl-3-nitro-1H-pyrazole-4-carboxylic acid (C21). Lithium hydroxide (1 M aqueous solution, 4.11 mL, 4.11 mmol) was added to a solution of C20 (793 mg, 2.74 mmol) in tetrahydrofuran (8 mL) and methanol (4 mL), and the reaction was allowed to stir for 20 hours. After removal of solvents in vacuo, the residue was acidified with 1 N aqueous HCl and extracted with EtOAc. The combined organic layers were washed with water and with brine, then dried over magnesium sulfate, filtered and concentrated under reduced pressure, affording C21 as an oil. Yield: 656 mg, 2.51 mmol, 92%. LCMS m/z 260.1 (M−1). $^1$H NMR (400 MHz, CDCl$_3$) δ 3.79 (s, 3H), 4.47 (br s, 2H), 7.13-7.17 (m, 2H), 7.25-7.30 (m, 1H), 7.31-7.36 (m, 2H).

Step 3. Synthesis of (5-benzyl-1-methyl-3-nitro-1H-pyrazol-4-yl)methanol (C22). A solution of borane in tetrahydrofuran (1 M, 10.0 mL, 10.0 mmol) was added to a solution of C21 (656 mg, 2.51 mmol) in tetrahydrofuran (20 mL), and the reaction was heated to 50° C. for 5 hours. The reaction was slowly added to water (50 mL), acidified with 0.5 N HCl, and extracted with EtOAc. The combined organic layers were washed with water, washed with brine and dried over magnesium sulfate. After filtration, the filtrate was concentrated in vacuo to afford C22 as a colorless oil. Yield: 583 mg, 2.36 mmol, 94%. $^1$H NMR (400 MHz, CDCl$_3$) δ 3.76 (s, 3H), 4.12 (s, 2H), 4.77 (br s, 2H), 7.09-7.13 (m, 2H), 7.25-7.30 (m, 1H), 7.31-7.37 (m, 2H).

Step 4. Synthesis of 5-benzyl-4-(bromomethyl)-1-methyl-3-nitro-1H-pyrazole (C23). Phosphorus tribromide (0.253 mL, 2.67 mmol) was added to a solution of C22 (134 mg, 0.542 mmol) in dichloromethane (10 mL), and the reaction was allowed to stir at RT for 2 hours. It was then partitioned between cold water and additional dichloromethane, and the organic layer was washed with water, washed with brine, dried over magnesium sulfate, filtered and concentrated in vacuo. Purification using silica gel chromatography (Eluant: 30% EtOAc in heptane) afforded C23 as a colorless oil. Yield: 143 mg, 0.461 mmol, 85%. LCMS m/z 312.0 (M+1). $^1$H NMR (400 MHz, CDCl$_3$) δ 3.75 (s, 3H), 4.13 (br s, 2H), 4.69 (s, 2H), 7.11-7.15 (m, 2H), 7.28-7.33 (m, 1H), 7.33-7.38 (m, 2H).

Step 5. Synthesis of tert-butyl 3-(5-benzyl-1-methyl-3-nitro-1H-pyrazol-4-yl)-N-(diphenylmethylene)-L-alaninate (C24). C23 was converted to C24 according to the general procedure for the synthesis of C5 in Example 1. C24 was obtained as a colorless glass. Yield: 194 mg, 0.370 mmol, 80%. LCMS m/z 525.3 (M+1). $^1$H NMR (400 MHz, CDCl$_3$) δ 1.44 (s, 9H), 3.24 (dd, J=14.0, 9.8 Hz, 1H), 3.52 (dd, J=14.0, 4.0 Hz, 1H), 3.63 (s, 3H), 3.86 (d, J=17.0 Hz, 1H), 4.27 (d, J=17.1 Hz, 1H), 4.36 (dd, J=9.7, 4.0 Hz, 1H), 6.70-6.77 (m, 2H), 6.97-7.02 (m, 2H), 7.20-7.25 (m, 3H), 7.31-7.44 (m, 6H), 7.60-7.64 (m, 2H).

Step 6. Synthesis of 3-(5-benzyl-1-methyl-3-nitro-1H-pyrazol-4-yl)-L-alanine, HCl salt (C25). Concentrated HCl (12 M, 0.156 mL, 1.87 mmol) was slowly added to a solution of C24 (194 mg, 0.370 mmol) in acetonitrile (10 mL), and the reaction was heated at 50° C. for 4 hours. After removal of solvent in vacuo, the residue was partitioned between diethyl ether (50 mL) and water (10 mL), and the aqueous layer was washed twice with diethyl ether. Concentration of the aqueous layer under reduced pressure provided C25 as a colorless solid. Yield: 125 mg, 0.367 mmol, 99%. LCMS m/z 305.1 (M+1). $^1$H NMR (400 MHz, CD$_3$OD) δ 3.28 (dd, J=14.6, 7.0 Hz, 1H, assumed; partially obscured by solvent peak), 3.50 (dd, J=14.6, 7.8 Hz, 1H), 3.77 (s, 3H), 4.04 (dd, J=7.4, 7.4 Hz, 1H), 4.20 (AB quartet, $J_{AB}$=17.1 Hz, $\Delta v_{AB}$=22.9 Hz, 2H), 7.11-7.15 (m, 2H), 7.24-7.29 (m, 1H), 7.32-7.37 (m, 2H).

Step 7. Synthesis of 3-(5-benzyl-1-methyl-3-nitro-1H-pyrazol-4-yl)-N-(tert-butoxycarbonyl)-L-alanine (C26). Di-tert-butyl dicarbonate (96.9 mg, 0.444 mmol) was added to a solution of C25 (125 mg, 0.367 mmol) and triethylamine (0.208 mL, 1.48 mmol) in water (10 mL), and the reaction was allowed to stir at RT for 18 hours. After acidification of the reaction mixture to pH-5 with 10% aqueous citric acid solution, it was extracted with EtOAc. The combined organic layers were washed with water, dried over magnesium sulfate, filtered and concentrated in vacuo to provide C26 as a pale yellow foam (150 mg), which was taken directly to the following step. LCMS m/z 403.1 (M−1). $^1$H NMR (400 MHz, CD$_3$OD) δ 1.36 (br s, 9H), 3.05 (br dd, J=14.0, 9.6 Hz, 1H), 3.40 (br dd, J=14.2, 5.5 Hz, 1H), 3.68 (s, 3H), 4.17 (br AB quartet, $J_{AB}$=17.2 Hz, $\Delta v_{AB}$=30 Hz, 2H), 4.42 (br dd, J=9.4, 5.5 Hz, 1H), 7.10-7.16 (m, 2H), 7.22-7.27 (m, 1H), 7.29-7.35 (m, 2H).

Step 8. Synthesis of 2,2,2-trifluoroethyl 3-(5-benzyl-1-methyl-3-nitro-1H-pyrazol-4-yl)-N-(tert-butoxycarbonyl)-L-alaninate (C27). Trifluoroethyl trifluoromethanesulfonate (112 mg, 0.483 mmol) was added to a solution of C26 (≤0.367 mmol) and triethylamine (0.13 mL, 0.93 mmol) in tetrahydrofuran (10 mL), and the mixture was heated at 60° C. for 18 hours. After cooling, the reaction mixture was partitioned between EtOAc and water. The organic layer was washed with water, washed with brine, dried over magnesium sulfate, filtered and then concentrated in vacuo to afford C27 as an oil. Yield: 135 mg, 0.278 mmol, 76% from step 7. LCMS m/z 385.0 [(M—CO$_2$ and 2-methylprop-1-ene)−1]. $^1$H NMR (400 MHz, CDCl$_3$) δ 1.38 (br s, 9H), 3.24-3.36 (m, 2H), 3.73 (s, 3H), 4.03-4.15 (m, 2H), 4.44-4.57 (m, 3H), 5.16 (br d, J=8 Hz, 1H), 7.04 (br d, J=7.2 Hz, 2H), 7.25-7.36 (m, 3H).

Step 9. Synthesis of tert-butyl [(5S)-3-benzyl-7-hydroxy-2-methyl-6-oxo-4,5,6,7-tetrahydro-2H-pyrazolo[3,4-b]pyridin-5-yl]carbamate (C28). C27 was converted to C28 according to the general procedure for the synthesis of C9 in Example 1. C28 was obtained as a colorless solid. Yield: 71 mg, 0.19 mmol, 68%. LCMS m/z 373.2 (M+1). $^1$H NMR (400 MHz, CD$_3$OD) δ 1.46 (s, 9H), 2.57 (dd, J=15.0, 13.3 Hz, 1H), 2.79 (br dd, J=15, 7 Hz, 1H), 3.63 (s, 3H), 4.02 (s, 2H), 4.42 (br dd, J=13, 7 Hz, 1H), 7.15-7.19 (m, 2H), 7.21-7.26 (m, 1H), 7.29-7.34 (m, 2H).

Step 10. Synthesis of Example 3. C28 (68 mg, 0.18 mmol) was combined with a solution of HCl in 1,4-dioxane (4 M, 2 mL, 8 mmol), and the reaction was allowed to stir at RT for 45 minutes. After concentration of the reaction in vacuo, the solid residue was slurried in diethyl ether to provide a sticky solid. This was dissolved in methanol and concentrated in vacuo, affording a solid for Example 3. Yield: 49 mg, 0.16 mmol, 88%. LCMS m/z 273.2 (M+1). ¹H NMR (400 MHz, CD₃OD) δ 2.65 (dd, J=14, 14 Hz, 1H), 2.93 (dd, J=14.5, 7.4 Hz, 1H), 3.68 (s, 3H), 4.07 (AB quartet, J$_{AB}$=16.5 Hz, Δν$_{AB}$=13.4 Hz, 2H), 4.35 (dd, J=13.5, 7.5 Hz, 1H), 7.18-7.21 (m, 2H), 7.23-7.28 (m, 1H), 7.31-7.36 (m, 2H).
Example 4
(6S)-6-Amino-1-benzyl-4-hydroxy-1,4,6,7-tetrahydro-5H-pyrazolo[4,3-b]pyridin-5-one, HCl salt (4)
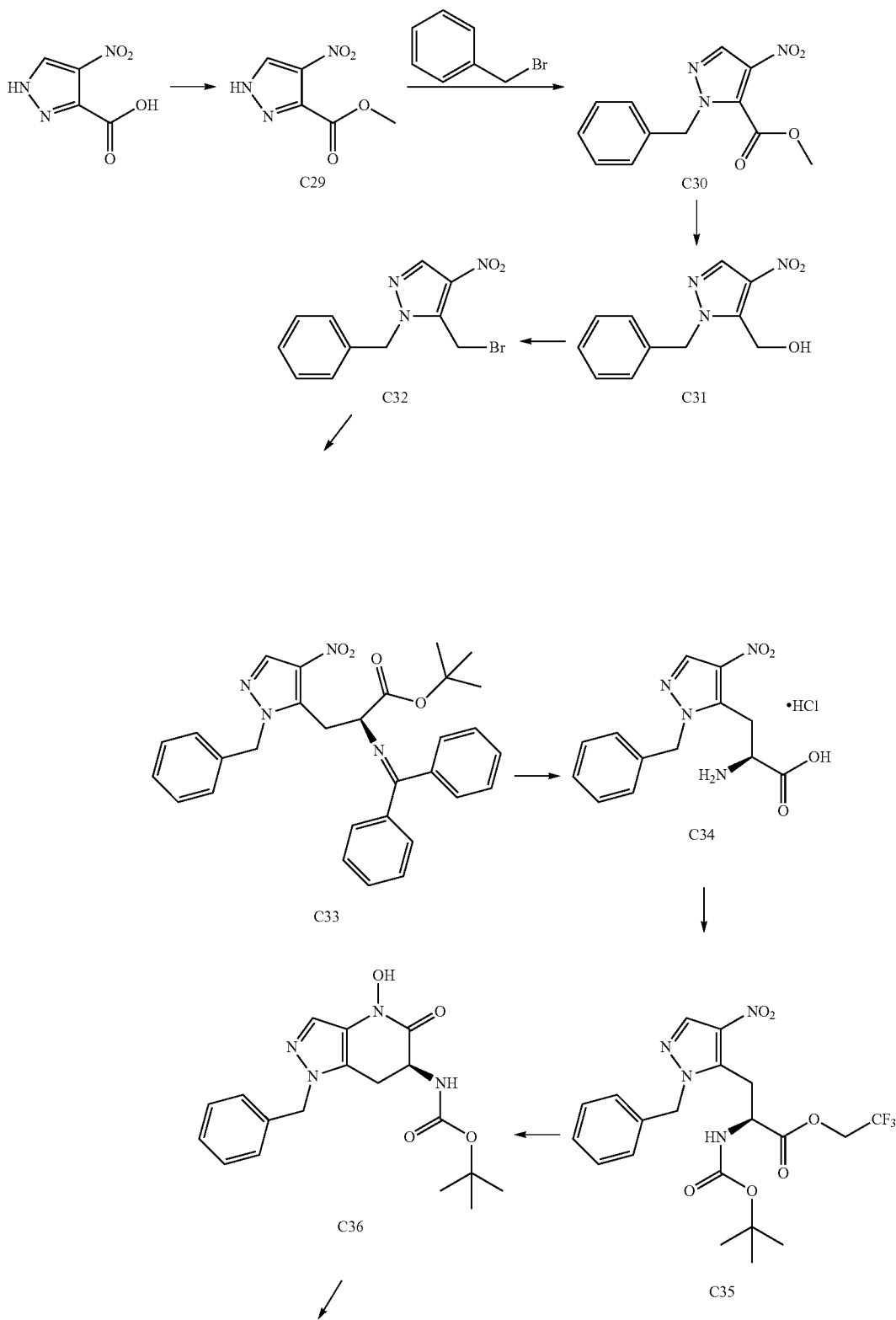

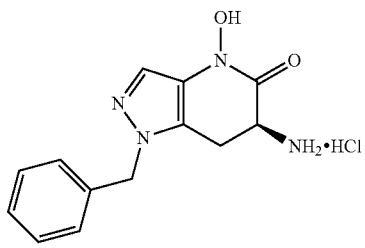

4

Step 1. Synthesis of methyl 4-nitro-1H-pyrazole-3-carboxylate (C29). Fuming sulfuric acid (4 mL) was added to a solution of 4-nitro-1H-pyrazole-3-carboxylic acid (16.0 g, 102 mmol) in methanol (200 mL), and the reaction was stirred at RT for 24 hours. The reaction mixture was concentrated, and the resulting solid was partitioned between EtOAc and water. The aqueous layer was extracted twice with EtOAc, and the combined organic layers were dried over magnesium sulfate, filtered and concentrated in vacuo, providing C29 as a white solid. Yield: 17.1 g, 99.9 mmol, 98%. LCMS m/z 170.0 (M−1). $^1$H NMR (400 MHz, CDCl$_3$) δ 4.05 (s, 3H), 8.40 (s, 1H).

Step 2. Synthesis of methyl 1-benzyl-4-nitro-1H-pyrazole-5-carboxylate (C30). To a solution of C29 (17.1 g, 99.9 mmol) in acetone (500 mL) was added benzyl bromide (11.8 mL, 99.8 mmol) and potassium carbonate (13.8 g, 99.8 mmol), and the reaction was heated at reflux for 2.25 hours. Solvent was removed in vacuo, and the residue was partitioned between water and dichloromethane. The aqueous layer was extracted twice with dichloromethane, and the combined organic layers were dried over magnesium sulfate, filtered and concentrated under reduced pressure. The resulting oil was combined with material derived from a very similar reaction carried out on 28 mmol of C29, and purification was effected via silica gel chromatography (Gradient: 0% to 40% EtOAc in heptane). The less polar isomer was collected to provide C30 as an oil. Yield: 7.07 g, 27.1 mmol, 21%. The regiochemistry of C30 was assigned based on NOE studies carried out on C30 and the regioisomeric, more polar material from the chromatography. $^1$H NMR (400 MHz, CDCl$_3$) δ 3.92 (s, 3H), 5.49 (s, 2H), 7.24-7.28 (m, 2H), 7.34-7.39 (m, 3H), 8.07 (s, 1H).

Step 3. Synthesis of (1-benzyl-4-nitro-1H-pyrazol-5-yl)methanol (C31). Sodium borohydride (1.44 g, 38.0 mmol) was added to a solution of C30 (4.97 g, 19.0 mmol) in tetrahydrofuran (100 mL). The mixture was cooled to 0° C., and methanol (~3.9 mL) was added drop-wise, at a rate such that effervescence was controlled. The reaction was then allowed to warm to RT and stirred at that temperature for 1 hour. After being quenched with water (1 mL), the reaction mixture was concentrated in vacuo. The residue was partitioned between dichloromethane and water, and the organic layer was washed with brine, dried, filtered and evaporated to provide C31 as a light pink solid. Yield: 4.08 g, 17.5 mmol, 92%. $^1$H NMR (400 MHz, CD$_3$OD) δ 4.99 (s, 2H), 5.53 (s, 2H), 7.25-7.37 (m, 5H), 8.16 (s, 1H).

Step 4. Synthesis of 1-benzyl-5-(bromomethyl)-4-nitro-1H-pyrazole (C32). C31 was converted to C32 according to the procedure for the synthesis of C4 in Example 1. C32 was obtained as a white solid. Yield: 1.69 g, 5.71 mmol, 66%. LCMS m/z 296.1 (M+1). $^1$H NMR (400 MHz, CDCl$_3$) δ 4.72 (s, 2H), 5.46 (s, 2H), 7.23-7.27 (m, 2H), 7.36-7.42 (m, 3H), 8.17 (s, 1H).

Step 5. Synthesis of tert-butyl 3-(1-benzyl-4-nitro-1H-pyrazol-5-yl)-N-(diphenylmethylene)-L-alaninate (C33). C32 was converted to C33 according to the general procedure for the synthesis of C5 in Example 1. C33 was obtained as an oil. Yield: 1.29 g, 2.53 mmol, 72%. LCMS m/z 511.3 (M+1). $^1$H NMR (400 MHz, CDCl$_3$) δ 1.47 (s, 9H), 3.50 (dd, J=14.2, 10.2 Hz, 1H), 3.71 (dd, J=14.1, 3.6 Hz, 1H), 4.45 (dd, J=10.2, 3.7 Hz, 1H), 5.28 (d, J=15.5 Hz, 1H), 5.64 (d, J=15.5 Hz, 1H), 6.72-6.76 (m, 2H), 7.15-7.19 (m, 2H), 7.30-7.45 (m, 9H), 7.60-7.64 (m, 2H), 8.10 (s, 1H).

Step 6. Synthesis of 3-(1-benzyl-4-nitro-1H-pyrazol-5-yl)-L-alanine, HCl salt (C34). C33 (652 mg, 1.28 mmol) was converted to C34 according to the general procedure for the synthesis of C25 in Example 3. C34 was obtained as a white solid, which was carried directly into the next step. LCMS m/z 291.2 (M+1). $^1$H NMR (400 MHz, CD$_3$OD) δ 3.59 (dd, half of ABX pattern, J=14.8, 6.7 Hz, 1H), 3.71 (dd, half of ABX pattern, J=14.7, 8.4 Hz, 1H), 4.12 (dd, J=8.2, 6.8 Hz, 1H), 5.49 (AB quartet, J$_{AB}$=15.9 Hz, Δv$_{AB}$=24.4 Hz, 2H), 7.21-7.25 (m, 2H), 7.33-7.40 (m, 3H), 8.27 (s, 1H).

Step 7. Synthesis of 2,2,2-trifluoroethyl 3-(1-benzyl-4-nitro-1H-pyrazol-5-yl)-N-(tert-butoxycarbonyl)-L-alaninate (C35). C34 was converted to C35 according to the general procedures for the transformation of C16 to C18 in Example 2. C35 was obtained as a white solid. Yield: 448 mg, 0.948 mmol, 74% from step 6. LCMS m/z 373.1 [(M−CO$_2$ and 2-methylprop-1-ene)+1]. $^1$H NMR (400 MHz, CDCl$_3$) δ 1.43 (s, 9H), 3.54 (d, J=7.2 Hz, 2H), 4.39-4.61 (m, 3H), 5.26 (br d, J=7 Hz, 1H), 5.46 (AB quartet, 2 downfield peaks are broad, J$_{AB}$=15.6 Hz, Δv$_{AB}$=34 Hz, 2H), 7.20-7.25 (m, 2H), 7.32-7.39 (m, 3H), 8.16 (s, 1H).

Step 8. Synthesis of tert-butyl[(6S)-1-benzyl-4-hydroxy-5-oxo-4,5,6,7-tetrahydro-1H-pyrazolo[4,3-b]pyridin-6-yl]carbamate (C36). C35 was converted to C36 according to the general procedure for the synthesis of C9 in Example 1. C36 was obtained as a white solid. Yield: 32 mg, 0.089 mmol, 10%; the yield was 32% based on recovered starting material. LCMS m/z 359.2 (M+1). $^1$H NMR (400 MHz, CD$_3$OD) δ 1.45 (s, 9H), 2.81 (br dd, J=16, 13 Hz, 1H), 3.24 (dd, J=15.8, 7.4 Hz, 1H), 4.53 (br dd, J=13, 7.5 Hz, 1H), 5.30 (s, 2H), 7.15-7.19 (m, 2H), 7.26-7.38 (m, 3H), 7.37 (s, 1H).

Step 9. Synthesis of Example 4. C36 was converted to Example 4 according to the general procedure for the synthesis of 3 in Example 3. Example 4 was obtained as a solid. Yield: 27 mg, quantitative. LCMS m/z 241.3 [(M—H$_2$O)+1]. $^1$H NMR (400 MHz, CD$_3$OD) δ 2.90 (dd, J=15.4, 13.7 Hz, 1H), 3.38 (dd, J=15.3, 7.8 Hz, 1H), 4.48 (dd, J=13.5, 7.9 Hz, 1H), 5.35 (AB quartet, J$_{AB}$=15.8 Hz, Δv$_{AB}$=16.7 Hz, 2H), 7.18-7.21 (m, 2H), 7.30-7.39 (m, 3H), 7.45 (s, 1H).

Example 5
(6S)-6-Amino-1-benzyl-4-hydroxy-3-(trifluoromethyl)-1,4,6,7-tetrahydro-5H-pyrazolo[4,3-b]pyridin-5-one, HCl salt (5)
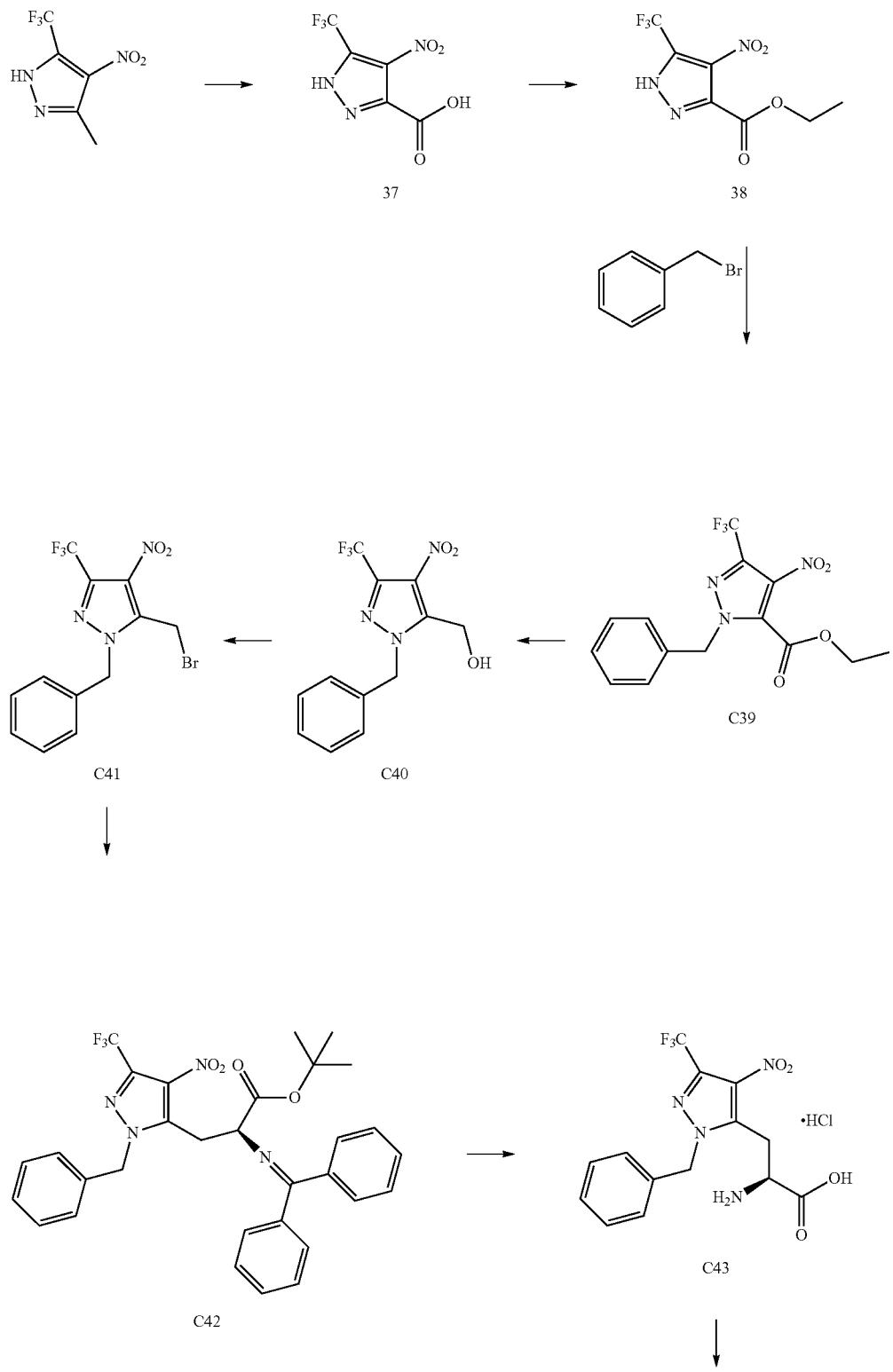

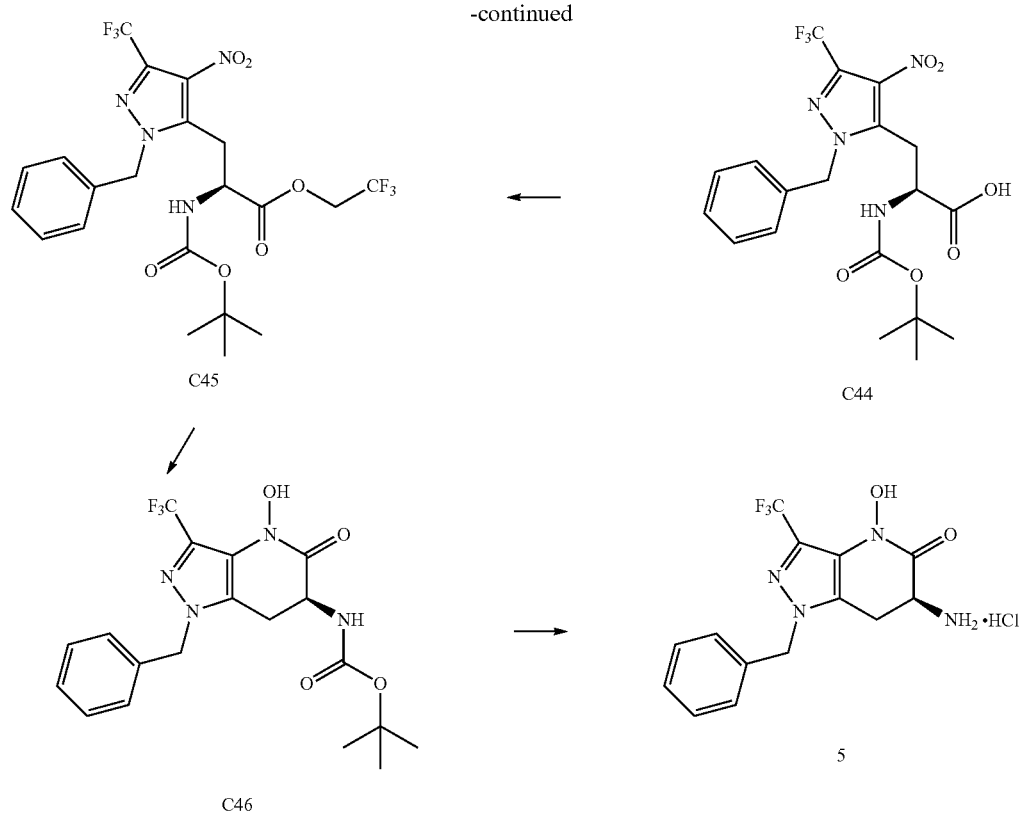

Step 1. Synthesis of 4-nitro-5-(trifluoromethyl)-1H-pyrazole-3-carboxylic acid (C37). Potassium permanganate (56.7 g, 359 mmol) was added to a solution of 3-methyl-4-nitro-5-(trifluoromethyl)-1H-pyrazole (prepared from 3-methyl-5-(trifluoromethyl)-1H-pyrazole as described by B. A. Acker et al., PCT Int. Appl. 2006, WO 2006046135; 20.0 g, 102.5 mmol) in water (400 mL), and the reaction mixture was heated at 100° C. for 12 hours. The mixture was passed through a pad of Celite, and the filtrate was acidified with concentrated HCl, then extracted with EtOAc. The combined organic layers were dried over sodium sulfate, filtered and concentrated in vacuo to afford C37 as a white solid. Yield: 20.0 g, 88.9 mmol, 87%. LCMS m/z 224.0 (M−1). $^{13}$C NMR (75 MHz, DMSO-d$_6$) δ 119.5 (q, $J_{cF}$=269 Hz), 130.9, 133.7, 134.4 (q, $J_{CF}$=39 Hz), 157.4.

Step 2. Synthesis of ethyl 4-nitro-5-(trifluoromethyl)-1H-pyrazole-3-carboxylate (C38). A solution of C37 (20.0 g, 88.9 mmol) in ethanol (200 mL) was cooled to 0° C. HCl gas was bubbled through the reaction mixture for 1 hour, and then the reaction was warmed to RT and allowed to stir for 12 hours. The mixture was cooled to 0° C., and treated with HCl gas in the same manner for 1 hour. It was again warmed to RT and stirred for an additional 12 hours, at which time it was concentrated in vacuo and diluted with dichloromethane. After being washed with water, the organic layer was dried over sodium sulfate, filtered and concentrated under reduced pressure. The resulting material was triturated with pentane to afford C38 as a white solid. Yield: 12.0 g, 47.4 mmol, 53%. LCMS m/z 252.0 (M−1). $^1$H NMR (300 MHz, CDCl$_3$) δ 1.43 (t, J=7.1 Hz, 3H), 4.52 (q, J=7.1 Hz, 2H), 11.66 (br s, 1H).

Step 3. Synthesis of ethyl 1-benzyl-4-nitro-3-(trifluoromethyl)-1H-pyrazole-5-carboxylate (C39). C38 was converted to C39 according to the general procedure for the synthesis of C2 in Example 1, except that the reaction was only allowed to proceed for 2 hours. C39, the major regioisomer, was obtained as a yellow liquid. The regiochemistry of alkylation was assigned based on an HMBC experiment carried out on C39. Yield: 5.0 g, 15 mmol, 74%. GCMS m/z 343.1 (M). $^1$H NMR (300 MHz, CDCl$_3$) δ 1.29 (t, J=7.1 Hz, 3H), 4.37 (q, J=7.1 Hz, 2H), 5.60 (s, 2H), 7.28-7.41 (m, 5H).

Step 4. Synthesis of [1-benzyl-4-nitro-3-(trifluoromethyl)-1H-pyrazol-5-yl]methanol (C40). C39 was converted to C40 according to the general procedure for the synthesis of C31 in Example 4. Upon completion of the reaction, in this case the reaction mixture was concentrated in vacuo, and the residue was partitioned between EtOAc and 1 N aqueous HCl. The organic layer was dried over sodium sulfate, filtered and concentrated. Purification was effected via silica gel chromatography (Eluant: 10% EtOAc in petroleum ether) to afford C40 as a yellow solid. Yield: 3.5 g, 12 mmol, 80%. GCMS m/z 301.1 (M). $^1$H NMR (400 MHz, CDCl$_3$) δ 2.63 (t, J=7.2 Hz, 1H), 4.93 (d, J=7.1 Hz, 2H), 5.53 (s, 2H), 7.25-7.29 (m, 2H, assumed; partially obscured by solvent peak), 7.36-7.43 (m, 3H).

Step 5. Synthesis of 1-benzyl-5-(bromomethyl)-4-nitro-3-(trifluoromethyl)-1H-pyrazole (C41). Carbon tetrabromide (0.80 g, 2.4 mmol) and triphenylphosphine (0.70 g, 2.7 mmol) were added to a 0° C. solution of C40 (0.40 g, 1.3 mmol) in dichloromethane (40 mL), and the reaction was allowed to stir at 0° C. for 30 minutes. After being washed with water, the reaction mixture was dried over sodium sulfate, filtered, and concentrated under reduced pressure. Silica gel chromatography (Eluant: 5% EtOAc in petroleum ether) afforded C41 as a yellow oil. Yield: 0.44 g, 1.2 mmol, 92%. $^1$H NMR (400 MHz, CDCl$_3$) δ 4.67 (s, 2H), 5.52 (s, 2H), 7.26-7.30 (m, 2H, assumed; partially obscured by solvent peak), 7.37-7.45 (m, 3H).

Step 6. Synthesis of tert-butyl 3-[1-benzyl-4-nitro-3-(trifluoromethyl)-1H-pyrazol-5-yl]-N-(diphenylmethylene)-L-alaninate (C42). To a solution of C41 (595 mg, 1.63 mmol) in dichloromethane (13 mL) was added tert-butyl N-(diphenylmethylene)glycinate (98%, 640 mg, 2.12 mmol) and O-allyl-N-(9-anthracenylmethyl)cinchonidinium bromide (95%, 104 mg, 0.163 mmol). The mixture was cooled to −30° C., and cesium hydroxide (357 mg, 2.12 mmol) was added; the reaction was allowed to stir at −30° C. for 16 hours. The reaction was quenched at −30° C. with aqueous ammonium chloride solution, allowed to warm to RT and then extracted twice with dichloromethane. The combined organic layers were washed with water, dried over magnesium sulfate, filtered and concentrated in vacuo. Purification using silica gel chromatography (Gradient: 5% to 25% EtOAc in heptanes) provided C42 as a yellow oil. Yield: 154 mg, 0.266 mmol, 16%. LCMS m/z 579.3 (M+1). $^1$H NMR (400 MHz, CDCl$_3$) δ 1.48 (s, 9H), 3.49 (dd, J=14.2, 10.3 Hz, 1H), 3.68 (dd, J=14.2, 3.5 Hz, 1H), 4.44 (dd, J=10.2, 3.4 Hz, 1H), 5.31 (d, J=15.4 Hz, 1H), 5.73 (d, J=15.5 Hz, 1H), 6.67-6.72 (m, 2H), 7.19-7.24 (m, 2H), 7.32-7.47 (m, 9H), 7.60-7.66 (m, 2H).

Step 7. Synthesis of 3-[1-benzyl-4-nitro-3-(trifluoromethyl)-1H-pyrazol-5-yl]-L-alanine, HCl salt (C43). C42 (120 mg, 0.207 mmol) was treated with a solution of HCl in 1,4-dioxane (4 M, 5 mL), and the reaction mixture was heated to 100° C. for 2 hours. It was then concentrated in vacuo, and the residue was diluted with 1 M aqueous HCl. After being washed with diethyl ether, the aqueous layer was concentrated to provide crude C43 as an off-white solid. Yield: 60 mg, 0.15 mmol, 72%. APCI m/z 358.9 (M+1). $^1$H NMR (300 MHz, DMSO-d$_6$) δ 3.52-3.73 (m, 1H), 3.77-3.90 (m, 1H), 4.14-4.26 (m, 1H), 5.64 (AB quartet, 2 downfield peaks are broad, J$_{AB}$=16 Hz, Δv$_{AB}$=50 Hz, 2H), 7.26-7.44 (m, 5H), 8.73 (br s, 3H).

Step 8. Synthesis of 3-[1-benzyl-4-nitro-3-(trifluoromethyl)-1H-pyrazol-5-yl]-N-(tert-butoxycarbonyl)-L-alanine (C44). C43 was converted to C44 according to the general procedure for the synthesis of C17 in Example 2. In this case, the reaction was carried out for 30 minutes, and at that point, the reaction mixture was concentrated in vacuo. The residue was mixed with aqueous ammonium chloride solution and extracted with EtOAc. The combined organic layers were dried over sodium sulfate, filtered and concentrated under reduced pressure. The residue was triturated with n-pentane to provide C44 as an off-white solid. Yield: 0.80 g, 1.7 mmol, 91%. LCMS m/z 457.0 (M−1). $^1$H NMR (300 MHz, DMSO-d$_6$) δ 1.26 (br s, 9H), 3.10-3.23 (m, 1H), 3.52-3.62 (m, 1H), 4.00-4.13 (m, 1H), 5.56 (AB quartet, J$_{AB}$=15.8 Hz, Δv$_{AB}$=40.1 Hz, 2H), 6.37 (br s, 1H), 7.22-7.29 (m, 2H), 7.31-7.42 (m, 3H).

Step 9. Synthesis of 2,2,2-trifluoroethyl 3-[1-benzyl-4-nitro-3-(trifluoromethyl)-1H-pyrazol-5-yl]-N-(tert-butoxycarbonyl)-L-alaninate (C45). C44 was converted to C45 according to the general procedure for the synthesis of C18 in Example 2, except that in this case, the reaction was carried out at 50° C. for 18 hours, and crude C45 was taken on to the next step without chromatographic purification. Yield: 35 mg, 0.065 mmol, 77%. $^1$H NMR (400 MHz, CDCl$_3$) δ 1.43 (s, 9H), 3.48-3.60 (m, 2H), 4.39-4.63 (m, 3H), 5.25 (br d, J=7 Hz, 1H), 5.54 (AB quartet, 2 downfield peaks are broad, J$_{AB}$=15.4 Hz, Δv$_{AB}$=36 Hz, 2H), 7.24-7.29 (m, 2H), 7.31-7.41 (m, 3H).

Step 10. Synthesis of tert-butyl[(6S)-1-benzyl-4-hydroxy-5-oxo-3-(trifluoromethyl)-4,5,6,7-tetrahydro-1H-pyrazolo[4,3-b]pyridin-6-yl]carbamate (C46). C45 was converted to C46 according to the general procedure for the synthesis of C9 in Example 1. The final material was azeotroped with heptane to remove the last traces of pyridine, providing C46 as a white solid. Yield: 16 mg, 0.038 mmol, 58%. LCMS m/z 427.2 (M+1). $^1$H NMR (400 MHz, CD$_3$OD) δ 1.45 (s, 9H), 2.81 (dd, J=15.6, 13.6 Hz, 1H), 3.26 (dd, J=15.8, 7.3 Hz, 1H), 4.56 (br dd, J=13.3, 7.5 Hz, 1H), 5.35 (s, 2H), 7.20-7.24 (m, 2H), 7.29-7.39 (m, 3H).

Step 11. Synthesis of Example 5. C46 was converted to Example 5 according to the general procedure for the synthesis of 3 in Example 3. After isolation, the product was azeotroped once with methanol, twice with 2-propanol and once with heptane, affording a solid for Example 5. Yield: 10 mg, 0.028 mmol, 69%. LCMS m/z 327.2 (M+1). $^1$H NMR (400 MHz, CD$_3$OD) δ 2.92 (dd, J=15.4, 13.8 Hz, 1H), 3.41 (dd, J=15.4, 7.8 Hz, 1H), 4.54 (dd, J=13.7, 7.8 Hz, 1H), 5.41 (AB quartet, J$_{AB}$=15.6 Hz, Δv$_{AB}$=16.4 Hz, 2H), 7.22-7.26 (m, 2H), 7.32-7.41 (m, 3H).

Example 6

(5S)-5-Amino-7-hydroxy-2-[4-(trifluoromethoxy)benzyl]-2,4,5,7-tetrahydro-6H-pyrazolo[3,4-b]pyridin-6-one, HCl salt (6)

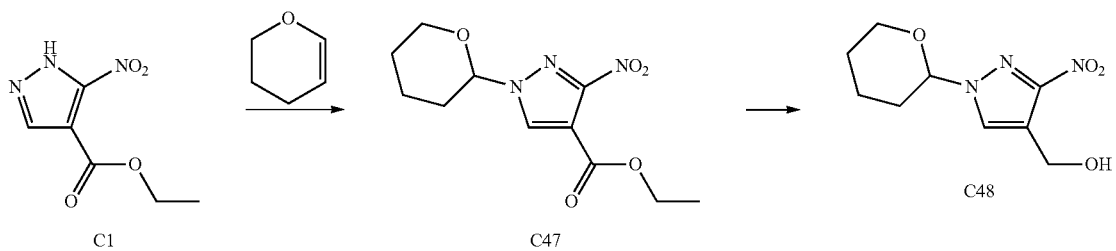

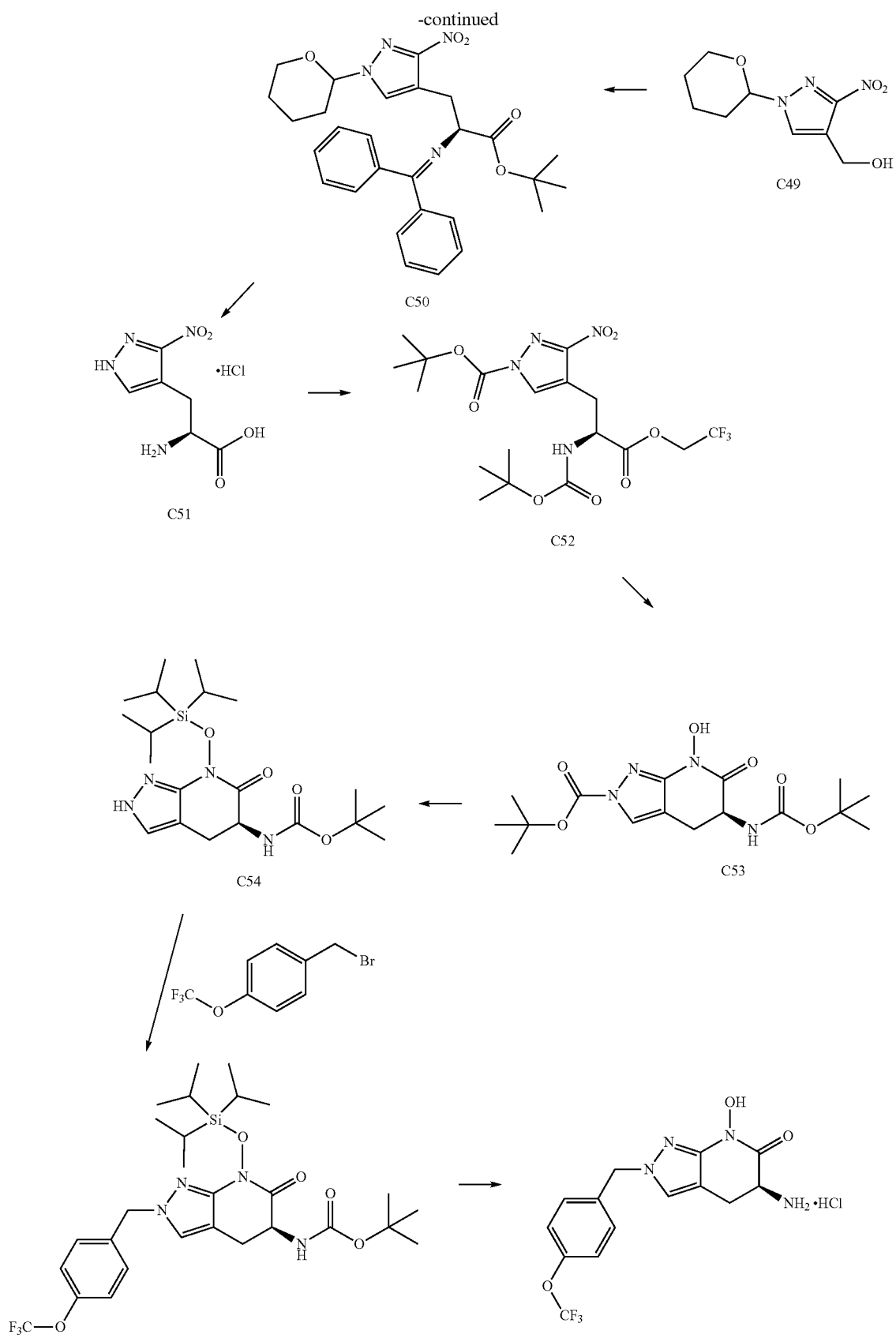

Step 1. Synthesis of ethyl 3-nitro-1-(tetrahydro-2H-pyran-2-yl)-1H-pyrazole-4-carboxylate (C47). 3,4-Dihydro-2H-pyran (95%, 8.66 mL, 90.8 mmol) was added to a solution of C1 (11.2 g, 60.5 mmol) and para-toluenesulfonic acid monohydrate (96%, 3.00 g, 15.1 mmol) in dichloromethane (120 mL), and the reaction was stirred for 20 minutes at RT. The mixture was washed with aqueous sodium bicarbonate solution, then with brine, dried over sodium sulfate, filtered, and concentrated in vacuo to provide C47 as an oil (18 g), which was taken directly into the following reaction without additional purification. The regiochemistry of C47 was supported by an NOE experiment: irradiation of the pyrazole CH resulted in enhancement of the tetrahydropyran methine signal. $^1$H NMR (400 MHz, CDCl$_3$) δ 1.34 (t, J=7.1 Hz, 3H), 1.47-1.76 (m, 3H), 1.93-2.04 (m, 2H), 2.14-2.21 (m, 1H), 3.68-3.76 (m, 1H), 4.02-4.09 (m, 1H), 4.33 (q, J=7.2 Hz, 2H), 5.42 (dd, J=8.6, 2.9 Hz, 1H), 8.13 (s, 1H).

Step 2. Synthesis of [3-nitro-1-(tetrahydro-2H-pyran-2-yl)-1H-pyrazol-4-yl]methanol (C48). C47 was converted to C48 according to the general procedure for the synthesis of C3 in Example 1. C48 was obtained as an oil (15.7 g), which was taken directly to the next step without further purification. $^1$H NMR (400 MHz, CDCl$_3$) δ 1.49-1.78 (m, 3H), 1.97-2.08 (m, 2H), 2.12-2.19 (m, 1H), 3.68-3.76 (m, 1H), 4.03-4.09 (m, 1H), 4.82-4.83 (m, 2H), 5.43 (dd, J=8.8, 2.9 Hz, 1H), 7.75-7.76 (m, 1H).

Step 3. Synthesis of 4-(bromomethyl)-3-nitro-1-(tetrahydro-2H-pyran-2-yl)-1H-pyrazole (C49). Triphenylphosphine (27.0 g, 103 mmol) and carbon tetrabromide (34.5 g, 103 mmol) were added to a solution of C48 (≤60.5 mmol) in dichloromethane (300 mL), and the reaction was allowed to stir at RT for 15 minutes. The reaction mixture was concentrated in vacuo and purified via silica gel chromatography (Gradient: 10% to 50% EtOAc in heptane) to provide C49 as a light orange oil. Yield: 10.6 g, 36.5 mmol, 60% from step 1. $^1$H NMR (400 MHz, CDCl$_3$) δ 1.62-1.76 (m, 3H), 1.95-2.05 (m, 2H), 2.14-2.21 (m, 1H), 3.68-3.76 (m, 1H), 4.03-4.09 (m, 1H), 4.66 (s, 2H), 5.42 (dd, J=8.9, 2.8 Hz, 1H), 7.83 (s, 1H).

Step 4. Synthesis of tert-butyl N-(diphenylmethylene)-3-[3-nitro-1-(tetrahydro-2H-pyran-2-yl)-1H-pyrazol-4-yl]-L-alaninate (C50). C49 was converted to C50 according to the general procedure for the synthesis of C5 in Example 1. C50 was obtained as a solid, judged to be a roughly 1:1 mixture of diastereomers from the proton NMR spectrum. Yield: 14.9 g, 29.5 mmol, 81%. $^1$H NMR (400 MHz, CDCl$_3$) δ 1.42 and 1.44 (2 s, 9H), 1.51-1.72 (m, 3H), 1.82-2.10 (m, 3H), 3.25-3.33 (m, 1H), 3.38-3.47 (m, 1H), 3.55-3.69 (m, 1H), 3.86-3.98 (m, 1H), 4.22-4.29 (m, 1H), 5.33-5.39 (m, 1H), 6.83-6.89 and 6.90-6.96 (2 m, 2H), 7.28-7.34 (m, 2H), 7.36-7.42 (m, 4H), 7.57-7.66 (m, 3H).

Step 5. Synthesis of 3-(3-nitro-1H-pyrazol-4-yl)-L-alanine, HCl salt (C51). C50 (14.8 g, 29.3 mmol) was treated with a solution of HCl in 1,4-dioxane (4 M, 200 mL), and the reaction was heated at 100° C. for 2 hours. The reaction mixture was then concentrated in vacuo and treated with diethyl ether and 1 M aqueous HCl. The aqueous phase was concentrated under reduced pressure to provide a solid; NMR analysis indicated that some tetrahydropyran-protected compound was still present. The solid was therefore resubjected to the reaction conditions for an additional 1.5 hours. After removal of solvent in vacuo, the residue was treated with diethyl ether and 1 M aqueous HCl. The aqueous layer was evaporated to provide C51 as a solid (7.1 g), which was used directly in the following step without additional purification. LCMS m/z 199.1 (M−1). $^1$H NMR (400 MHz, CD$_3$OD) δ 3.32 (dd, J=14.9, 7.6 Hz, 1H, assumed; partially obscured by solvent peak), 3.57 (br dd, J=14.9, 6.0 Hz, 1H), 4.30 (dd, J=7.6, 6.1 Hz, 1H), 7.82 (s, 1H).

Step 6. Synthesis of tert-butyl 4-[(2S)-2-[(tert-butoxycarbonyl)amino]-3-oxo-3-(2,2,2-trifluoroethoxy)propyl]-3-nitro-1H-pyrazole-1-carboxylate (C52). C51 was converted to C52 according to the general procedures for the conversion of C16 to C18 in Example 2. C52 was obtained as a white solid foam. Yield: 8.0 g, 17 mmol, 57% from step 5. LCMS m/z 381.1 [(M—CO$_2$ and 2-methylprop-1-ene)-1]. $^1$H NMR (400 MHz, CDCl$_3$) δ 1.40 (s, 9H), 1.66 (s, 9H), 3.22 (dd, J=14.7, 7.9 Hz, 1H), 3.44 (dd, J=14.8, 5.1 Hz, 1H), 4.46-4.63 (m, 2H), 4.63-4.71 (m, 1H), 5.15 (br d, J=7.4 Hz, 1H), 8.06 (s, 1H).

Step 7. Synthesis of tert-butyl (5S)-5-[(tert-butoxycarbonyl)amino]-7-hydroxy-6-oxo-4,5,6,7-tetrahydro-2H-pyrazolo[3,4-b]pyridine-2-carboxylate (C53). C52 was converted to C53 according to the general procedure for the preparation of C9 in Example 1. C53 was obtained as a white solid. Yield: 3.6 g, 9.8 mmol, 68%. LCMS m/z 369.0 (M+1). $^1$H NMR (400 MHz, CDCl$_3$) δ 1.46 (s, 9H), 1.65 (s, 9H), 2.58 (br dd, J=14, 14 Hz, 1H), 3.33-3.47 (m, 1H), 4.38-4.51 (m, 1H), 5.58-5.68 (m, 1H), 7.78 (s, 1H), 9.76 (br s, 1H).

Step 8. Synthesis of tert-butyl {(5S)-6-oxo-7-[(triisopropylsilyl)oxy]-4,5,6,7-tetrahydro-2H-pyrazolo[3,4-b]pyridin-5-yl}carbamate (C54). A solution of C53 (250 mg, 0.679 mmol) in methanol (10 mL) was treated with lithium hydroxide hydrate (57.0 mg, 1.36 mmol), and the reaction was stirred for 15 minutes. Solvent was removed under reduced pressure at RT, and the residue was partitioned between EtOAc and water. The aqueous phase was concentrated in vacuo at 30° C. to provide the mono-deprotected intermediate as a light orange solid (130 mg) [LCMS m/z 269.1 (M+1)]. A portion of this material (80 mg) was dissolved in N,N-dimethylformamide (3 mL) and treated with triisopropylsilyl chloride (97%, 0.276 mL, 1.26 mmol) and imidazole (86.1 mg, 1.26 mmol). The reaction mixture was allowed to stir for 1 hour at RT, then was diluted with diethyl ether and washed with water. The organic layer was washed with saturated aqueous lithium chloride solution and with saturated aqueous sodium bicarbonate solution, then concentrated in vacuo. Purification via silica gel chromatography (Gradient: 30% to 40% EtOAc in heptane) provided C54 as a white solid. Yield: 75 mg, 0.18 mmol, 42%. LCMS m/z 425.3 (M+1). $^1$H NMR (400 MHz, CDCl$_3$) δ 1.16 (d, J=7.5 Hz, 9H), 1.17 (d, J=7.5 Hz, 9H), 1.34-1.46 (m, 3H), 1.47 (s, 9H), 2.50 (br dd, J=14, 14 Hz, 1H), 3.42 (br dd, J=14, 7 Hz, 1H), 4.36-4.45 (m, 1H), 5.74-5.81 (m, 1H), 7.24-7.26 (m, 1H), 9.79 (br s, 1H).

Step 9. Synthesis of tert-butyl {(5S)-6-oxo-2-[4-(trifluoromethoxy)benzyl]-7-[(triisopropylsilyl)oxy]-4,5,6,7-tetrahydro-2H-pyrazolo[3,4-b]pyridin-5-yl}carbamate (C55). 1-(Bromomethyl)-4-(trifluoromethoxy)benzene (144 mg, 0.565 mmol), potassium iodide (3.8 mg, 0.023 mmol) and potassium carbonate (99%, 47.3 mg, 0.339 mmol) were added to a solution of C54 (48 mg, 0.11 mmol) in N,N-dimethylformamide (2 mL), and the reaction was stirred at RT for 66 hours. After dilution with diethyl ether, the reaction mixture was washed with water. The organic layer was washed with saturated aqueous lithium chloride solution, then concentrated in vacuo. Purification using silica gel chromatography (Gradient: 0% to 30% EtOAc in heptane) provided C55 as a colorless oil. Yield: 37 mg, 0.062 mmol, 56%. LCMS m/z 599.4 (M+1). $^1$H NMR (400 MHz, CDCl$_3$) δ 1.11 (d, J=7.6 Hz, 9H), 1.12 (d, J=7.6 Hz, 9H), 1.28-1.40 (m, 3H), 1.45 (s, 9H), 2.46 (br dd, J=14, 14 Hz, 1H), 3.36 (br dd, J=14.5, 6.6 Hz, 1H), 4.33-4.42 (m, 1H), 5.14 (AB quartet, $J_{AB}$=15.0 Hz, $\Delta v_{AB}$=11.2 Hz, 2H), 5.73-5.80 (m, 1H), 7.10 (s, 1H), 7.15-7.20 (m, 2H), 7.23-7.27 (m, 2H).

Step 10. Synthesis of Example 6. C55 (36 mg, 0.060 mmol) was treated with a solution of HCl in 1,4-dioxane (4 M, 5 mL), and the reaction was allowed to stir for 2 hours. The mixture was filtered, and the solid was washed with diethyl ether to provide a white solid for Example 6. Yield: 17 mg, 0.045 mmol, 75%. LCMS m/z 343.0 (M+1). $^1$H NMR (400 MHz, CD$_3$OD) δ 2.86 (ddd, J=14, 14, 1.1 Hz, 1H), 3.25 (dd, J=14.6, 7.2 Hz, 1H), 4.40 (dd, J=13.7, 7.4 Hz, 1H), 5.28 (s, 2H), 7.25 (br d, J=8 Hz, 2H), 7.39 (br d, J=8.6 Hz, 2H), 7.62-7.63 (br s, 1H).
Example 7
(5S)-5-Amino-7-hydroxy-2-[3-(trifluoromethyl)phenyl]-2,4,5,7-tetrahydro-6H-pyrazolo[3,4-b]pyridin-6-one, HCl salt (7)
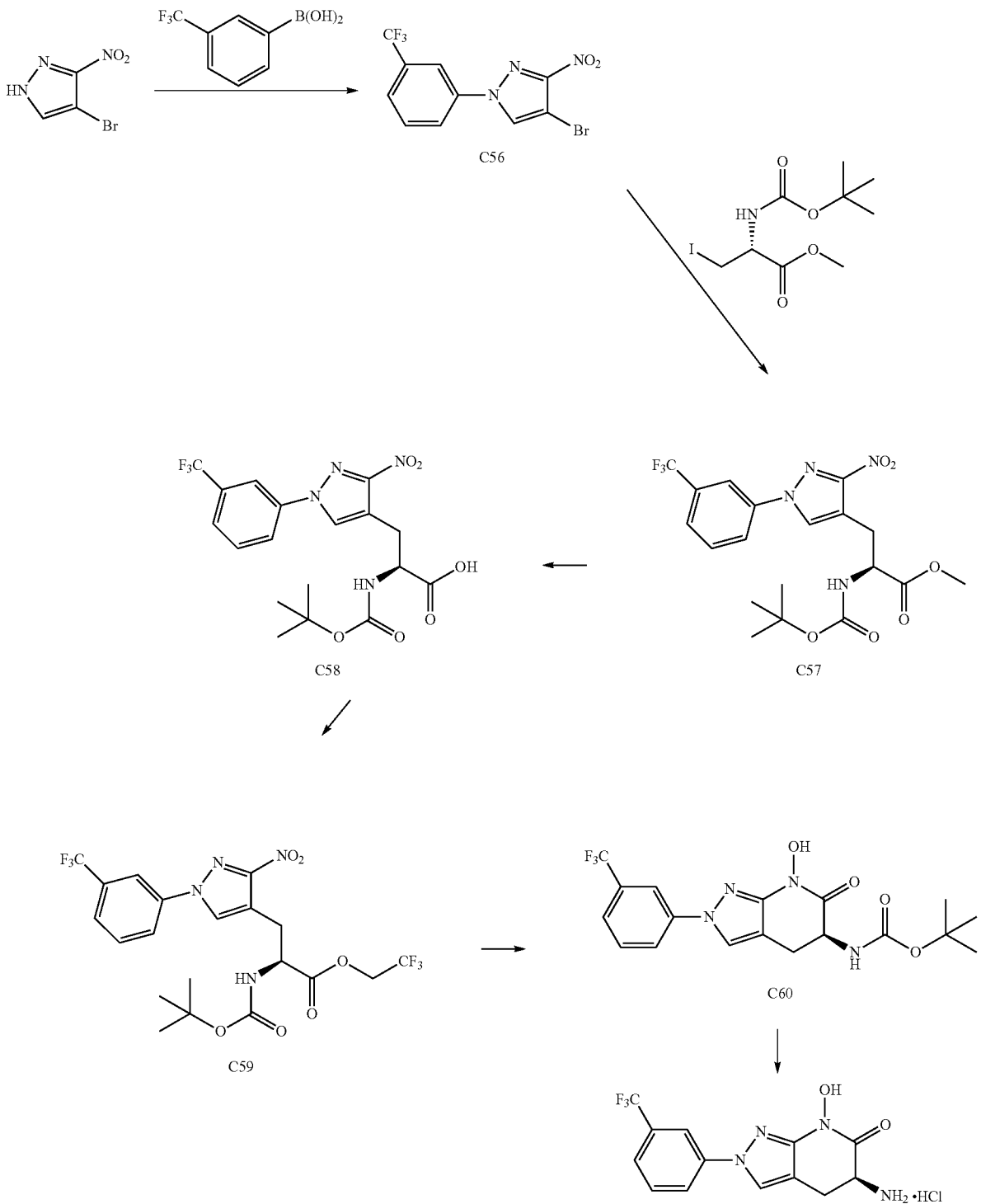

Step 1. Synthesis of 4-bromo-3-nitro-1-[3-(trifluoromethyl)phenyl]-1H-pyrazole (C56). Pyridine (99%, 0.512 mL, 6.27 mmol) and [3-(trifluoromethyl)phenyl]boronic acid (649 mg, 3.42 mmol) were added to a solution of 4-bromo-3-nitro-1H-pyrazole (596.6 mg, 3.108 mmol) in tetrahydrofuran (9 mL); copper(II) acetate (99%, 855 mg, 4.66 mmol) was then added, and the reaction was stirred for 42 hours. The reaction mixture was filtered through Celite and concentrated in vacuo, then partitioned between EtOAc (5 mL) and water (5 mL). The aqueous layer was extracted with EtOAc (3×5 mL), and the combined organic layers were washed with water (5 mL) and dried over sodium sulfate. After filtration and removal of solvent under reduced pressure, the residue was purified via silica gel chromatography (Gradient: 0% to 20% EtOAc in heptane) to provide C56. The regiochemistry of C56 was assigned based on NOE experiments. Yield: 779 mg, 2.32 mmol, 75%. GCMS m/z 335, 337 (M+). $^1$H NMR (400 MHz, CDCl$_3$) δ 7.68-7.76 (m, 2H), 7.94-7.98 (m, 1H), 7.99-8.01 (m, 1H), 8.14 (s, 1H).

Step 2. Synthesis of methyl N-(tert-butoxycarbonyl)-3-{3-nitro-1-[3-(trifluoromethyl)phenyl]-1H-pyrazol-4-yl}-L-alaninate (C57). A dry vial was charged with zinc (99.5%, 494 mg, 7.52 mmol) and N,N-dimethylformamide (2 mL). Trimethylsilyl chloride (95%, 0.20 mL, 1.5 mmol) was added, and the mixture was vigorously stirred for 30 minutes. The yellow supernatant was removed using a syringe, and the zinc was washed with N,N-dimethylformamide (3×2 mL) until the liquid above the zinc was no longer colored. The activated zinc was then dried under vacuum with a heat gun until the zinc was free-flowing. The zinc was allowed to cool to RT, then was treated with a solution of methyl N-(tert-butoxycarbonyl)-3-iodo-L-alaninate (which may be prepared according to S. van Zutphen et al., *Tetrahedron Lett.* 2007, 48, 2857-2859) (recrystallized from petroleum ether; 707 mg, 2.15 mmol) in N,N-dimethylformamide (2 mL); the reaction mixture became very hot. The mixture was stirred at RT until no starting material remained by thin layer chromatographic analysis (about 30 minutes). The grey solution of zinc adduct was transferred to a dry flask, and treated with C56 (602 mg, 1.79 mmol), followed by palladium(II) acetate (4.00 mg, 0.0180 mmol) and 2-dicyclohexylphosphino-2',4',6'-triisopropylbiphenyl (17.2 mg, 0.0360 mmol). After 42 hours at RT, the reaction was filtered through Celite, and the filter pad was washed with EtOAc (3×5 mL). Water (5 mL) was added to the combined filtrates, and the aqueous layer was extracted with EtOAc (3×5 mL). The combined organic layers were washed with water (15 mL), dried over sodium sulfate, filtered and concentrated in vacuo. Purification via silica gel chromatography (0% to 40% EtOAc in heptane) provided C57, contaminated with some impurities (95 mg). This material was taken directly to the following step. LCMS m/z 359.1 [(M—CO$_2$ and 2-methylprop-1-ene)+1]. $^1$H NMR (400 MHz, CD$_3$OD), characteristic peaks: δ 3.12 (dd, J=14.6, 9.7 Hz, 1H), 3.48 (dd, J=14.5, 5.1 Hz, 1H), 4.59 (J=9.7, 4.9 Hz, 1H).

Step 3. Synthesis of N-(tert-butoxycarbonyl)-3-{3-nitro-1-[3-(trifluoromethyl)phenyl]-1H-pyrazol-4-yl}-L-alanine (C58). C57 was converted to C58 according to the general procedure for the synthesis of C21 in Example 3. C58 was obtained as a solid (96 mg) still containing impurities, which was taken directly to the next step. LCMS m/z 443.2 (M−1). $^1$H NMR (400 MHz, CDCl$_3$), characteristic peaks: δ 3.11 (dd, J=14.5, 9.8 Hz, 1H), 3.52 (dd, J=14.6, 4.8 Hz, 1H), 4.56 (dd, J=9.7, 4.6 Hz, 1H).

Step 4. Synthesis of 2,2,2-trifluoroethyl N-(tert-butoxycarbonyl)-3-{3-nitro-1-[3-(trifluoromethyl)phenyl]-1H-pyrazol-4-yl}-L-alaninate (C59). Compound C58 was converted to C59 according to the general procedure for the synthesis of C27 in Example 3. In this case, purification was carried out using silica gel chromatography (Gradient: 0% to 30% EtOAc in heptane), to provide C59 (98.9 mg) still containing impurities. This material was used directly in the next step. LCMS m/z 427.1 [(M—CO$_2$ and 2-methylprop-1-ene)+1]. $^1$H NMR (400 MHz, CDCl$_3$), characteristic peaks: δ 3.30-3.39 (m, 1H), 3.52 (dd, J=14.9, 5.4 Hz, 1H), 4.49-4.66 (m, 2H).

Step 5. Synthesis of tert-butyl {(5S)-7-hydroxy-6-oxo-2-[3-(trifluoromethyl)phenyl]-4,5,6,7-tetrahydro-2H-pyrazolo[3,4-b]pyridin-5-yl}carbamate (C60). Compound C59 was converted to C60 according to the general procedure for the synthesis of C9 in Example 1. C60 was obtained as a solid. Yield: 17.4 mg, 0.0422 mmol, 2% from step 2. LCMS m/z 357.3 {[M-(2-methylprop-1-ene)]+1}. $^1$H NMR (400 MHz, CD$_3$OD) δ 1.48 (s, 9H), 2.84 (br dd, J=15, 14 Hz, 1H), 3.15 (dd, J=15.1, 7.1 Hz, 1H), 4.53 (br dd, J=13.3, 7.1 Hz, 1H), 7.54 (d, J=7.8 Hz, 1H), 7.65 (dd, J=8.0, 8.0 Hz, 1H), 7.97 (br d, J=8 Hz, 1H), 8.04-8.07 (m, 1H), 8.17 (br s, 1H).

Step 6. Synthesis of Example 7. C60 (17.4 mg, 0.0422 mmol) was mixed with a solution of HCl in 1,4-dioxane (4 M, 0.5 mL), and the reaction was stirred for 18 hours. Diethyl ether (2 mL) was added; the resulting product was collected by filtration and washed with diethyl ether (3×3 mL) to provide an off-white solid for Example 7. Yield: 11.7 mg, 0.0336 mmol, 80%. LCMS m/z 313.1 (M+1). $^1$H NMR (400 MHz, CD$_3$OD) δ 2.96 (ddd, J=14.7, 13.7, 1.4 Hz, 1H), 3.37 (dd, J=14.8, 7.4 Hz, 1H), 4.50 (dd, J=13.5, 7.4 Hz, 1H), 7.59 (br d, J=7.9 Hz, 1H), 7.68 (br dd, J=8, 8 Hz, 1H), 7.98-8.02 (m, 1H), 8.07-8.09 (m, 1H), 8.29 (d, J=1.1 Hz, 1H).

Making non-critical changes, the following compounds as provided in Table 1 were prepared using methods discussed herein:

TABLE 1

| Ex # | Structure and IUPAC Name | Method of Preparation | $^1$H NMR (400 MHz, CD$_3$OD), observed peaks, δ; LCMS, observed ion m/z (unless otherwised indicated) |
|---|---|---|---|
| 8 | 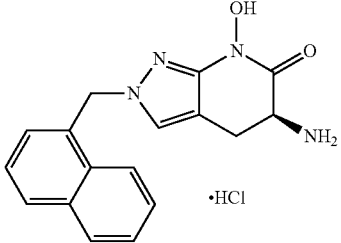 [SMILES: N[C@H]1Cc2cn(Cc3cccc4ccccc34)nc2N(O)C1=O ; Cl]<br>(5S)-5-amino-7-hydroxy-2-(1-naphthylmethyl)-2,4,5,7-tetrahydro-6H-pyrazolo[3,4-b]pyridin-6-one, HCl salt | Ex 1 | $^1$H NMR (300 MHz, DMSO-d$_6$) δ: 2.73 (br dd, J = 14, 14 Hz, 1H), 3.10 (br dd, J = 14, 7 Hz, 1H), 4.29-4.44 (m, 1H), 5.72 (s, 2H), 7.35 (br d, J = 7 Hz, 1H), 7.50 (dd, J = 8.3, 7.1 Hz, 1H), 7.54-7.62 (m, 2H), 7.72 (s, 1H), 7.90-8.00 (m, 2H), 8.17-8.21 (m, 1H), 8.52-8.66 (br m, 2H), 10.7 (v br s, 1H); 309.3 |
| 9 | 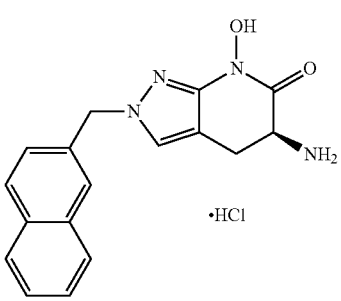 [SMILES: N[C@H]1Cc2cn(Cc3ccc4ccccc4c3)nc2N(O)C1=O ; Cl]<br>(5S)-5-amino-7-hydroxy-2-(2-naphthylmethyl)-2,4,5,7-tetrahydro-6H-pyrazolo[3,4-b]pyridin-6-one, HCl salt | Ex 1 | $^1$H NMR (400 MHz, DMSO-d$_6$) δ: 2.75 (dd, J = 14, 14 Hz, 1H), 3.12 (dd, J = 15, 7 Hz, 1H), 4.34-4.44 (m, 1H), 5.39 (s, 2H), 7.42 (dd, J = 8.6, 1.4 Hz, 1H), 7.49-7.56 (m, 2H), 7.78 (s, 1H), 7.81 (br s, 1H), 7.87-7.94 (m, 3H), 8.51-8.62 (m, 2H), 10.7 (v br s, 1H); 309.0 |
| 10 | 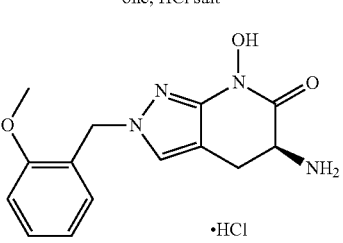<br>(5S)-5-amino-7-hydroxy-2-(2-methoxybenzyl)-2,4,5,7-tetrahydro-6H-pyrazolo[3,4-b]pyridin-6-one, HCl salt | Ex 1 | $^1$H NMR (300 MHz, DMSO-d$_6$) δ: 2.74 (br dd, J = 14, 14 Hz, 1H), 3.12 (dd, J = 14.8, 7.3 Hz, 1H), 3.82 (s, 3H), 4.30-4.45 (m, 1H), 5.17 (s, 2H), 6.91 (ddd, J = 7.5, 7.3, 1.0 Hz, 1H), 6.99-7.06 (m, 2H), 7.31 (ddd, J = 8.2, 7.3, 1.7 Hz, 1H), 7.60 (br s, 1H), 8.54-8.67 (m, 3H), 10.7 (v br s, 1H); 289.2 |
| 11 | 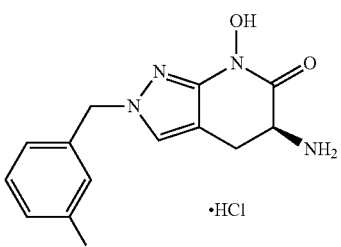<br>(5S)-5-amino-7-hydroxy-2-(3-methoxybenzyl)-2,4,5,7-tetrahydro-6H-pyrazolo[3,4-b]pyridin-6-one, HCl salt | Ex 1 | $^1$H NMR (300 MHz, DMSO-d$_6$) δ: 2.75 (br dd, J = 14, 14 Hz, 1H), 3.12 (dd, J = 14.6, 7.3 Hz, 1H), 3.73 (s, 3H), 4.31-4.45 (m, 1H), 5.18 (s, 2H), 6.80-6.90 (m, 3H), 7.26 (ddd, J = 8.0, 7.3, 0.8 Hz, 1H), 7.72 (s, 1H), 8.53-8.67 (m, 3H), 10.72 (br s, 1H); 289.1 |

TABLE 1-continued

| Ex # | Structure and IUPAC Name | Method of Preparation | $^1$H NMR (400 MHz, CD$_3$OD), observed peaks, δ; LCMS, observed ion m/z (unless otherwised indicated) |
|---|---|---|---|
| 12 | 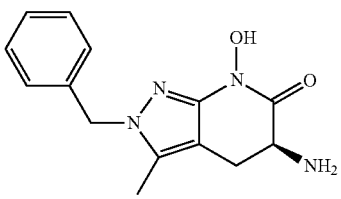<br>(5S)-5-amino-2-benzyl-7-hydroxy-3-methyl-2,4,5,7-tetrahydro-6H-pyrazolo[3,4-b]pyridin-6-one, HCl salt | Ex 1 | 2.20 (s, 3H), 2.78 (dd, J = 14, 14 Hz, 1H), 3.15 (dd, J = 14.3, 7.6 Hz, 1H), 4.39 (dd, J = 13.6, 7.4 Hz, 1H), 5.26 (s, 2H), 7.14-7.18 (m, 2H), 7.26-7.35 (m, 3H); 273.3 |
| 13 | 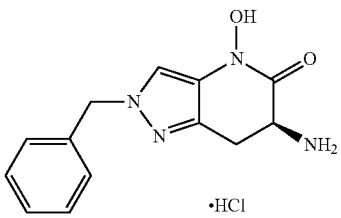 [SMILES: N[C@H]1Cc2nn(Cc3ccccc3)cc2N(O)C1=O ; Cl]<br>(6S)-6-amino-2-benzyl-4-hydroxy-2,4,6,7-tetrahydro-5H-pyrazolo[4,3-b]pyridin-5-one, HCl salt | Ex 3$^1$ | 3.05 (dd, J = 15.0, 13.8 Hz, 1H), 3.34 (dd, J = 15.0, 7.5 Hz, 1H, assumed; partially obscured by solvent peak), 4.47 (dd, J = 13.8, 7.4 Hz, 1H), 5.27 (s, 2H), 7.26-7.37 (m, 5H), 7.63 (s, 1H); 259.1 |
| 14 | 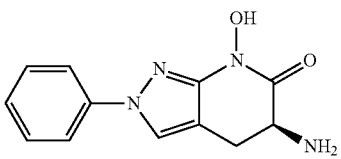<br>(5S)-5-amino-7-hydroxy-2-phenyl-2,4,5,7-tetrahydro-6H-pyrazolo[3,4-b]pyridin-6-one, HCl salt | Ex 3$^2$ | 2.96 (ddd, J = 14, 14, 1.2 Hz, 1H), 3.36 (dd, J = 14.6, 7.4 Hz, 1H), 4.48 (dd, J = 13.7, 7.2 Hz, 1H), 7.30 (br t, J = 7.4 Hz, 1H), 7.47 (br dd, J = 8.6, 7.4 Hz, 2H), 7.70-7.73 (m, 2H), 8.14 (d, J = 1 Hz, 1H); 245.2 |
| 15 | 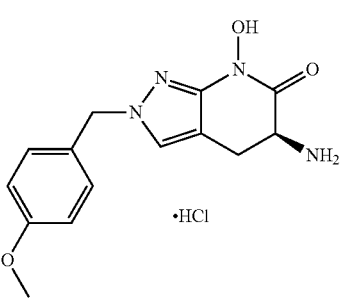 [SMILES: COc1ccc(Cn2cc3c(n2)N(O)C(=O)[C@@H](N)C3)cc1 ; Cl]<br>(5S)-5-amino-7-hydroxy-2-(4-methoxybenzyl)-2,4,5,7-tetrahydro-6H-pyrazolo[3,4-b]pyridin-6-one, HCl salt | Ex 1 | 2.83 (ddd, J = 14, 14, 1 Hz, 1H), 3.21 (dd, J = 14.5, 7.4 Hz, 1H), 3.77 (s, 3H), 4.38 (dd, J = 13.9, 7.3 Hz, 1H), 5.15 (s, 2H), 6.89 (br d, J = 8.7 Hz, 2H), 7.24 (br d, J = 8.5 Hz, 2H), 7.51-7.52 (br s, 1H); 289.1 |

TABLE 1-continued

| Ex # | Structure and IUPAC Name | Method of Preparation | $^1$H NMR (400 MHz, CD$_3$OD), observed peaks, δ; LCMS, observed ion m/z (unless otherwised indicated) |
|---|---|---|---|
| 16 | 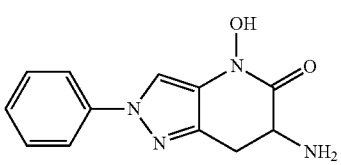<br>•HCl<br>6-amino-4-hydroxy-2-phenyl-2,4,6,7-tetrahydro-5H-pyrazolo[4,3-b]pyridin-5-one, HCl salt | Ex 1$^3$ | 3.16 (br dd, J = 15, 14 Hz, 1H), 3.48 (dd, J = 15.2, 7.4 Hz, 1H), 4.55 (br dd, J = 14, 7 Hz, 1H), 7.32 (br t, J = 8 Hz, 1H), 7.48 (br dd, J = 8, 8 Hz, 2H), 7.73 (br d, J = 8 Hz, 2H), 8.17 (s, 1H); LCMS 227.4 [(M − H$_2$O) + 1] |
| 17 | 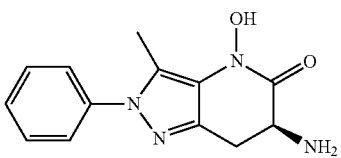<br>•CF$_3$COOH<br>(6S)-6-amino-4-hydroxy-3-methyl-2-phenyl-2,4,6,7-tetrahydro-5H-pyrazolo[4,3-b]pyridin-5-one, trifluoroacetate salt | Ex 1$^4$ | 2.43 (s, 3H), 3.11 (dd, J = 14.9, 14.0 Hz, 1H), 3.31-3.37 (m, 1H, assumed; partially obscured by solvent peak), 4.50 (dd, J = 13.9, 7.1 Hz, 1H), 7.43-7.58 (m, 5H); 259.4 |
| 18 | 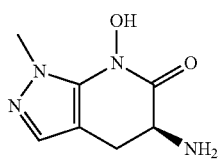<br>•CF$_3$COOH<br>(5S)-5-amino-7-hydroxy-1-methyl-1,4,5,7-tetrahydro-6H-pyrazolo[3,4-b]pyridin-6-one, trifluoroacetate salt | Ex 1$^5$ | 2.85 (ddd, J = 14.5, 13.9, 0.6 Hz, 1H), 3.16 (dd, J = 14.5, 7.3 Hz, 1H), 3.95 (s, 3H), 4.43 (dd, J = 13.9, 7.3 Hz, 1H), 7.30 (d, J = 0.5 Hz, 1H); LCMS m/z 181.2 (M − 1) |
| 19 | 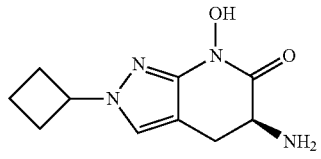<br>•HCl<br>(5S)-5-amino-2-cyclobutyl-7-hydroxy-2,4,5,7-tetrahydro-6H-pyrazolo[3,4-b]pyridin-6-one, HCl salt | Ex 1 | $^1$H NMR (400 MHz, DMSO-d$_6$) δ: 1.69-1.80 (m, 2H), 2.28-2.44 (m, 4H), 2.74 (br dd, J = 14, 14 Hz, 1H), 3.09 (br dd, J = 14, 7 Hz, 1H), 4.33-4.43 (br m, 1H), 4.67-4.77 (m, 1H), 7.67 (s, 1H), 8.56 (br s, 3H), 10.74 (br s, 1H); 223.2 |

TABLE 1-continued

| Ex # | Structure and IUPAC Name | Method of Preparation | $^1$H NMR (400 MHz, CD$_3$OD), observed peaks, δ; LCMS, observed ion m/z (unless otherwised indicated) |
|---|---|---|---|
| 20 | 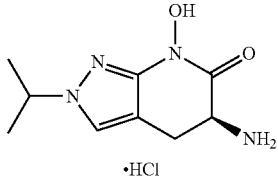<br>(5S)-5-amino-7-hydroxy-2-isopropyl-2,4,5,7-tetrahydro-6H-pyrazolo[3,4-b]pyridin-6-one, HCl salt | Ex 1 | $^1$H NMR (300 MHz, DMSO-d$_6$) δ: 1.37 (d, J = 6.6 Hz, 6H), 2.74 (br dd, J = 14, 14 Hz, 1H), 3.10 (dd, J = 14.6, 7.3 Hz, 1H), 4.31-4.44 (m, 2H), 7.64 (s, 1H), 8.60 (br s, 3H), 10.70 (s, 1H); 211.0 |
| 21 | 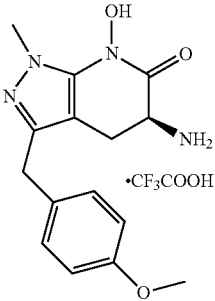<br>(5S)-5-amino-7-hydroxy-3-(4-methoxybenzyl)-1-methyl-1,4,5,7-tetrahydro-6H-pyrazolo[3,4-d]pyridin-6-one, trifluoroacetate salt | Ex 3$^6$ | $^1$H NMR (300 MHz, CD$_3$OD) δ: 2.54 (dd, J = 14.3, 13.9 Hz, 1H), 2.85 (dd, J = 14.5, 7.5 Hz, 1H), 3.75 (s, 3H), 3.83 (br s, 2H), 3.92 (s, 3H), 4.33 (dd, J = 13.8, 7.3 Hz, 1H), 6.84 (br d, J = 8.7 Hz, 2H), 7.12 (br d, J = 8.7 Hz, 2H); 303.2 |
| 22 | 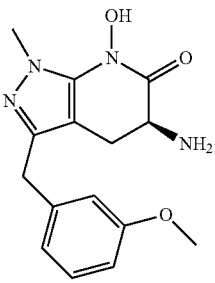<br>(5S)-5-amino-7-hydroxy-3-(3-methoxybenzyl)-1-methyl-1,4,5,7-tetrahydro-6H-pyrazolo[3,4-b]pyridin-6-one, trifluoroacetate salt | Ex 3$^6$ | $^1$H NMR (300 MHz, CD$_3$OD) δ: 2.56 (dd, J = 14.1, 14.1 Hz, 1H), 2.89 (dd, J = 14.5, 7.5 Hz, 1H), 3.75 (s, 3H), 3.87 (br s, 2H), 3.93 (s, 3H), 4.34 (dd, J = 13.8, 7.5 Hz, 1H), 6.74-6.83 (m, 3H), 7.20 (dd, J = 9.0, 7.2 Hz, 1H); 303.3 |

TABLE 1-continued

| Ex # | Structure and IUPAC Name | Method of Preparation | $^1$H NMR (400 MHz, CD$_3$OD), observed peaks, δ; LCMS, observed ion m/z (unless otherwised indicated) |
|---|---|---|---|
| 23 | 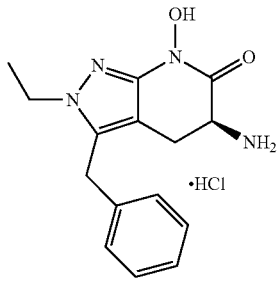 [SMILES: CCn1nc2c(c1Cc1ccccc1)C[C@H](N)C(=O)N2O ; Cl]<br>(5S)-5-amino-3-benzyl-2-ethyl-7-hydroxy-2,4,5,7-tetrahydro-6H-pyrazolo[3,4-b]pyridin-6-one, HCl salt | Ex 3$^7$ | $^1$H NMR (400 MHz, CD$_3$OD) δ: 1.20 (t, J = 7.2 Hz, 3H), 2.67 (dd, J = 14, 14 Hz, 1H), 2.96 (br dd, J = 14.5, 7.4 Hz, 1H), 3.99-4.13 (m, 4H), 4.37 (dd, J = 13.5, 7.4 Hz, 1H), 7.18-7.22 (m, 2H), 7.23-7.28 (m, 1H), 7.31-7.36 (m, 2H); 287.0 |
| 24 | 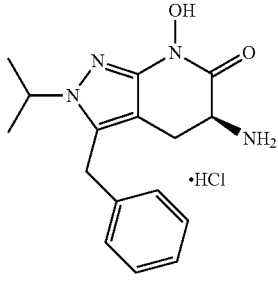 [SMILES: CC(C)n1nc2c(c1Cc1ccccc1)C[C@H](N)C(=O)N2O ; Cl]<br>(5S)-5-amino-3-benzyl-7-hydroxy-2-isopropyl-2,4,5,7-tetrahydro-6H-pyrazolo[3,4-b]pyridin-6-one, HCl salt | Ex 3$^7$ | $^1$H NMR (300 MHz, CD$_3$OD) δ: 1.28 (d, J = 6.6 Hz, 3H), 1.29 (d, J = 6.5 Hz, 3H), 2.73 (dd, J = 14, 14 Hz, 1H), 3.05 (dd, J = 14.5, 7.3 Hz, 1H), 4.08 (AB quartet, J$_{AB}$ = 17 Hz, Δν$_{AB}$ = 8 Hz, 2H), 4.33-4.52 (m, 2H), 7.15-7.37 (m, 5H); 301.0 |
| 25 | 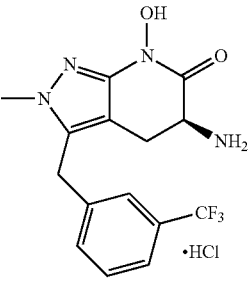 [SMILES: Cn1nc2c(c1Cc1cccc(C(F)(F)F)c1)C[C@H](N)C(=O)N2O ; Cl]<br>(5S)-5-amino-7-hydroxy-2-methyl-3-[3-(trifluoromethyl)benzyl]-2,4,5,7-tetrahydro-6H-pyrazolo[3,4-b]pyridin-6-one, HCl salt | Ex 3$^7$ | $^1$H NMR (300 MHz, CD$_3$OD) δ: 2.67 (dd, J = 14.3, 13.8 Hz, 1H), 2.95 (dd, J = 14.5, 7.5 Hz, 1H), 3.69 (s, 3H), 4.19 (AB quartet, J$_{AB}$ =16.7 Hz, Δν$_{AB}$ = 11.3 Hz, 2H), 4.37 (dd, J = 13.6, 7.5 Hz, 1H), 7.43-7.62 (m, 4H); 341.0 |

TABLE 1-continued

| Ex # | Structure and IUPAC Name | Method of Preparation | ¹H NMR (400 MHz, CD₃OD), observed peaks, δ; LCMS, observed ion m/z (unless otherwised indicated) |
|---|---|---|---|
| 26 | 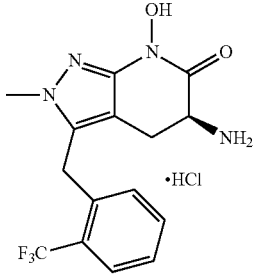 [SMILES: Cn1nc2c(c1Cc1ccccc1C(F)(F)F)C[C@H](N)C(=O)N2O ; Cl]<br>(5S)-5-amino-7-hydroxy-2-methyl-3-[2-(trifluoromethyl)benzyl]-2,4,5,7-tetrahydro-6H-pyrazolo[3,4-b]pyridin-6-one, HCl salt | Ex 3[7] | ¹H NMR (300 MHz, CD₃OD) δ: 2.53 (dd, half of ABX pattern, J = 14.4, 13.7 Hz, 1H), 2.67 (dd, half of ABX pattern, J = 14.5, 7.7 Hz, 1H), 3.68 (s, 3H), 4.27 (brs, 2H), 4.31 (dd, J = 13.4, 7.7 Hz, 1H), 7.19 (br d, J = 7.5 Hz, 1H), 7.49 (br dd, J = 8, 7 Hz, 1H), 7.56-7.63 (m, 1H), 7.78 (br d, J = 7 Hz, 1H); 340.9 |
| 27 | 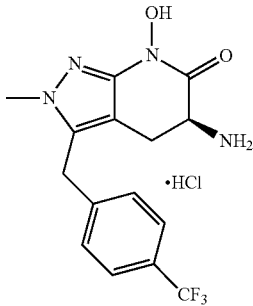 [SMILES: Cn1nc2c(c1Cc1ccc(C(F)(F)F)cc1)C[C@H](N)C(=O)N2O ; Cl]<br>(5S)-5-amino-7-hydroxy-2-methyl-3-[4-(trifluoromethyl)benzyl]-2,4,5,7-tetrahydro-6H-pyrazolo[3,4-6]pyridin-6-one, HCl salt | Ex 3[7] | ¹H NMR (300 MHz, CD₃OD) δ: 2.69 (dd, J = 14.1, 13.9 Hz, 1H), 2.99 (dd, J = 14.5, 7.4 Hz, 1H), 3.69 (s, 3H), 4.18 (AB quartet, $J_{AB}$ =16.9 Hz, $\Delta v_{AB}$ = 9.4 Hz, 2H), 4.39 (dd, J = 13.6, 7.5 Hz, 1H), 7.40 (d, J = 8.0 Hz, 2H), 7.65 (d, J = 8.0 Hz, 2H); 340.9 |
| 28 | 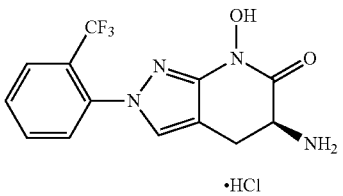 [SMILES: N[C@H]1Cc2cn(-c3ccccc3C(F)(F)F)nc2N(O)C1=O ; Cl]<br>(5S)-5-amino-7-hydroxy-2-[2-(trifluoromethyl)phenyl]-2,4,5,7-tetrahydro-6H-pyrazolo[3,4-b]pyridin-6-one, HCl salt | Ex 7 | 2.96 (ddd, J = 14.7, 13.7, 1.3 Hz, 1H), 3.36 (dd, J = 14.8, 7.4 Hz, 1H), 4.51 (dd, J = 13.7, 7.4 Hz, 1H), 7.59 (br d, J = 8.0 Hz, 1H), 7.71 (br dd, J = 8, 8 Hz, 1H), 7.76 (br s, 1H), 7.78-7.83 (m, 1H), 7.88-7.92 (m, 1H); 313.1 |

TABLE 1-continued

| Ex # | Structure and IUPAC Name | Method of Preparation | $^1$H NMR (400 MHz, CD$_3$OD), observed peaks, δ; LCMS, observed ion m/z (unless otherwised indicated) |
|---|---|---|---|
| 29 | F$_3$C—⟨phenyl⟩—pyrazolo[3,4-b]pyridinone structure with NH$_2$ · HCl<br><br>(5S)-5-amino-7-hydroxy-2-[4-(trifluoromethyl)phenyl]-2,4,5,7-tetrahydro-6H-pyrazolo[3,4-b]pyridin-6-one, HCl salt | Ex 1[8] | 2.97 (ddd, J = 14.7, 13.6, 1.4 Hz, 1H), 3.38 (br dd, J = 14.8, 7.3 Hz, 1H), 4.50 (dd, J = 13.6, 7.3 Hz, 1H), 7.78 (br d, J = 9 Hz, 2H), 7.94 (br d, J = 9 Hz, 2H), 8.28 (br d, J = 1 Hz, 1H); 313.4 |

1. The more polar regioisomer produced during the synthesis of C30 in Example 4 was employed as starting material in place of C20.
2. C1 was converted to the requisite N-phenyl pyrazole starting material (employed in place of C20) using the chemistry described for synthesis of C56 in Example 7. See also P. Y. S. Lam et al., *Tetrahedron Lett.* 1998, 39, 2941-2944.
3. Arylation of C29, followed by ester hydrolysis, to provide 4-nitro-1-phenyl-1H-pyrazole-3-carboxylic acid may be carried out according to T. A. Miller et al., PCT Int. Appl. 2007, WO 2007087129 A2. Subsequent conversion of the carboxylic acid moiety to a primary bromide may be effected as described in Example 2. The resulting 3-(bromomethyl)-4-nitro-1-phenyl-1H-pyrazole was converted to 3-(4-nitro-1-phenyl-1H-pyrazol-3-yl)alanine using chemistry reported by F. Crestey et al., *Tetrahedron* 2006, 62, 7772-7775; this compound was used in place of C6.
4. 5-Methyl-4-nitro-1H-pyrazole-3-carboxylic acid was converted to the corresponding methyl ester, and then N-arylated using the chemistry described in footnote 2. The more polar product upon silica gel chromatography (methyl 5-methyl-4-nitro-1-phenyl-1H-pyrazole-3-carboxylate) was used in place of C1.
5. 1-Methyl-5-nitro-1H-pyrazole-4-carboxylic acid was reduced to the primary alcohol using sodium borohydride and boron trifluoride dimethylate etherate; this alcohol was used in place of C3.
6. Sodium hydride-mediated reaction of ethyl cyanoacetate with a substituted phenylacetyl chloride afforded the appropriately substituted ethyl 2-cyano-3-hydroxy-4-(4-phenyl)but-2-enoate, which was alkylated with ethyl iodide in the presence of silver carbonate to yield the corresponding ethyl 2-cyano-3-ethoxy-4-(4-phenyl)but-2-enoate. Reaction with methylhydrazine in methanol at reflux provided the requisite substituted ethyl 5-amino-3-(benzyl)-1-methyl-1H-pyrazole-4-carboxylate; this was used as starting material. See Y. Xia et al., *J. Med. Chem.* 1997, 40, 4372-4377.
7. The appropriately substituted ethyl 2-cyano-3-hydroxy-4-(4-phenyl)but-2-enoate, prepared as described in footnote 6, was converted to the corresponding ethyl 3-chloro-2-cyano-4-phenylbut-2-enoate by reaction with phosphorus oxychloride and tributylamine. Reaction with the benzaldehyde hydrazone of the requisite substituted hydrazine afforded a 1-substituted ethyl 3-amino-5-benzyl-1H-pyrazole-4-carboxylate, which was used as starting material. See Y. Xia et al., *J. Med. Chem.* 1997, 40, 4372-4377.
8. C1 was subjected to a Suzuki reaction with [4-(trifluoromethyl)phenyl]boronic acid; the resulting ethyl 3-nitro-1-[4-(trifluoromethyl)phenyl]-1H-pyrazole-4-carboxylate was used in place of C2.

KAT II Inhibition Spectra Assay

Formation of kynurenic acid (KYNA) is indirectly assessed by a decrease in light absorbance at 370 nm (OD370) as the L-kynurenine (KYN) substrate is converted by the human KAT II (hKAT II) enzyme into KYNA. An inhibitor would therefore inhibit the decrease in OD370.

The protocol was performed by placing the following reagents into a Costar 384 well black plate (30 μL total assay volume/well):

10 μL of 3× concentrated compound;
  10 μL of 3× concentrated substrate mix (BGG (Sigma G-5009); 3 mM L-Kynurenine in 150 mM Tris Acetate (Sigma K3750); 3 mM α-ketoglutaric acid in 150 mM Tris Acetate (Sigma K2010); and 210 μM pyridoxal 5-phosphate (PLP) in 150 mM Tris Acetate (Sigma 9255)); and
  10 μL of 3× concentrated enzyme (15 nM enzyme in 150 mM Tris Acetate with 0.3% bovine serum).

Plates were sealed and incubated at 37° C. for 15-20 h before reading OD370 on a SpectraMax Plus plate reader. IC$_{50}$s were generated by comparing the efficacy of compounds across a concentration range to inhibit a reduction in the OD370 value relative to assay wells with DMSO added in place of concentrated compound. Biological data for the Examples may be found in Table 2.

TABLE 2

| Ex No. | KATII IC$_{50}$ (nM; single determination unless otherwise indicated) |
|---|---|
| 1 | 59.4 |
| 2 | 63.7[1] |
| 3 | 11.5 |
| 4 | 22.5[1] |
| 5 | 42.7 |
| 6 | 43.6[1] |
| 7 | 74.7[1] |
| 8 | 36.0 |

TABLE 2-continued

| Ex No. | KAT II IC$_{50}$ (nM; single determination unless otherwise indicated) |
|---|---|
| 9 | 117 |
| 10 | 50.2 |
| 11 | 8.93 |
| 12 | 81.6 |
| 13 | 182 |
| 14 | 24.3[1] |
| 15 | 28.3[1] |
| 16 | 85.0[1] |
| 17 | 2010[1] |
| 18 | 329 |
| 19 | 81.3 |
| 20 | 153 |
| 21 | 440 |
| 22 | 65.6 |
| 23 | 24.3 |
| 24 | 63.0 |
| 25 | 42.2 |
| 26 | 40.7 |
| 27 | 37.0[1] |
| 28 | 38.8 |
| 29 | 31.6 |

[1]Value represents the average of 2 IC$_{50}$ determinations

What is claimed is:

1. A compound of Formula I:

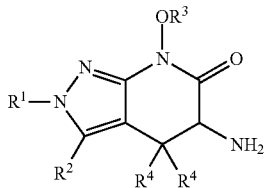

I or a pharmaceutically acceptable salt thereof, wherein $R^1$ is $C_1$ to $C_6$ alkyl, $C_3$ to $C_6$ cycloalkyl, phenyl, naphthyl, —CH$_2$-phenyl, or —CH$_2$-naphthyl, wherein each of said $C_1$ to $C_6$ alkyl, $C_3$ to $C_6$ cycloalkyl, phenyl, naphthyl, —CH$_2$-phenyl, or —CH$_2$-naphthyl may be substituted with one or more substituents independently selected from hydroxy, amino, halo, $C_1$ to $C_6$ alkyl, $C_1$ to $C_6$ haloalkyl, CN, $C_1$ to $C_6$ alkoxy, $C_1$ to $C_6$ haloalkoxy, $C_1$ to $C_6$ alkylamino, $C_1$ to $C_6$ aminoalkyl, —(CH$_2$)$_n$—(C$_3$ to C$_6$ cycloalkyl), —(CH$_2$)$_n$-phenyl, and —(CH$_2$)$_n$-naphthyl;

$R^2$ is H, halo, $C_1$ to $C_6$ alkyl, $C_3$ to $C_6$ cycloalkyl, phenyl, naphthyl, —CH$_2$-phenyl, —CH$_2$-naphthyl, $C_1$ to $C_6$ alkoxy, $C_3$ to $C_6$ cycloalkyloxy, phenyloxy, naphthyloxy, —O—CH$_2$-phenyl, —O—CH$_2$-naphthyl, CN, —(CH$_2$)$_n$NR$^5$R$_6$, C(=O)NR$_5$R$_6$, SO$_2$NR$_5$R$_6$, SO$_2$R$^{5a}$, NR$^5$SO$_2$R$^{5a}$, or NR$^5$C(=O)R$^{5a}$, wherein each of said $C_1$ to $C_6$ alkyl, $C_3$ to $C_6$ cycloalkyl, phenyl, naphthyl, —CH$_2$-phenyl, —CH$_2$-naphthyl, $C_1$ to $C_6$ alkoxy, $C_3$ to $C_6$ cycloalkyloxy, phenyloxy, naphthyloxy, —O—CH$_2$-phenyl, —O—CH$_2$-naphthyl, may be substituted with one or more substituents independently selected from hydroxy, amino, halo, $C_1$ to $C_6$ alkyl, $C_1$ to $C_6$ haloalkyl, CN, $C_1$ to $C_6$ alkoxy, $C_1$ to $C_6$ haloalkoxy, $C_1$ to $C_6$ alkylamino, $C_1$ to $C_6$ aminoalkyl, —(CH$_2$)$_n$—(C$_3$ to C$_6$ cycloalkyl), —(CH$_2$)$_n$-phenyl, and —(CH$_2$)$_n$-naphthyl;

$R^3$ is H, C(=O)R$^7$, C(=O)OR$^7$, C(=O)NR$^{7a}$R$^{7b}$, or (CH$_2$)R$^8$;

each $R^4$ is independently H, methyl, or fluoromethyl;

$R^5$ and $R^6$ are independently H, $C_1$ to $C_6$ alkyl, $C_1$ to $C_6$ fluoroalkyl, phenyl, or naphthyl; or $R^5$ and $R^6$ of C(=O)NR$^5$R$^6$ or SO$_2$NR$^5$R$^6$, together with the nitrogen to which they are attached, may form a heterocycloalkyl that is selected from the group consisting of azepanyl, piperidinyl, pyrrolidinyl, morpholino, thiomorpholino, piperazinyl, and azetidinyl;

$R^{5a}$ is $C_1$ to $C_6$ alkyl, $C_1$ to $C_6$ fluoroalkyl, phenyl, or naphthyl;

$R^7$ is $C_1$ to $C_6$ alkyl, phenyl, naphthyl, or $C_3$ to $C_6$ cycloalkyl, wherein each of said $C_1$ to $C_6$ alkyl, phenyl, naphthyl, and $C_3$ to $C_6$ cycloalkyl may be substituted with one or more substituents independently selected from hydroxy, amino, halo, $C_1$ to $C_6$ alkoxy, and $C_1$ to $C_6$ aminoalkyl;

$R^{7a}$ and $R^{7b}$ are independently H, $C_1$ to $C_6$ alkyl, phenyl, naphthyl, or $C_3$ to $C_6$ cycloalkyl, wherein each of said $C_1$ to $C_6$ alkyl, phenyl, naphthyl, or $C_3$ to $C_6$ cycloalkyl may be substituted with one or more substituents independently selected from hydroxy, amino, halo, $C_1$ to $C_6$ alkoxy, and $C_1$ to $C_6$ aminoalkyl, or, when $R^3$ is C(=O)NR$^{7a}$R$^{7b}$, R$^{7a}$ and R$^{7b}$, together with the nitrogen atom to which they are attached, may form a 5- or 6-membered N-containing heterocyclic ring;

$R^8$ is

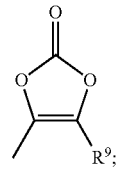

$R^9$ is H, $C_1$ to $C_6$ alkyl, phenyl, naphthyl, or $C_3$ to $C_6$ cycloalkyl, wherein each of said $C_1$ to $C_6$ alkyl, phenyl, naphthyl, or $C_3$ to $C_6$ cycloalkyl may be substituted with one or more substituents independently selected from hydroxy, amino, halo, $C_1$ to $C_6$ alkoxy, and $C_1$ to $C_6$ aminoalkyl; and each n is independently 0, 1, 2, or 3.

2. The compound of claim 1, or a pharmaceutically acceptable salt thereof, wherein $R^1$ is $C_1$ to $C_6$ alkyl; $C_3$ to $C_6$ cycloalkyl, phenyl, napthyl, —CH$_2$-phenyl, or —CH$_2$-naphthyl; $R^2$ is H, $C_1$ to $C_6$ alkyl, $C_3$ to $C_6$ cycloalkyl, phenyl, naphthyl, —CH$_2$-phenyl, or —CH$_2$-naphthyl; and wherein each of said $C_1$ to $C_6$ alkyl, $C_3$ to $C_6$ cycloalkyl, phenyl, naphthyl, —CH$_2$-phenyl, or —CH$_2$-naphthyl may be substituted as allowed in claim 1.

3. The compound of claim 1, or a pharmaceutically acceptable salt thereof, wherein the $C_1$ to $C_6$ alkyl of R$^1$ is $C_1$ to $C_3$ alkyl.

4. The compound of claim 1, or a pharmaceutically acceptable salt thereof, wherein each of said phenyl or napthyl of R$^1$ and R$^2$ may be substituted with one or more substitutes independently selected from halo, $C_1$ to $C_6$ alkyl, $C_1$ to $C_6$ haloalkyl, $C_1$ to $C_6$ alkoxy, $C_1$ to $C_6$ haloalkoxy, and CN.

5. The compound of claim 1, or a pharmaceutically acceptable salt thereof, wherein R$^1$ is $C_1$ to $C_6$ alkyl; R$^2$ is H, phenyl, naphthyl, —CH$_2$-phenyl, or —CH$_2$-naphthyl; and wherein each of said $C_1$ to $C_6$ alkyl, phenyl, naphthyl, —CH$_2$-phenyl, or —CH$_2$-naphthyl may be substituted as allowed in claim 1.

6. The compound of claim 5, or a pharmaceutically acceptable salt thereof, wherein R$^2$ is phenyl, naphthyl, —CH$_2$-phenyl, or —CH$_2$-naphthyl, and wherein each of said phenyl or naphthyl may be substituted with one or more substituents independently selected from halo, $C_1$ to $C_6$ alkyl, $C_1$ to $C_6$ haloalkyl, $C_1$ to $C_6$ alkoxy, $C_1$ to $C_6$ haloalkoxy, and CN.

7. The compound of claim 1, or a pharmaceutically acceptable salt thereof, wherein $R^3$ is H and each $R^4$ is H.

8. The compound of claim 1, or a pharmaceutically acceptable salt thereof wherein the $NH_2$ of compounds of formula I has the following stereochemistry:

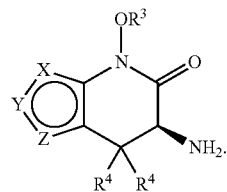

9. A compound selected from:
(5S)-5-Amino-2-benzyl-7-hydroxy-2,4,5,7-tetrahydro-6H-pyrazolo[3,4-b]pyridin-6-one;
(5S)-5-amino-7-hydroxy-2-phenyl-2,4,5,7-tetrahydro-6H-pyrazolo[3,4-b]pyridin-6-one; and
(5S)-5-amino-3-benzyl-2-ethyl-7-hydroxy-2,4,5,7-tetrahydro-6H-pyrazolo[3,4-b]pyridin-6-one,
or a pharmaceutically acceptable salt thereof.

10. A compound that is (5S)-5-amino-7-hydroxy-2-phenyl-2,4,5,7-tetrahydro-6H-pyrazolo[3,4-b]pyridin-6-one or a pharmaceutically acceptable salt thereof.

11. A pharmaceutical composition comprising a compound of claim 1, or a pharmaceutically acceptable salt thereof, and a pharmaceutically acceptable carrier.

12. A pharmaceutical composition comprising a compound of claim 9, or a pharmaceutically acceptable salt thereof, and a pharmaceutically acceptable carrier.

13. A pharmaceutical composition comprising a compound of claim 10, or a pharmaceutically acceptable salt thereof, and a pharmaceutically acceptable carrier.

14. A compound selected from:
(5S)-5-amino-2-benzyl-7-hydroxy-2,4,5,7-tetrahydro-6H-pyrazolo[3,4-b]pyridin-6-one;
(5S)-5-amino-3-benzyl-7-hydroxy-2-methyl-2,4,5,7-tetrahydro-6H-pyrazolo[3,4-b]pyridin-6-one;
(5S)-5-amino-7-hydroxy-2-[4-(trifluoromethoxy)benzyl]-2,4,5,7-tetrahydro-6H-pyrazolo[3,4-b]pyridin-6-one;
(5S)-5-amino-7-hydroxy-2-[3-(trifluoromethyl)phenyl]-2,4,5,7-tetrahydro-6H-pyrazolo[3,4-b]pyridin-6-one
(5S)-5-amino-7-hydroxy-2-(1-naphthylmethyl)-2,4,5,7-tetrahydro-6H-pyrazolo[3,4-b]pyridin-6-one
(5S)-5-amino-7-hydroxy-2-(2-naphthylmethyl)-2,4,5,7-tetrahydro-6H-pyrazolo[3,4-b]pyridin-6-one;
(5S)-5-amino-7-hydroxy-2-(2-methoxybenzyl)-2,4,5,7-tetrahydro-6H-pyrazolo[3,4-b]pyridin-6-one;
(5S)-5-amino-7-hydroxy-2-(3-methoxybenzyl)-2,4,5,7-tetrahydro-6H-pyrazolo[3,4-b]pyridin-6-one;
(5S)-5-amino-2-benzyl-7-hydroxy-3-methyl-2,4,5,7-tetrahydro-6H-pyrazolo[3,4-b]pyridin-6-one;
(5S)-5-amino-7-hydroxy-2-phenyl-2,4,5,7-tetrahydro-6H-pyrazolo[3,4-b]pyridin-6-one;
(5S)-5-amino-7-hydroxy-2-(4-methoxybenzyl)-2,4,5,7-tetrahydro-6H-pyrazolo[3,4-b]pyridin-6-one;
(5S)-5-amino-2-cyclobutyl-7-hydroxy-2,4,5,7-tetrahydro-6H-pyrazolo[3,4-b]pyridin-6-one,
(5S)-5-amino-7-hydroxy-2-isopropyl-2,4,5,7-tetrahydro-6H-pyrazolo[3,4-b]pyridin-6-one,
(5S)-5-amino-3-benzyl-2-ethyl-7-hydroxy-2,4,5,7-tetrahydro-6H-pyrazolo[3,4-b]pyridin-6-one;
(5S)-5-amino-3-benzyl-7-hydroxy-2-isopropyl-2,4,5,7-tetrahydro-6H-pyrazolo[3,4-b]pyridin-6-one;
(5S)-5-amino-7-hydroxy-2-methyl-3-[3-(trifluoromethyl)benzyl]-2,4,5,7-tetrahydro-6H-pyrazolo[3,4-b]pyridin-6-one;
(5S)-5-amino-7-hydroxy-2-methyl-3-[2-(trifluoromethyl)benzyl]-2,4,5,7-tetrahydro-6H-pyrazolo[3,4-b]pyridin-6-one;
(5S)-5-amino-7-hydroxy-2-methyl-3-[4-(trifluoromethyl)benzyl]-2,4,5,7-tetrahydro-6H-pyrazolo[3,4-b]pyridin-6-one;
(5S)-5-amino-7-hydroxy-2-[2-(trifluoromethyl)phenyl]-2,4,5,7-tetrahydro-6H-pyrazolo[3,4-b]pyridin-6-one; and
(5S)-5-amino-7-hydroxy-2-[4-(trifluoromethyl)phenyl]-2,4,5,7-tetrahydro-6H-pyrazolo[3,4-b]pyridin-6-one,
or a pharmaceutically acceptable salt thereof.

15. A pharmaceutical composition comprising a compound of claim 14, or a pharmaceutically acceptable salt thereof, and a pharmaceutically acceptable carrier.

* * * * *